United States Patent
Hauptmann et al.

(10) Patent No.: US 11,015,198 B2
(45) Date of Patent: May 25, 2021

(54) PRODUCTS AND COMPOSITIONS

(71) Applicant: SILENCE THERAPEUTICS GMBH, Berlin (DE)

(72) Inventors: Judith Hauptmann, Berlin (DE); Dmitry Samarsky, Berlin (DE); Christian Frauendorf, Berlin (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 0 days.

(21) Appl. No.: 16/497,000

(22) PCT Filed: Apr. 5, 2018

(86) PCT No.: PCT/EP2018/058766
§ 371 (c)(1),
(2) Date: Sep. 24, 2019

(87) PCT Pub. No.: WO2018/185241
PCT Pub. Date: Oct. 11, 2018

(65) Prior Publication Data
US 2020/0095580 A1  Mar. 26, 2020

(30) Foreign Application Priority Data

| Apr. 5, 2017 | (EP) | 17165129 |
| May 5, 2017 | (GB) | 1707203 |
| May 25, 2017 | (GB) | 1708397 |
| Nov. 13, 2017 | (EP) | 17201352 |

(51) Int. Cl.
*C12N 15/113* (2010.01)

(52) U.S. Cl.
CPC ........ *C12N 15/113* (2013.01); *C12N 2310/14* (2013.01); *C12N 2310/313* (2013.01); *C12N 2310/321* (2013.01); *C12N 2310/322* (2013.01); *C12N 2310/351* (2013.01)

(58) Field of Classification Search
CPC .............. C12N 15/113; C12N 2310/14; C12N 2310/313; C12N 2310/321; C12N 2310/322; C12N 2310/351
See application file for complete search history.

(56) References Cited

U.S. PATENT DOCUMENTS

| 8,013,146 | B2 | 9/2011 | McSwiggen et al. |
| 10,233,448 | B2 * | 3/2019 | Maier .................. C12N 15/113 |
| 10,612,024 | B2 * | 4/2020 | Maier .................. C12N 15/111 |
| 10,612,027 | B2 * | 4/2020 | Maier .................. C12N 15/111 |
| 10,633,654 | B2 | 4/2020 | Pavco et al. |
| 2005/0080246 | A1 | 4/2005 | Allerson et al. |

FOREIGN PATENT DOCUMENTS

| WO | 2007112414 A1 | 10/2007 |
| WO | 2009002944 A1 | 12/2008 |
| WO | WO-2009134487 A2 | 11/2009 |
| WO | 2010078536 A1 | 7/2010 |
| WO | WO-2012094115 A1 | 7/2012 |
| WO | WO-2013003520 A1 | 1/2013 |
| WO | 2013074974 A2 | 5/2013 |
| WO | 2013075035 A1 | 5/2013 |
| WO | WO-2013155204 A2 | 10/2013 |
| WO | WO-2013163430 A2 | 10/2013 |
| WO | WO-2014089313 A1 | 6/2014 |
| WO | WO-2016028649 A1 | 2/2016 |
| WO | 2016085852 A1 | 6/2016 |
| WO | WO-2016149020 A1 | 9/2016 |
| WO | WO-2016149331 A2 | 9/2016 |
| WO | 2016161388 A1 | 10/2016 |
| WO | 2017030973 A1 | 2/2017 |
| WO | WO-2017027350 A2 | 2/2017 |
| WO | WO-2017059223 A2 | 4/2017 |
| WO | WO-2017214112 A1 | 12/2017 |

OTHER PUBLICATIONS

Allerson et al. "Fully 2'-modified oglionucleotide duplexes with improved in vitro potency and stability compared to unmodified small interfering RNA." Journal of Medicinal Chemistry, American Chemical Society 48(4): 901-904 (2005).

Bramsen et al. "A large-scale chemical modification screen identifies design rules to generate siRNAs with high activity, high stability and low toxicity." Nucleic Acids Research 37(9): 2867-2881 (2009).

* cited by examiner

*Primary Examiner* — Brian Whiteman
(74) *Attorney, Agent, or Firm* — Marshall, Gerstein & Borun LLP

(57) ABSTRACT

The present invention relates to products and compositions and their uses. In particular the invention relates to nucleic acid products that interfere with gene expression or inhibits its expression and therapeutic uses such as for the treatment of disease and disorders.

7 Claims, 24 Drawing Sheets
Specification includes a Sequence Listing.

Figure 1a

| Duplex ID | sequence and chemistry top: first strand, bottom: second strand, both 5'-3' | |
|---|---|---|
| CLC01 | mAUmGCmAAmAAmUAmCAmCUmUCmUAmC | SEQ ID NO: 11 |
| | GmUAmGAmAGmUGmUAmUUmUUmGCmAU | SEQ ID NO: 12 |
| CLC15 | AmUGmCAmAAmAUmACmACmUUmCUmAC | SEQ ID NO: 19 |
| | mGUmAGmAAmGUmGUmAUmUUmUGmCAmU | SEQ ID NO: 20 |
| CLC16 | AmUGmCAmAAmAUmACmACUUmCUmAC | SEQ ID NO: 17 |
| | mGUmAGmAAmGUmGUmAUmUUmUGmCAmU | SEQ ID NO: 20 |

A, U, C, G - RNA
mA, mU, mC, mG – 2'-OMe RNA

Figure 1b

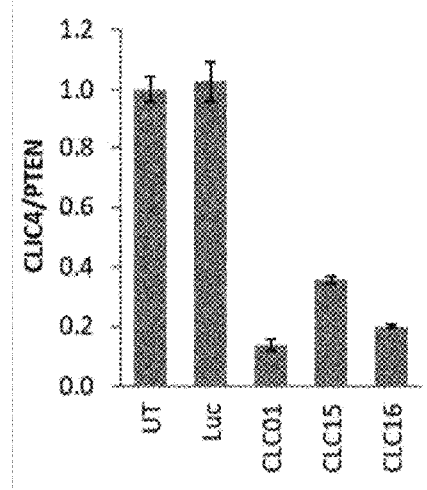

| Duplex ID | sequence and chemistry<br>top: first strand, bottom: second strand, both 5'-3' | |
|---|---|---|
| CLC01 | mAUmGCmAAmAAmUAmCAmCUmUCmUAmC | SEQ ID NO: 11 |
|  | GmUAmGAmAGmUGmUAmUUmUUmGCmAU | SEQ ID NO:12 |
| CLC22 | AUGmCAAAAmUACACmUUCUAC | SEQ ID NO: 13 |
|  | GmUAGAAGmUGmUAmUmUmUmGmCAmU | SEQ ID NO: 14 |
| CLC28 | AUGmCAAAAmUACACUmUCUAC | SEQ ID NO: 15 |
|  | GmUAGAAGmUGmUAmUmUmUmUGmCAmU | SEQ ID NO: 16 |

A, U, C, G - RNA
mA, mU, mC, mG – 2'-OMe RNA

| Duplex ID | sequence and chemistry<br>top: first strand, bottom: second strand, both 5'-3' | |
|---|---|---|
| CLC56 | AmUGmCAmAAmAUmACmACUUmCUmAC | SEQ ID NO: 17 |
| | mGUmAGmAAmGUGUmAUmUUmUGmCAmU | SEQ ID NO: 8 |
| CLC57 | AUmGCAmAAmAUmACmACUUmCUmAC | SEQ ID NO: 9 |
| | mGUmAGmAAmGUGUmAUmUUmUGmCAmU | SEQ ID NO: 10 |

A, U, C, G - RNA
mA, mU, mC, mG – 2'-OMe RNA

Figure 4a

| Duplex ID | sequence and chemistry<br>top: first strand, bottom: second strand, both 5'-3' |
|---|---|
| CLC01 | mAUmGCmAAmAAmUAmCAmCUmUCmUAmC  SEQ ID NO: 11 |
|  | GmUAmGAmAGmUGmUAmUUmUUmGCmAU  SEQ ID NO: 12 |
| CLC28 | AUGmCAAAAmUACACUmUCUAC  SEQ ID NO: 15 |
|  | GmUAGAAGmUGmUAmUmUmUmUGmCAmU  SEQ ID NO: 16 |
| CLC59 | AmUGCAAAAmUACACUmUCUAC  SEQ ID NO: 3 |
|  | GmUAGAAGmUGmUAmUmUmUmUGmCAmU  SEQ ID NO: 4 |
| CLC60 | AUmGCAAAAmUACACUmUCUAC  SEQ ID NO: 5 |
|  | GmUAGAAGmUGmUAmUmUmUmUGmCAmU  SEQ ID NO: 6 |

A, U, C, G – RNA
mA, mU, mC, mG – 2'-OMe RNA

Figure 4b

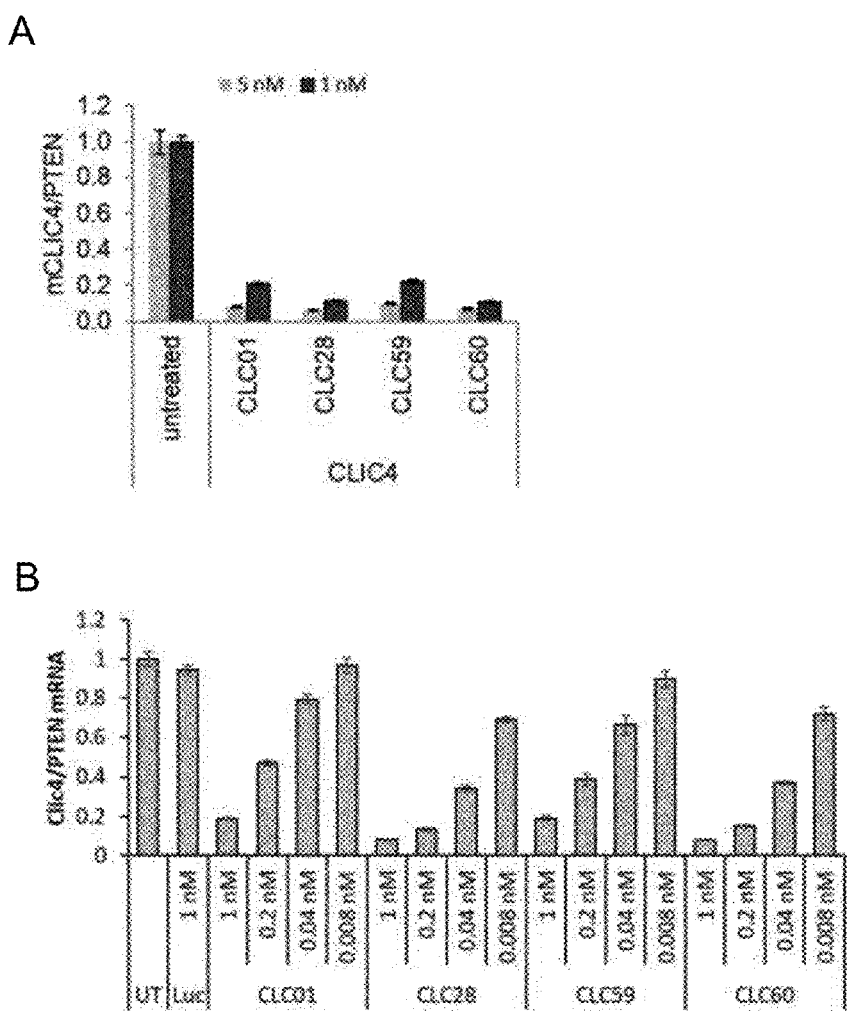

| Duplex ID | sequence and chemistry<br>top: first strand, bottom: second strand, both 5'-3' | |
|---|---|---|
| HFE04 | fAfUmUfGfAmUfAfGfAfAmCfCfAfUmCfUfUmCfA | SEQ ID NO:21 |
|  | mUfGfAfAfGfAmUfGfGmUmUmCmUfAmUmCfAfAmU | SEQ ID NO: 22 |
| HFE06 | fAmUfUfGfAmUfAfGfAfAmCfCfAfUmCfUfUmCfA | SEQ ID NO:23 |
|  | mUfGfAfAfGfAmUfGfGmUmUmCmUfAmUmCfAfAmU | SEQ ID NO: 24 |

A, U, C, G - RNA
mA, mU, mC, mG – 2'-OMe RNA
fA, fU, fC, fG – 2'-F RNA

Figure 6B:
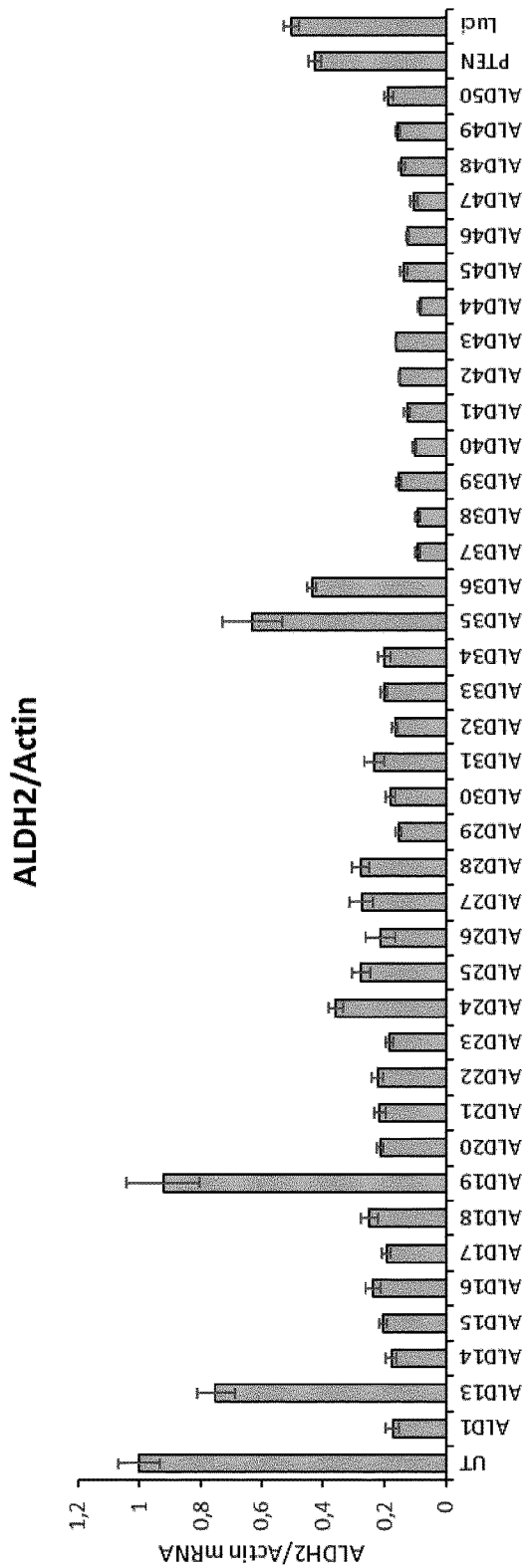

Figure 6a: Sequences used in Figures 6b and 6c

| Duplex ID | sequence and chemistry<br>top: first strand, bottom: second strand, both 5'-3' | SEQ ID NO: |
|---|---|---|
| ALD01 | mA(ps)fA(ps)mUfGmUfUmUfUmCfCmUfGmCfUmGfAmC(ps)fG(ps)mG | 25 |
|  | fC(ps)mC(ps)fGmUfCmAfGmCfAmGfGmAfAmAfAmCfA(ps)mU(ps)fU | 26 |
| ALD13 | mA(ps)mA(ps)mUfGmUfUmUfUmCfCmUfGmCfUmGfAmC(ps)fG(ps)mG | 27 |
|  | fC(ps)mC(ps)fGmUfCmAfGmCfAmGfGmAfAmAfAmCfA(ps)mU(ps)fU | 28 |
| ALD14 | mA(ps)fA(ps)mUmGmUfUmUfUmCfCmUfGmCfUmGfAmC(ps)fG(ps)mG | 29 |
|  | fC(ps)mC(ps)fGmUfCmAfGmCfAmGfGmAfAmAfAmCfA(ps)mU(ps)fU | 30 |
| ALD15 | mA(ps)fA(ps)mUfGmUmUmUfUmCfCmUfGmCfUmGfAmC(ps)fG(ps)mG | 31 |
|  | fC(ps)mC(ps)fGmUfCmAfGmCfAmGfGmAfAmAfAmCfA(ps)mU(ps)fU | 32 |
| ALD16 | mA(ps)fA(ps)mUfGmUfUmUmUmCfCmUfGmCfUmGfAmC(ps)fG(ps)mG | 33 |
|  | fC(ps)mC(ps)fGmUfCmAfGmCfAmGfGmAfAmAfAmCfA(ps)mU(ps)fU | 34 |
| ALD17 | mA(ps)fA(ps)mUfGmUfUmUfUmCmCmUfGmCfUmGfAmC(ps)fG(ps)mG | 35 |
|  | fC(ps)mC(ps)fGmUfCmAfGmCfAmGfGmAfAmAfAmCfA(ps)mU(ps)fU | 36 |
| ALD18 | mA(ps)fA(ps)mUfGmUfUmUfUmCfCmUmGmCfUmGfAmC(ps)fG(ps)mG | 37 |
|  | fC(ps)mC(ps)fGmUfCmAfGmCfAmGfGmAfAmAfAmCfA(ps)mU(ps)fU | 38 |
| ALD19 | mA(ps)fA(ps)mUfGmUfUmUfUmCfCmUfGmCmUmGfAmC(ps)fG(ps)mG | 39 |
|  | fC(ps)mC(ps)fGmUfCmAfGmCfAmGfGmAfAmAfAmCfA(ps)mU(ps)fU | 40 |
| ALD20 | mA(ps)fA(ps)mUfGmUfUmUfUmCfCmUfGmCfUmGmAmC(ps)fG(ps)mG | 41 |
|  | fC(ps)mC(ps)fGmUfCmAfGmCfAmGfGmAfAmAfAmCfA(ps)mU(ps)fU | 42 |
| ALD21 | mA(ps)fA(ps)mUfGmUfUmUfUmCfCmUfGmCfUmGfAmC(ps)mG(ps)mG | 43 |
|  | fC(ps)mC(ps)fGmUfCmAfGmCfAmGfGmAfAmAfAmCfA(ps)mU(ps)fU | 44 |
| ALD22 | fA(ps)fA(ps)mUfGmUfUmUfUmCfCmUfGmCfUmGfAmC(ps)fG(ps)mG | 45 |
|  | fC(ps)mC(ps)fGmUfCmAfGmCfAmGfGmAfAmAfAmCfA(ps)mU(ps)fU | 46 |
| ALD23 | mA(ps)fA(ps)fUfGmUfUmUfUmCfCmUfGmCfUmGfAmC(ps)fG(ps)mG | 47 |
|  | fC(ps)mC(ps)fGmUfCmAfGmCfAmGfGmAfAmAfAmCfA(ps)mU(ps)fU | 48 |
| ALD24 | mA(ps)fA(ps)mUfGfUfUmUfUmCfCmUfGmCfUmGfAmC(ps)fG(ps)mG | 49 |
|  | fC(ps)mC(ps)fGmUfCmAfGmCfAmGfGmAfAmAfAmCfA(ps)mU(ps)fU | 50 |
| ALD25 | mA(ps)fA(ps)mUfGmUfUfUfUmCfCmUfGmCfUmGfAmC(ps)fG(ps)mG | 51 |
|  | fC(ps)mC(ps)fGmUfCmAfGmCfAmGfGmAfAmAfAmCfA(ps)mU(ps)fU | 52 |
| ALD26 | mA(ps)fA(ps)mUfGmUfUmUfUfCfCmUfGmCfUmGfAmC(ps)fG(ps)mG | 53 |
|  | fC(ps)mC(ps)fGmUfCmAfGmCfAmGfGmAfAmAfAmCfA(ps)mU(ps)fU | 54 |
| ALD27 | mA(ps)fA(ps)mUfGmUfUmUfUmCfCfUfGmCfUmGfAmC(ps)fG(ps)mG | 55 |
|  | fC(ps)mC(ps)fGmUfCmAfGmCfAmGfGmAfAmAfAmCfA(ps)mU(ps)fU | 56 |
| ALD28 | mA(ps)fA(ps)mUfGmUfUmUfUmCfCmUfGfCfUmGfAmC(ps)fG(ps)mG | 57 |
|  | fC(ps)mC(ps)fGmUfCmAfGmCfAmGfGmAfAmAfAmCfA(ps)mU(ps)fU | 58 |
| ALD29 | mA(ps)fA(ps)mUfGmUfUmUfUmCfCmUfGmCfUfGfAmC(ps)fG(ps)mG | 59 |
|  | fC(ps)mC(ps)fGmUfCmAfGmCfAmGfGmAfAmAfAmCfA(ps)mU(ps)fU | 60 |
| ALD30 | mA(ps)fA(ps)mUfGmUfUmUfUmCfCmUfGmCfUmGfAfC(ps)fG(ps)mG | 61 |
|  | fC(ps)mC(ps)fGmUfCmAfGmCfAmGfGmAfAmAfAmCfA(ps)mU(ps)fU | 62 |
| ALD31 | mA(ps)fA(ps)mUfGmUfUmUfUmCfCmUfGmCfUmGfAmC(ps)fG(ps)fG | 63 |
|  | fC(ps)mC(ps)fGmUfCmAfGmCfAmGfGmAfAmAfAmCfA(ps)mU(ps)fU | 64 | mA, mU, mC, mG – 2'-OMe RNA
fA, fU, fC, fG – 2'-F RNA
(ps) – phosphorothioate

Figure 6a (continued):

| Duplex ID | sequence and chemistry top: first strand, bottom: second strand, both 5'-3' | SEQ ID NO: |
|---|---|---|
| ALD01 | mA(ps)fA(ps)mUfGmUfUmUfUmCfCmUfGmCfUmGfAmC(ps)fG(ps)mG | 25 |
|  | fC(ps)mC(ps)fGmUfCmAfGmCfAmGfGmAfAmAfAmCfA(ps)mU(ps)fU | 26 |
| ALD32 | mA(ps)fA(ps)mUfGmUfUmUfUmCfCmUfGmCfUmGfAmC(ps)fG(ps)mG | 65 |
|  | mC(ps)mC(ps)fGmUfCmAfGmCfAmGfGmAfAmAfAmCfA(ps)mU(ps)fU | 66 |
| ALD33 | mA(ps)fA(ps)mUfGmUfUmUfUmCfCmUfGmCfUmGfAmC(ps)fG(ps)mG | 67 |
|  | fC(ps)mC(ps)mGmUfCmAfGmCfAmGfGmAfAmAfAmCfA(ps)mU(ps)fU | 68 |
| ALD34 | mA(ps)fA(ps)mUfGmUfUmUfUmCfCmUfGmCfUmGfAmC(ps)fG(ps)mG | 69 |
|  | fC(ps)mC(ps)fGmUmCmAfGmCfAmGfGmAfAmAfAmCfA(ps)mU(ps)fU | 70 |
| ALD35 | mA(ps)fA(ps)mUfGmUfUmUfUmCfCmUfGmCfUmGfAmC(ps)fG(ps)mG | 71 |
|  | fC(ps)mC(ps)fGmUfCmAmGmCfAmGfGmAfAmAfAmCfA(ps)mU(ps)fU | 72 |
| ALD36 | mA(ps)fA(ps)mUfGmUfUmUfUmCfCmUfGmCfUmGfAmC(ps)fG(ps)mG | 73 |
|  | fC(ps)mC(ps)fGmUfCmAfGmCmAmGfGmAfAmAfAmCfA(ps)mU(ps)fU | 74 |
| ALD37 | mA(ps)fA(ps)mUfGmUfUmUfUmCfCmUfGmCfUmGfAmC(ps)fG(ps)mG | 75 |
|  | fC(ps)mC(ps)fGmUfCmAfGmCfAmGmGmAfAmAfAmCfA(ps)mU(ps)fU | 76 |
| ALD38 | mA(ps)fA(ps)mUfGmUfUmUfUmCfCmUfGmCfUmGfAmC(ps)fG(ps)mG | 77 |
|  | fC(ps)mC(ps)fGmUfCmAfGmCfAmGfGmAmAmAfAmCfA(ps)mU(ps)fU | 78 |
| ALD39 | mA(ps)fA(ps)mUfGmUfUmUfUmCfCmUfGmCfUmGfAmC(ps)fG(ps)mG | 79 |
|  | fC(ps)mC(ps)fGmUfCmAfGmCfAmGfGmAfAmAmAmCfA(ps)mU(ps)fU | 80 |
| ALD40 | mA(ps)fA(ps)mUfGmUfUmUfUmCfCmUfGmCfUmGfAmC(ps)fG(ps)mG | 81 |
|  | fC(ps)mC(ps)fGmUfCmAfGmCfAmGfGmAfAmAfAmCmA(ps)mU(ps)fU | 82 |
| ALD41 | mA(ps)fA(ps)mUfGmUfUmUfUmCfCmUfGmCfUmGfAmC(ps)fG(ps)mG | 83 |
|  | fC(ps)mC(ps)fGmUfCmAfGmCfAmGfGmAfAmAfAmCfA(ps)mU(ps)mU | 84 |
| ALD42 | mA(ps)fA(ps)mUfGmUfUmUfUmCfCmUfGmCfUmGfAmC(ps)fG(ps)mG | 85 |
|  | fC(ps)fC(ps)fGmUfCmAfGmCfAmGfGmAfAmAfAmCfA(ps)mU(ps)fU | 86 |
| ALD43 | mA(ps)fA(ps)mUfGmUfUmUfUmCfCmUfGmCfUmGfAmC(ps)fG(ps)mG | 87 |
|  | fC(ps)mC(ps)fGfUfCmAfGmCfAmGfGmAfAmAfAmCfA(ps)mU(ps)fU | 88 |
| ALD44 | mA(ps)fA(ps)mUfGmUfUmUfUmCfCmUfGmCfUmGfAmC(ps)fG(ps)mG | 89 |
|  | fC(ps)mC(ps)fGmUfCfAfGmCfAmGfGmAfAmAfAmCfA(ps)mU(ps)fU | 90 |
| ALD45 | mA(ps)fA(ps)mUfGmUfUmUfUmCfCmUfGmCfUmGfAmC(ps)fG(ps)mG | 91 |
|  | fC(ps)mC(ps)fGmUfCmAfGfCfAmGfGmAfAmAfAmCfA(ps)mU(ps)fU | 92 |
| ALD46 | mA(ps)fA(ps)mUfGmUfUmUfUmCfCmUfGmCfUmGfAmC(ps)fG(ps)mG | 93 |
|  | fC(ps)mC(ps)fGmUfCmAfGmCfAfGfGmAfAmAfAmCfA(ps)mU(ps)fU | 94 |
| ALD47 | mA(ps)fA(ps)mUfGmUfUmUfUmCfCmUfGmCfUmGfAmC(ps)fG(ps)mG | 95 |
|  | fC(ps)mC(ps)fGmUfCmAfGmCfAmGfGfAfAmAfAmCfA(ps)mU(ps)fU | 96 |
| ALD48 | mA(ps)fA(ps)mUfGmUfUmUfUmCfCmUfGmCfUmGfAmC(ps)fG(ps)mG | 97 |
|  | fC(ps)mC(ps)fGmUfCmAfGmCfAmGfGmAfAfAfAmCfA(ps)mU(ps)fU | 98 |
| ALD49 | mA(ps)fA(ps)mUfGmUfUmUfUmCfCmUfGmCfUmGfAmC(ps)fG(ps)mG | 99 |
|  | fC(ps)mC(ps)fGmUfCmAfGmCfAmGfGmAfAmAfAfCfA(ps)mU(ps)fU | 100 |
| ALD50 | mA(ps)fA(ps)mUfGmUfUmUfUmCfCmUfGmCfUmGfAmC(ps)fG(ps)mG | 101 |
|  | fC(ps)mC(ps)fGmUfCmAfGmCfAmGfGmAfAmAfAmCfA(ps)fU(ps)fU | 102 | mA, mU, mC, mG – 2'-OMe RNA
fA, fU, fC, fG – 2'-F RNA
(ps) – phosphorothioate

Fig 7a

| Duplex ID | sequence and chemistry<br>top: first strand, bottom: second strand, both 5'-3' | SEQ ID NO: |
|---|---|---|
| ALD58 | mAfAmUfGmUfUmUfUmCfCmUfGmCfUmGfAmCfGmG | 103 |
|  | fCmCfGmUfCmAfGmCfAmGfGmAfAmAfAmCfAmUfU | 104 |
| ALD59 | mAfAmUmGmUmUmUmUmCmCmUmGmCmUmGmAmCmGmG | 105 |
|  | fCmCfGmUfCmAfGmCfAmGfGmAfAmAfAmCfAmUfU | 106 |
| ALD60 | mAmAmUmGmUmUmUmUmCmCmUmGmCfUmGmAmCmGmG | 107 |
|  | fCmCfGmUfCmAfGmCfAmGfGmAfAmAfAmCfAmUfU | 108 |
| ALD61 | mAfAmUmGmUmUmUmUmCmCmUmGmCfUmGmAmCmGmG | 109 |
|  | fCmCfGmUfCmAfGmCfAmGfGmAfAmAfAmCfAmUfU | 110 |
| ALD62 | mAfAmUfGmUfUmUfUmCfCmUfGmCfUmGfAmCfGmG | 111 |
|  | mCmCmGmUmCmAfGmCmAmGmGmAmAmAmAmCmAmUmU | 112 |
| ALD63 | mAfAmUfGmUfUmUfUmCfCmUfGmCfUmGfAmCfGmG | 113 |
|  | mCmCmGmUmCmAmGmCfAmGmGmAmAmAmAmCmAmUmU | 114 |
| ALD64 | mAfAmUfGmUfUmUfUmCfCmUfGmCfUmGfAmCfGmG | 115 |
|  | mCmCmGmUmCmAfGmCfAmGmGmAmAmAmAmCmAmUmU | 116 | mA, mU, mC, mG – 2'-OMe RNA
fA, fU, fC, fG – 2'-F RNA
(ps) – phosphorothioate

Fig 7b

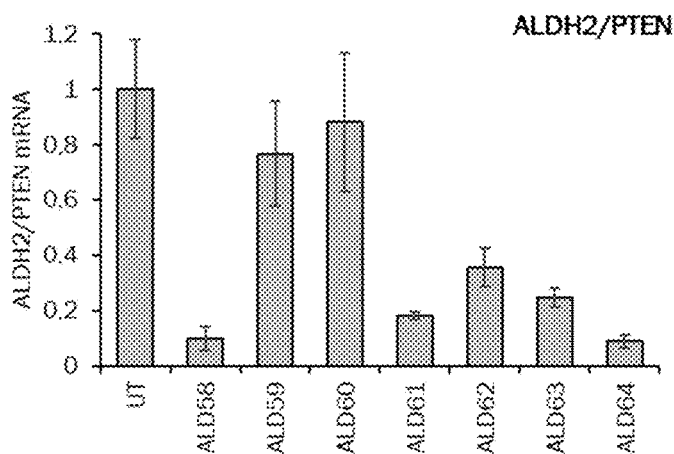

Figure 8a

| Duplex ID | sequence and chemistry<br>top: first strand, bottom: second strand, both 5'-3' | SEQ ID NO: |
|---|---|---|
| ALD72 | mAfUmGfUmAfGmCfCmGfAmGfGmAfUmCfUmUfCmU | 117 |
| | fAmGfAmAfGmAfUmCfCmUfCmGfGmCfUmAfCmAfU | 118 |
| ALD73 | mAfUmGmUmAmGmCmCmGmAmGmGmAmUmCmUmUmCmU | 119 |
| | fAmGfAmAfGmAfUmCfCmUfCmGfGmCfUmAfCmAfU | 120 |
| ALD74 | mAmUmGmUmAmGmCmCmGmAmGmGmAfUmCmUmUmCmU | 121 |
| | fAmGfAmAfGmAfUmCfCmUfCmGfGmCfUmAfCmAfU | 122 |
| ALD75 | mAfUmGmUmAmGmCmCmGmAmGmGmAfUmCmUmUmCmU | 123 |
| | fAmGfAmAfGmAfUmCfCmUfCmGfGmCfUmAfCmAfU | 124 |
| ALD76 | mAfUmGfUmAfGmCfCmGfAmGfGmAfUmCfUmUfCmU | 125 |
| | mAmGmAmAmGmAfUmCmCmUmCmGmGmCmUmAmCmAmU | 126 |
| ALD77 | mAfUmGfUmAfGmCfCmGfAmGfGmAfUmCfUmUfCmU | 127 |
| | mAmGmAmAmGmAmUmCfCmUmCmGmGmCmUmAmCmAmU | 128 |
| ALD78 | mAfUmGfUmAfGmCfCmGfAmGfGmAfUmCfUmUfCmU | 129 |
| | mAmGmAmAmGmAfUmCfCmUmCmGmGmCmUmAmCmAmU | 130 | mA, mU, mC, mG – 2'-OMe RNA
fA, fU, fC, fG – 2'-F RNA
(ps) – phosphorothioate

Figure 8b

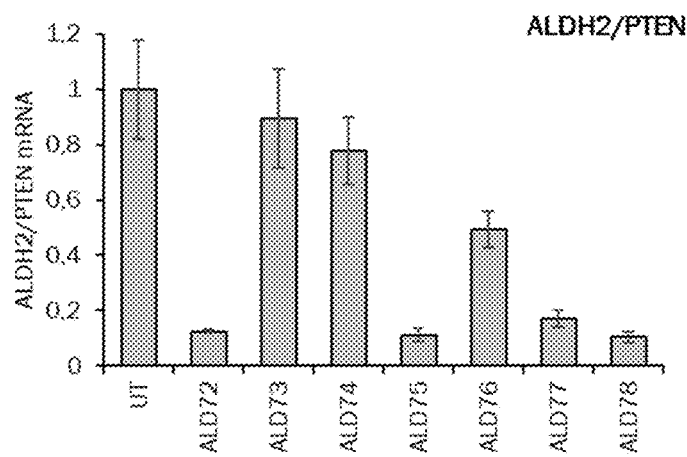

Figure 9a

| Duplex ID | sequence and chemistry<br>top: first strand, bottom: second strand, both 5'-3' | SEQ ID NO: |
|---|---|---|
| DGT01 | mUfUmAfAmAfUmAfAmCfCmCfAmCfAmGfAmCfAmC | 131 |
| | fGmUfGmUfCmUfGmUfGmGfGmUfUmAfUmUfUmAfA | 132 |
| DGT02 | mUfUmAmAmAmUmAmAmCmCmCmAmCmAmGmAmCmAmC | 133 |
| | fGmUfGmUfCmUfGmUfGmGfGmUfUmAfUmUfUmAfA | 134 |
| DGT03 | mUmUmAmAmAmUmAmAmCmCmCmAmCfAmGmAmCmAmC | 135 |
| | fGmUfGmUfCmUfGmUfGmGfGmUfUmAfUmUfUmAfA | 136 |
| DGT04 | mUfUmAmAmAmUmAmAmCmCmCmAmCfAmGmAmCmAmC | 137 |
| | fGmUfGmUfCmUfGmUfGmGfGmUfUmAfUmUfUmAfA | 138 |
| DGT05 | mUfUmAfAmAfUmAfAmCfCmCfAmCfAmGfAmCfAmC | 139 |
| | mGmUmGmUmCmUfGmUmGmGmGmUmUmAmUmUmUmAmA | 140 |
| DGT06 | mUfUmAfAmAfUmAfAmCfCmCfAmCfAmGfAmCfAmC | 141 |
| | mGmUmGmUmCmUfGmUfGmGmGmUmUmAmUmUmUmAmA | 142 |
| DGT07 | mUfUmAfAmAfUmAfAmCfCmCfAmCfAmGfAmCfAmC | 143 |
| | mGmUmGmUmCmUfGmUfGmGmGmUmUmAmUmUmUmAmA | 144 | mA, mU, mC, mG – 2'-OMe RNA
fA, fU, fC, fG – 2'-F RNA
(ps) – phosphorothioate

Figure 9b

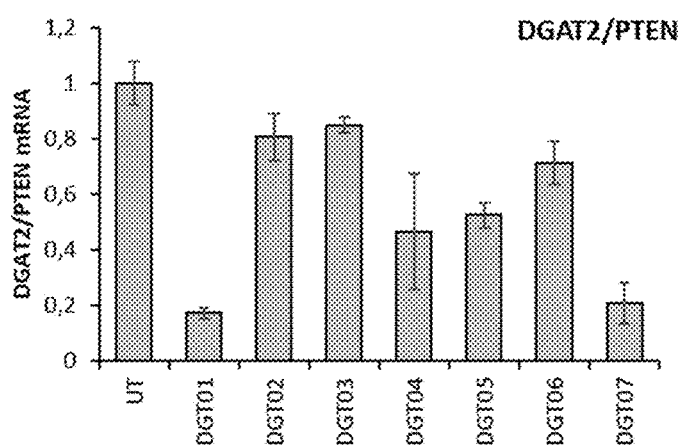

Figure 10a Modification with DNA: sequences

| Duplex ID | sequence and chemistry<br>top: first strand, bottom: second strand, both 5'-3' | SEQ ID NO: |
|---|---|---|
| TMP01 | mAfAmCfCmAfGmAfAmGfAmAfGmCfAmGfGmUfGmA | 145 |
| | fUmCfAmCfCmUfGmCfUmUfCmUfUmCfUmGfGmUfU | 146 |
| TMP93 | mAfAmCmCmAmGmAmAmGmAmAmGmCmAmGmGmUmGmA | 147 |
| | fUmCfAmCfCmUfGmCfUmUfCmUfUmCfUmGfGmUfU | 148 |
| TMP94 | mAmAmCmCmAmGmAmAmGmAmAmGmCfAmGmGmUmGmA | 149 |
| | fUmCfAmCfCmUfGmCfUmUfCmUfUmCfUmGfGmUfU | 150 |
| TMP97 | mAfAmCfCmAfGmAfAmGfAmAfGmCfAmGfGmUfGmA | 151 |
| | mUmCmAmCmCmUfGmCmUmUmCmUmUmCmUmGmGmUmU | 152 |
| TMP98 | mAfAmCfCmAfGmAfAmGfAmAfGmCfAmGfGmUfGmA | 153 |
| | mUmCmAmCmCmUmGmCfUmUmCmUmUmCmUmGmGmUmU | 154 |
| TMP112 | mA[A]mCmCmAmGmAmAmGmAmAmGmCfAmGmGmUmGmA | 155 |
| | fUmCfAmCfCmUfGmCfUmUfCmUfUmCfUmGfGmUfU | 156 |
| TMP113 | mAfAmCmCmAmGmAmAmGmAmAmGmC[A]mGmGmUmGmA | 157 |
| | fUmCfAmCfCmUfGmCfUmUfCmUfUmCfUmGfGmUfU | 158 |
| TMP116 | mAfAmCfCmAfGmAfAmGfAmAfGmCfAmGfGmUfGmA | 159 |
| | mUmCmAmCmCmU[G]mCfUmUmCmUmUmCmUmGmGmUmU | 160 |
| TMP117 | mAfAmCfCmAfGmAfAmGfAmAfGmCfAmGfGmUfGmA | 161 |
| | mUmCmAmCmCmUfGmC[U]mUmCmUmUmCmUmGmGmUmU | 162 | mA, mU, mC, mG – 2'-OMe RNA
fA, fU, fC, fG – 2'-F RNA
[A], [U], [C], [G] - 2'-H (DNA)

Figure 10b

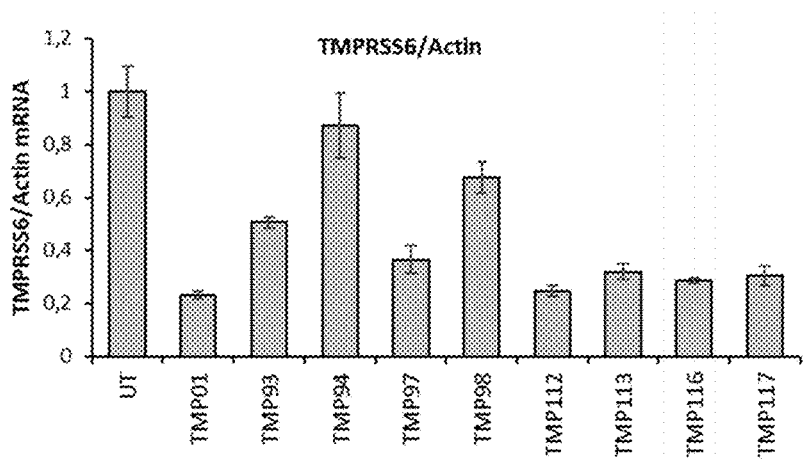

Figure 11a Modification with LNA: sequences

| Duplex ID | sequence and chemistry<br>top: first strand, bottom: second strand, both 5'-3' | SEQ ID NO: |
|---|---|---|
| TMP01 | mAfAmCfCmAfGmAfAmGfAmAfGmCfAmGfGmUfGmA | 145 |
|  | fUmCfAmCfCmUfGmCfUmUfCmUfUmCfUmGfGmUfU | 146 |
| TMP93 | mAfAmCmCmAmGmAmAmGmAmAmGmCmAmGmGmUmGmA | 147 |
|  | fUmCfAmCfCmUfGmCfUmUfCmUfUmCfUmGfGmUfU | 148 |
| TMP94 | mAmAmCmCmAmGmAmAmGmAmAmGmCfAmGmGmUmGmA | 149 |
|  | fUmCfAmCfCmUfGmCfUmUfCmUfUmCfUmGfGmUfU | 150 |
| TMP97 | mAfAmCfCmAfGmAfAmGfAmAfGmCfAmGfGmUfGmA | 151 |
|  | mUmCmAmCmCmUfGmCmUmUmCmUmUmCmUmGmGmUmU | 152 |
| TMP98 | mAfAmCfCmAfGmAfAmGfAmAfGmCfAmGfGmUfGmA | 153 |
|  | mUmCmAmCmCmUmGmCfUmUmCmUmUmCmUmGmGmUmU | 154 |
| TMP110 | mA{A}mCmCmAmGmAmAmGmAmAmGmCfAmGmGmUmGmA | 163 |
|  | fUmCfAmCfCmUfGmCfUmUfCmUfUmCfUmGfGmUfU | 164 |
| TMP111 | mAfAmCmCmAmGmAmAmGmAmAmGmC{A}mGmGmUmGmA | 165 |
|  | fUmCfAmCfCmUfGmCfUmUfCmUfUmCfUmGfGmUfU | 166 |
| TMP114 | mAfAmCfCmAfGmAfAmGfAmAfGmCfAmGfGmUfGmA | 167 |
|  | mUmCmAmCmCmU{G}mCfUmUmCmUmUmCmUmGmGmUmU | 168 |
| TMP115 | mAfAmCfCmAfGmAfAmGfAmAfGmCfAmGfGmUfGmA | 169 |
|  | mUmCmAmCmCmUfGmC{U}mUmCmUmUmCmUmGmGmUmU | 170 | mA, mU, mC, mG – 2'-OMe RNA
fA, fU, fC, fG – 2'-F RNA
{A}, {U}, {C}, {G} - LNA

Fig 11b

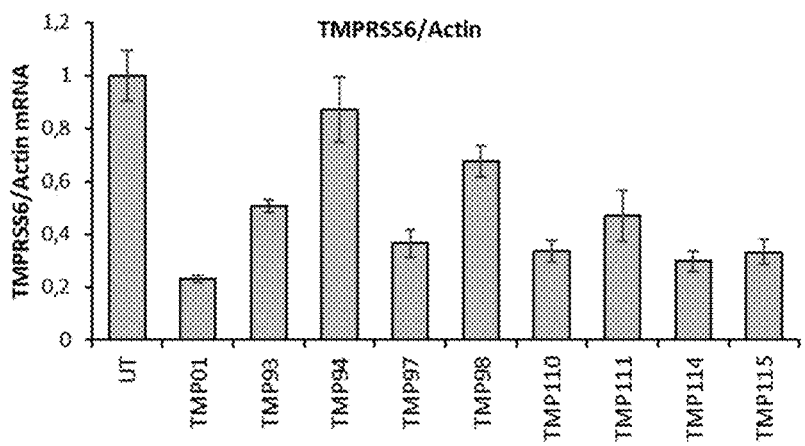

Figure 12B:
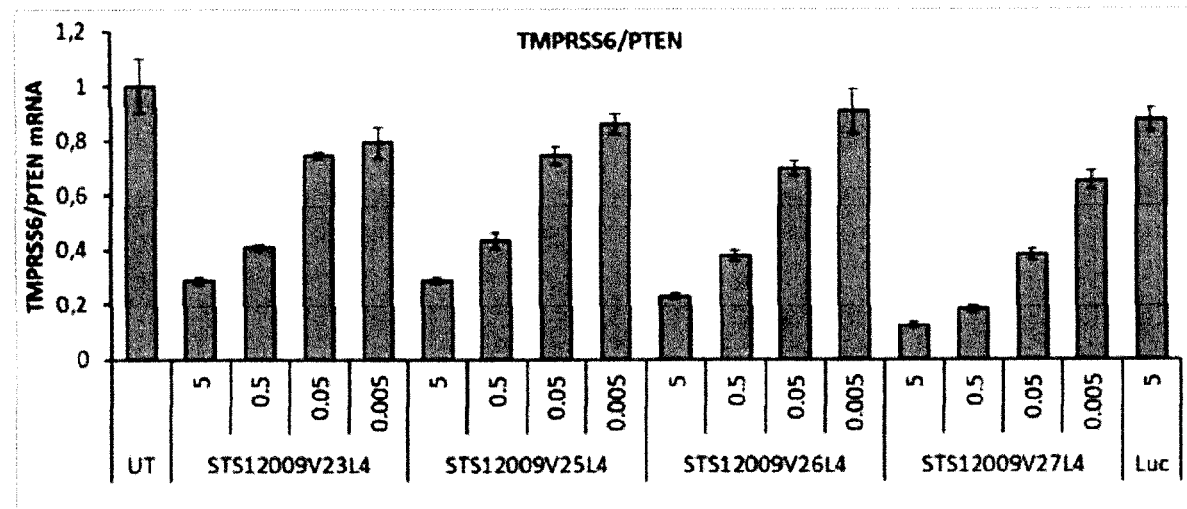
Figure 12C:
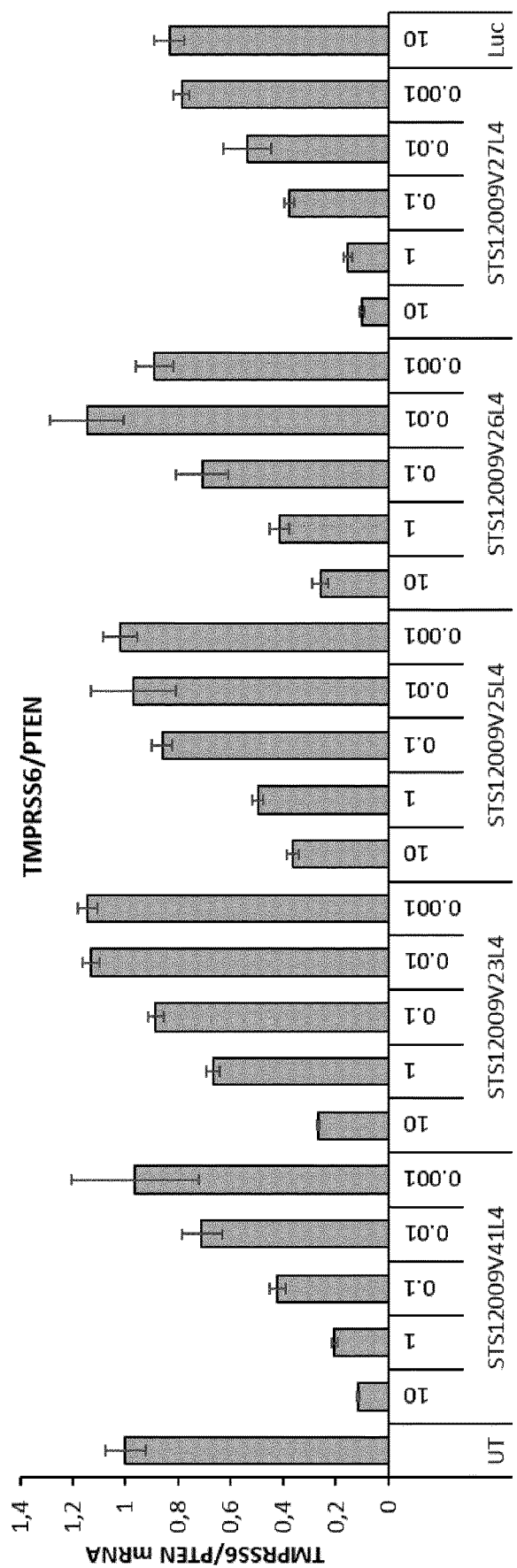
Figure 12D:
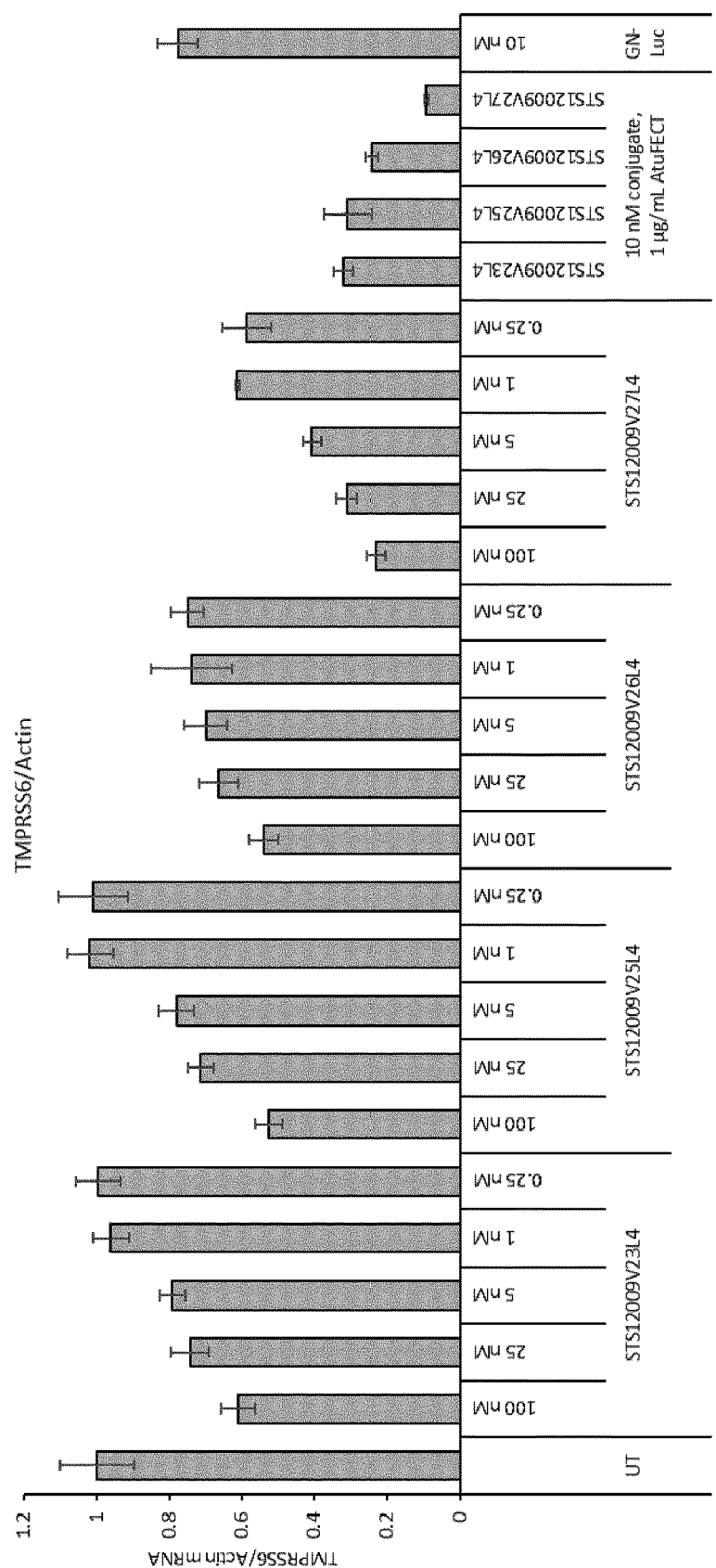

Fig 12a GalNAc-siRNA conjugates with 2'-OMe at B7 and B9

| Duplex ID | sequence and chemistry (top: first strand, bottom: second strand, both 5'-3') | SEQ ID NO: |
|---|---|---|
| STS12009V23L4 | mA(ps)fA(ps)mCmCmAmGmAmAmGmAmAfGmCfAmGmGmU(ps)mG(ps)mA<br>GalNAc-<br>mUmCmAmCmCmUmGmCmUmUmCmUmUmCmUmGmG(ps)mU(ps)mU | 171<br>172 |
| STS12009V25L4 | mA(ps)fA(ps)mCmCmAmGmAmAmGmAmAfGmCfAmGmGmU(ps)mG(ps)mA<br>GalNAc-<br>mUmCmAmCmCmUmGmCfUmUmCmUmUmCmUmGmG(ps)mU(ps)mU | 173<br>174 |
| STS12009V26L4 | mA(ps)fA(ps)mCmCmAmGmAmAmGmAmAfGmCfAmGmGmU(ps)mG(ps)mA<br>GalNAc-<br>mUmCmAmCmCmUfGmCmUmUmCmUmUmCmUmGmG(ps)mU(ps)mU | 175<br>176 |
| STS12009V27L4 | mA(ps)fA(ps)mCmCmAmGmAmAmGmAmAfGmCfAmGmGmU(ps)mG(ps)mA<br>GalNAc-<br>mUmCmAmCmCmUfGfCfUmUmCmUmUmCmUmGmG(ps)mU(ps)mU | 177<br>178 |
| STS12009V41L4 | mA(ps)fA(ps)mCmCmAmGmAmAmGmAmAfGmCfAmGmGmU(ps)mG(ps)mA<br>GalNAc-fUmCfAmCfCmUfGmCfUmUfCmUfUmCfUmGfG(ps)mU(ps)fU | 179<br>180 | mA, mU, mC, mG – 2'-OMe RNA
fA, fU, fC, fG – 2'-F RNA
(ps) – phosphorothioate
GalNAc - [ST23 (ps)]3 ST41 (ps)

Figure 13a Tolerance for DNA at more than one position

| Duplex ID | sequence and chemistry (top: first strand, bottom: second strand, both 5'-3') | SEQ ID NO: |
|---|---|---|
| TMP70 | mA(ps)fA(ps)mCfCmAfGmAfAmGfAmAfGmCfAmGfGmU(ps)fG(ps)mA | 181 |
| | fU(ps)mC(ps)fAmCfCmUfGmCfUmUfCmUfUmCfUmGfG(ps)mU(ps)fU | 182 |
| TMP119 | mA(ps)fA(ps)mCfCmAfGmAfAmGfAmAfGmCfAmGfGmU(ps)fG(ps)mA | 183 |
| | mU(ps)mC(ps)mAmCmCmUfGfCfUmUmCmUmUmCmUmGmG(ps)mU(ps)mU | 184 |
| TMP120 | mA(ps)fA(ps)mCmCmAmGmAmAmGmAmAmGmCfAmGmGmU(ps)mG(ps)mA | 185 |
| | mU(ps)mC(ps)mAmCmCmUfGfCfUmUmCmUmUmCmUmGmG(ps)mU(ps)mU | 186 |
| TMP121 | mA(ps)fA(ps)mCfCmAfGmAfAmGfAmAfGmCfAmGfGmU(ps)fG(ps)mA | 187 |
| | mU(ps)mC(ps)mAmCmCmU[G][C][T]mUmCmUmUmCmUmGmG(ps)mU(ps)mU | 188 |
| TMP122 | mA(ps)fA(ps)mCfCmAfGmAfAmGfAmAfGmCfAmGfGmU(ps)fG(ps)mA | 189 |
| | mU(ps)mC(ps)mAmCmCmU[G]mC[T]mUmCmUmUmCmUmGmG(ps)mU(ps)mU | 190 |
| TMP123 | mA(ps)fA(ps)mCmCmAmGmAmAmGmAmAmGmCfAmGmGmU(ps)mG(ps)mA | 191 |
| | mU(ps)mC(ps)mAmCmCmU[G][C][T]mUmCmUmUmCmUmGmG(ps)mU(ps)mU | 192 |
| TMP124 | mA(ps)[A](ps)mCmCmAmGmAmAmGmAmAmGmC[A]mGmGmU(ps)mG(ps)mA | 193 |
| | mU(ps)mC(ps)mAmCmCmU[G][C][T]mUmCmUmUmCmUmGmG(ps)mU(ps)mU | 194 |
| TMP125 | mA(ps)[A](ps)mCmCmAmGmAmAmGmAmAmGmCfAmGmGmU(ps)mG(ps)mA | 195 |
| | mU(ps)mC(ps)mAmCmCmU[G][C][T]mUmCmUmUmCmUmGmG(ps)mU(ps)mU | 196 |
| TMP126 | mA(ps)[A](ps)mCmCmAmGmAmAmGmAmAmGmCAmGmGmU(ps)mG(ps)mA | 197 |
| | mU(ps)mC(ps)mAmCmCmU[G][C][T]mUmCmUmUmCmUmGmG(ps)mU(ps)mU | 198 |

A, U, C, G – RNA
mA, mU, mC, mG – 2'-OMe RNA
fA, fU, fC, fG – 2'-F RNA
[A], [T], [C], [G] - 2'-H (DNA)
(ps) – phosphorothioate

Fig 13b

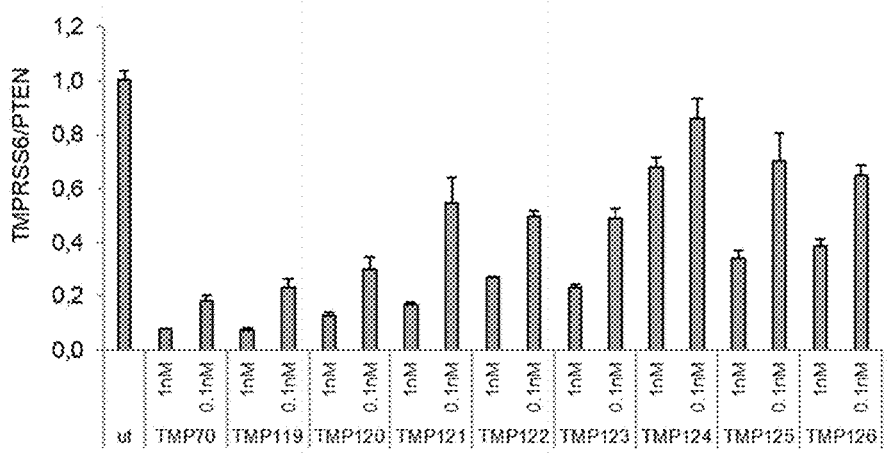

Figure 14A

| Duplex ID | sequence and chemistry<br>top: first strand, bottom: second strand, both 5'-3' | SEQ ID NO: |
|---|---|---|
| ALD58 | mAfAmUfGmUfUmUfUmCfCmUfGmCfUmGfAmCfGmG | 103 |
| | fCmCfGmUfCmAfGmCfAmGfGmAfAmAfAmCfAmUfU | 104 |
| ALD61 | mAfAmUmGmUmUmUmUmCmCmUmGmCfUmGmAmCmGmG | 109 |
| | fCmCfGmUfCmAfGmCfAmGfGmAfAmAfAmCfAmUfU | 110 |
| ALD90 | mA[A]mUmGmUmUmUmUmCmCmUmGmCfUmGmAmCmGmG | 314 |
| | fCmCfGmUfCmAfGmCfAmGfGmAfAmAfAmCfAmUfU | 315 |
| ALD91 | mAfAmUmGmUmUmUmUmCmCmUmGmC[T]mGmAmCmGmG | 199 |
| | fCmCfGmUfCmAfGmCfAmGfGmAfAmAfAmCfAmUfU | 200 |
| ALD92 | mA[A]mUmGmUmUmUmUmCmCmUmGmC[T]mGmAmCmGmG | 201 |
| | fCmCfGmUfCmAfGmCfAmGfGmAfAmAfAmCfAmUfU | 202 |
| ALD93 | mAfAmUfGmUfUmUfUmCfCmUfGmCfUmGfAmCfGmG | 203 |
| | mCmCmGmUmCmAfGmCfAmGmGmAmAmAmAmCmAmUmU | 204 |
| ALD94 | mAfAmUfGmUfUmUfUmCfCmUfGmCfUmGfAmCfGmG | 205 |
| | mCmCmGmUmCmA[G]mCfAmGmGmAmAmAmAmCmAmUmU | 206 |
| ALD95 | mAfAmUfGmUfUmUfUmCfCmUfGmCfUmGfAmCfGmG | 207 |
| | mCmCmGmUmCmAfGmC[A]mGmGmAmAmAmAmCmAmUmU | 208 |
| ALD96 | mAfAmUfGmUfUmUfUmCfCmUfGmCfUmGfAmCfGmG | 209 |
| | mCmCmGmUmCmA[G]mC[A]mGmGmAmAmAmAmCmAmUmU | 210 |
| ALD97 | mAfAmUfGmUfUmUfUmCfCmUfGmCfUmGfAmCfGmG | 211 |
| | mCmCmGmUmCmAfGfCfAmGmGmAmAmAmAmCmAmUmU | 212 |
| ALD98 | mAfAmUfGmUfUmUfUmCfCmUfGmCfUmGfAmCfGmG | 213 |
| | mCmCmGmUmCmA[G][C][A]mGmGmAmAmAmAmCmAmUmU | 214 | mA, mU, mC, mG – 2'-OMe RNA
fA, fU, fC, fG – 2'-F RNA
[A], [T], [C], [G] - DNA

Figure 14b

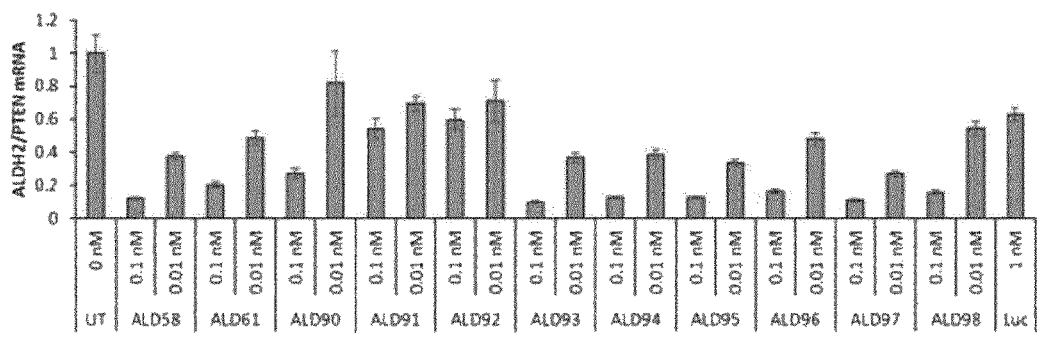

Figure 15a

| Duplex ID | sequence and chemistry top: first strand, bottom: second strand, both 5'-3' | SEQ ID NO: |
|---|---|---|
| ALD72 | mAfUmGfUmAfGmCfCmGfAmGfGmAfUmCfUmUfCmU | 117 |
| | fAmGfAmAfGmAfUmCfCmUfCmGfGmCfUmAfCmAfU | 118 |
| ALD75 | mAfUmGmUmAmGmCmCmGmAmGmGmAfUmCmUmUmCmU | 123 |
| | fAmGfAmAfGmAfUmCfCmUfCmGfGmCfUmAfCmAfU | 124 |
| ALD99 | mA[T]mGmUmAmGmCmCmGmAmGmGmAfUmCmUmUmCmU | 215 |
| | fAmGfAmAfGmAfUmCfCmUfCmGfGmCfUmAfCmAfU | 216 |
| ALD100 | mAfUmGmUmAmGmCmCmGmAmGmGmA[T]mCmUmUmCmU | 217 |
| | fAmGfAmAfGmAfUmCfCmUfCmGfGmCfUmAfCmAfU | 218 |
| ALD101 | mA[T]mGmUmAmGmCmCmGmAmGmGmA[T]mCmUmUmCmU | 219 |
| | fAmGfAmAfGmAfUmCfCmUfCmGfGmCfUmAfCmAfU | 220 |
| ALD102 | mAfUmGfUmAfGmCfCmGfAmGfGmAfUmCfUmUfCmU | 221 |
| | mAmGmAmAmGmAfUmCfCmUmCmGmGmCmUmAmCmAmU | 222 |
| ALD103 | mAfUmGfUmAfGmCfCmGfAmGfGmAfUmCfUmUfCmU | 223 |
| | mAmGmAmAmGmA[T]mCfCmUmCmGmGmCmUmAmCmAmU | 224 |
| ALD104 | mAfUmGfUmAfGmCfCmGfAmGfGmAfUmCfUmUfCmU | 225 |
| | mAmGmAmAmGmAfUmC[C]mUmCmGmGmCmUmAmCmAmU | 226 |
| ALD105 | mAfUmGfUmAfGmCfCmGfAmGfGmAfUmCfUmUfCmU | 227 |
| | mAmGmAmAmGmA[T]mC[C]mUmCmGmGmCmUmAmCmAmU | 228 |
| ALD106 | mAfUmGfUmAfGmCfCmGfAmGfGmAfUmCfUmUfCmU | 229 |
| | mAmGmAmAmGmAfUfCfCmUmCmGmGmCmUmAmCmAmU | 230 |
| ALD107 | mAfUmGfUmAfGmCfCmGfAmGfGmAfUmCfUmUfCmU | 231 |
| | mAmGmAmAmGmA[T][C][C]mUmCmGmGmCmUmAmCmAmU | 232 | mA, mU, mC, mG – 2'-OMe RNA
fA, fU, fC, fG – 2'-F RNA
[A], [T], [C], [G] - DNA

Figure 15b

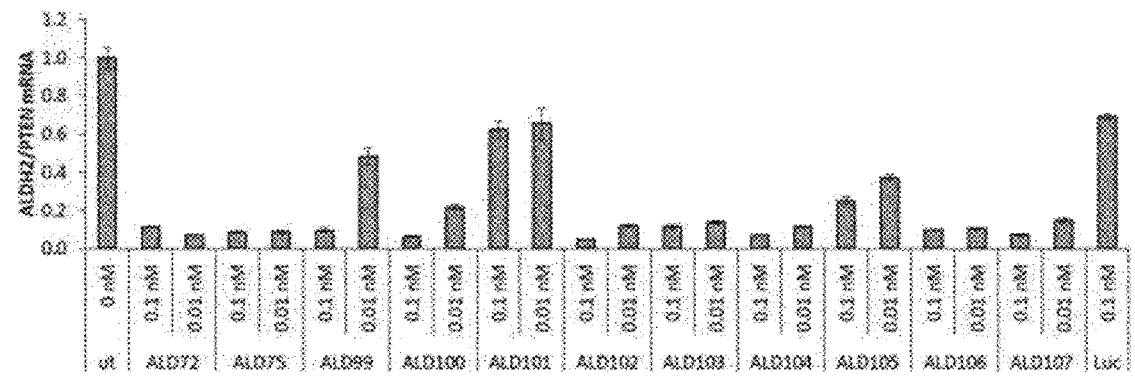

Figure 16a

| Duplex ID | sequence and chemistry<br>top: first strand, bottom: second strand, both 5'-3' | SEQ ID NO: |
|---|---|---|
| DGT01 | mUfUmAfAmAfUmAfAmCfCmCfAmCfAmGfAmCfAmC<br>fGmUfGmUfCmUfGmUfGmGfGmUfUmAfUmUfUmAfA | 131<br>132 |
| DGT04 | mUfUmAmAmUmAmAmCmCmCmAmCfAmGmAmCmAmC<br>fGmUfGmUfCmUfGmUfGmGfGmUfUmAfUmUfUmAfA | 137<br>138 |
| DGT11 | mU[T]mAmAmAmUmAmAmCmCmCmAmCfAmGmAmCmAmC<br>fGmUfGmUfCmUfGmUfGmGfGmUfUmAfUmUfUmAfA | 233<br>234 |
| DGT12 | mUfUmAmAmUmAmAmCmCmCmAmC[A]mGmAmCmAmC<br>fGmUfGmUfCmUfGmUfGmGfGmUfUmAfUmUfUmAfA | 235<br>236 |
| DGT13 | mU[T]mAmAmAmUmAmAmCmCmCmAmC[A]mGmAmCmAmC<br>fGmUfGmUfCmUfGmUfGmGfGmUfUmAfUmUfUmAfA | 237<br>238 |
| DGT14 | mUfUmAfAmAfUmAfAmCfCmCfAmCfAmGfAmCfAmC<br>mGmUmGmUmCmUfGmUfGmGmGmUmUmAmUmUmUmAmA | 239<br>240 |
| DGT15 | mUfUmAfAmAfUmAfAmCfCmCfAmCfAmGfAmCfAmC<br>mGmUmGmUmCmU[G]mUfGmGmGmUmUmAmUmUmUmAmA | 241<br>242 |
| DGT16 | mUfUmAfAmAfUmAfAmCfCmCfAmCfAmGfAmCfAmC<br>mGmUmGmUmCmUfGmU[G]mGmGmUmUmAmUmUmUmAmA | 243<br>244 |
| DGT17 | mUfUmAfAmAfUmAfAmCfCmCfAmCfAmGfAmCfAmC<br>mGmUmGmUmCmU[G]mU[G]mGmGmUmUmAmUmUmUmAmA | 245<br>246 |
| DGT18 | mUfUmAfAmAfUmAfAmCfCmCfAmCfAmGfAmCfAmC<br>mGmUmGmUmCmUfGfUfGmGmGmUmUmAmUmUmUmAmA | 247<br>248 |
| DGT19 | mUfUmAfAmAfUmAfAmCfCmCfAmCfAmGfAmCfAmC<br>mGmUmGmUmCmU[G][T][G]mGmGmUmUmAmUmUmUmAmA | 249<br>250 | mA, mU, mC, mG – 2'-OMe RNA
fA, fU, fC, fG – 2'-F RNA
[A], [T], [C], [G] - DNA

Figure 16b

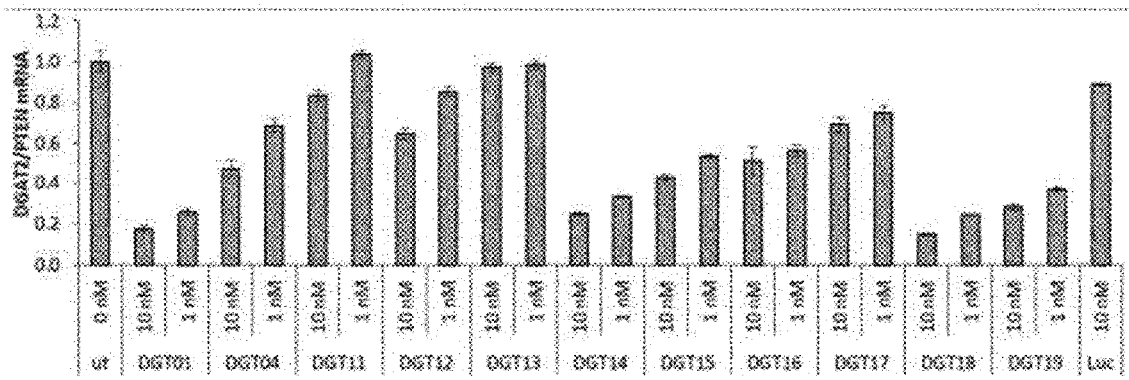

Figure 17a

| Duplex ID | sequence and chemistry<br>top: first strand, bottom: second strand, both 5'-3' | SEQ ID NO: |
|---|---|---|
| ALD108 | mA(ps)fU(ps)mGmUmAmGmCmCmGmAmGmGmAfUmCmUmU(ps)mC(ps)mU | 251 |
|  | mA(ps)mG(ps)mAmAmGmAfUmCfCmUmCmGmGmCmUmAmC(ps)mA(ps)mU | 252 |
| ALD115 | mA(ps)(MOE-U)(ps)mGmUmAmGmCmCmGmAmGmGmAfUmCmUmU(ps)mC(ps)mU | 253 |
|  | mA(ps)mG(ps)mAmAmGmAfUmCfCmUmCmGmGmCmUmAmC(ps)mA(ps)mU | 254 |
| ALD116 | mA(ps)fU(ps)mGmUmAmGmCmCmGmAmGmGmA(MOE-U)mCmUmU(ps)mC(ps)mU | 255 |
|  | mA(ps)mG(ps)mAmAmGmAfUmCfCmUmCmGmGmCmUmAmC(ps)mA(ps)mU | 256 |
| ALD117 | mA(ps)(MOE-U)(ps)mGmUmAmGmCmCmGmAmGmGmA(MOE-U)mCmUmU(ps)mC(ps)mU | 257 |
|  | mA(ps)mG(ps)mAmAmGmAfUmCfCmUmCmGmGmCmUmAmC(ps)mA(ps)mU | 258 |
| ALD118 | mA(ps)fU(ps)mGmUmAmGmCmCmGmAmGmGmAfUmCmUmU(ps)mC(ps)mU | 259 |
|  | mA(ps)mG(ps)mAmAmGmA(MOE-U)mCfCmUmCmGmGmCmUmAmC(ps)mA(ps)mU | 260 |
| ALD119 | mA(ps)fU(ps)mGmUmAmGmCmCmGmAmGmGmAfUmCmUmU(ps)mC(ps)mU | 261 |
|  | mA(ps)mG(ps)mAmAmGmAfUmC(MOE-C)mUmCmGmGmCmUmAmC(ps)mA(ps)mU | 262 |
| ALD120 | mA(ps)fU(ps)mGmUmAmGmCmCmGmAmGmGmAfUmCmUmU(ps)mC(ps)mU | 263 |
|  | mA(ps)mG(ps)mAmAmGmA(MOE-U)mC(MOE-C)mUmCmGmGmCmUmAmC(ps)mA(ps)mU | 264 | mA, mU, mC, mG – 2'-OMe RNA
fA, fU, fC, fG – 2'-F RNA
(ps) - phosphorothioate
(MOE-U), (MOE-C) - 2'-methoxyethyl RNA

Figure 17b

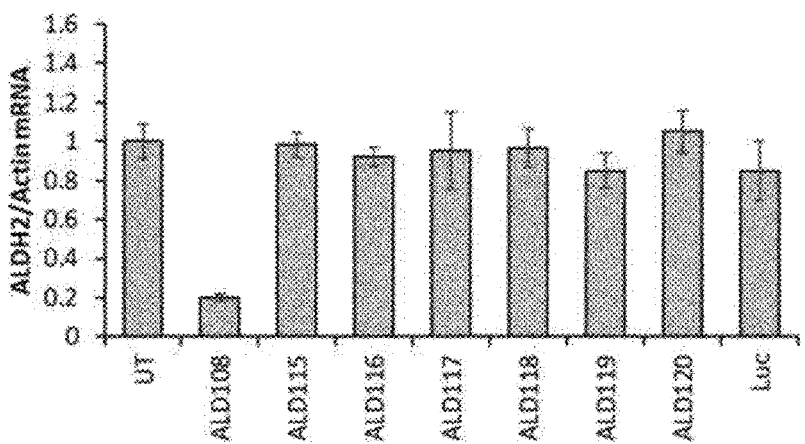

Figure 18a

| Duplex ID | | sequence and chemistry (top: first strand, bottom: second strand, both 5'-3') | SEQ ID NO: |
|---|---|---|---|
| GHR03 | GHR00A | mA(ps)fA(ps)mUfCmAfGmGfGmCfAmUfUmCfUmUfUmC(ps)fC(ps)mA | 279 |
|  | GHR00B | fU(ps)mG(ps)fGmAfAmAfGmAfAmUfGmCfCmCfUmGfA(ps)mU(ps)fU | 280 |
| GHR07 | GHR02A | mA(ps)mA(ps)mUfCmAfGmGfGmCfAmUfUmCfUmUfUmC(ps)fC(ps)mA | 281 |
|  | GHR00B | fU(ps)mG(ps)fGmAfAmAfGmAfAmUfGmCfCmCfUmGfA(ps)mU(ps)fU | 280 |
| GHR08 | GHR04A | mA(ps)fA(ps)mUmCmAfGmGfGmCfAmUfUmCfUmUfUmC(ps)fC(ps)mA | 282 |
|  | GHR00B | fU(ps)mG(ps)fGmAfAmAfGmAfAmUfGmCfCmCfUmGfA(ps)mU(ps)fU | 280 |
| GHR09 | GHR06A | mA(ps)fA(ps)mUfCmAmGmGfGmCfAmUfUmCfUmUfUmC(ps)fC(ps)mA | 283 |
|  | GHR00B | fU(ps)mG(ps)fGmAfAmAfGmAfAmUfGmCfCmCfUmGfA(ps)mU(ps)fU | 280 |
| GHR10 | GHR08A | mA(ps)fA(ps)mUfCmAfGmGmGmCfAmUfUmCfUmUfUmC(ps)fC(ps)mA | 284 |
|  | GHR00B | fU(ps)mG(ps)fGmAfAmAfGmAfAmUfGmCfCmCfUmGfA(ps)mU(ps)fU | 280 |
| GHR11 | GHR10A | mA(ps)fA(ps)mUfCmAfGmGfGmCmAmUfUmCfUmUfUmC(ps)fC(ps)mA | 285 |
|  | GHR00B | fU(ps)mG(ps)fGmAfAmAfGmAfAmUfGmCfCmCfUmGfA(ps)mU(ps)fU | 280 |
| GHR12 | GHR12A | mA(ps)fA(ps)mUfCmAfGmGfGmCfAmUmUmCfUmUfUmC(ps)fC(ps)mA | 286 |
|  | GHR00B | fU(ps)mG(ps)fGmAfAmAfGmAfAmUfGmCfCmCfUmGfA(ps)mU(ps)fU | 280 |
| GHR13 | GHR14A | mA(ps)fA(ps)mUfCmAfGmGfGmCfAmUfUmCmUmUfUmC(ps)fC(ps)mA | 287 |
|  | GHR00B | fU(ps)mG(ps)fGmAfAmAfGmAfAmUfGmCfCmCfUmGfA(ps)mU(ps)fU | 280 |
| GHR14 | GHR16A | mA(ps)fA(ps)mUfCmAfGmGfGmCfAmUfUmCfUmUmUmC(ps)fC(ps)mA | 288 |
|  | GHR00B | fU(ps)mG(ps)fGmAfAmAfGmAfAmUfGmCfCmCfUmGfA(ps)mU(ps)fU | 280 |
| GHR15 | GHR18A | mA(ps)fA(ps)mUfCmAfGmGfGmCfAmUfUmCfUmUfUmC(ps)mC(ps)mA | 289 |
|  | GHR00B | fU(ps)mG(ps)fGmAfAmAfGmAfAmUfGmCfCmCfUmGfA(ps)mU(ps)fU | 280 |
| GHR16 | GHR01A | fA(ps)fA(ps)mUfCmAfGmGfGmCfAmUfUmCfUmUfUmC(ps)fC(ps)mA | 290 |
|  | GHR00B | fU(ps)mG(ps)fGmAfAmAfGmAfAmUfGmCfCmCfUmGfA(ps)mU(ps)fU | 280 |
| GHR17 | GHR03A | mA(ps)fA(ps)fUfCmAfGmGfGmCfAmUfUmCfUmUfUmC(ps)fC(ps)mA | 291 |
|  | GHR00B | fU(ps)mG(ps)fGmAfAmAfGmAfAmUfGmCfCmCfUmGfA(ps)mU(ps)fU | 280 |
| GHR18 | GHR05A | mA(ps)fA(ps)mUfCfAfGmGfGmCfAmUfUmCfUmUfUmC(ps)fC(ps)mA | 292 |
|  | GHR00B | fU(ps)mG(ps)fGmAfAmAfGmAfAmUfGmCfCmCfUmGfA(ps)mU(ps)fU | 280 |
| GHR19 | GHR07A | mA(ps)fA(ps)mUfCmAfGfGfGmCfAmUfUmCfUmUfUmC(ps)fC(ps)mA | 293 |
|  | GHR00B | fU(ps)mG(ps)fGmAfAmAfGmAfAmUfGmCfCmCfUmGfA(ps)mU(ps)fU | 280 |
| GHR20 | GHR09A | mA(ps)fA(ps)mUfCmAfGmGfGfCfAmUfUmCfUmUfUmC(ps)fC(ps)mA | 294 |
|  | GHR00B | fU(ps)mG(ps)fGmAfAmAfGmAfAmUfGmCfCmCfUmGfA(ps)mU(ps)fU | 280 |
| GHR21 | GHR11A | mA(ps)fA(ps)mUfCmAfGmGfGmCfAfUfUmCfUmUfUmC(ps)fC(ps)mA | 295 |
|  | GHR00B | fU(ps)mG(ps)fGmAfAmAfGmAfAmUfGmCfCmCfUmGfA(ps)mU(ps)fU | 280 |
| GHR22 | GHR13A | mA(ps)fA(ps)mUfCmAfGmGfGmCfAmUfUfCfUmUfUmC(ps)fC(ps)mA | 296 |
|  | GHR00B | fU(ps)mG(ps)fGmAfAmAfGmAfAmUfGmCfCmCfUmGfA(ps)mU(ps)fU | 280 |
| GHR23 | GHR15A | mA(ps)fA(ps)mUfCmAfGmGfGmCfAmUfUmCfUfUfUmC(ps)fC(ps)mA | 297 |
|  | GHR00B | fU(ps)mG(ps)fGmAfAmAfGmAfAmUfGmCfCmCfUmGfA(ps)mU(ps)fU | 280 |
| GHR24 | GHR17A | mA(ps)fA(ps)mUfCmAfGmGfGmCfAmUfUmCfUmUfUfC(ps)fC(ps)mA | 298 |
|  | GHR00B | fU(ps)mG(ps)fGmAfAmAfGmAfAmUfGmCfCmCfUmGfA(ps)mU(ps)fU | 280 |
| GHR25 | GHR19A | mA(ps)fA(ps)mUfCmAfGmGfGmCfAmUfUmCfUmUfUmC(ps)fC(ps)fA | 299 |
|  | GHR00B | fU(ps)mG(ps)fGmAfAmAfGmAfAmUfGmCfCmCfUmGfA(ps)mU(ps)fU | 280 | mA, mU, mC, mG – 2'-OMe RNA
fA, fU, fC, fG – 2'-F RNA
(ps) - phosphorothioate

SEQUENCE LISTING

<160> NUMBER OF SEQ ID NOS: 319

<210> SEQ ID NO 1
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 1
augcaaaaua cacuucuac                                                    19

<210> SEQ ID NO 2
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 2
guagaagugu auuuugcau                                                    19

<210> SEQ ID NO 3
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 3
augcaaaaua cacuucuac                                                    19

<210> SEQ ID NO 4
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 4
guagaagugu auuuugcau                                                    19

```
<210> SEQ ID NO 5
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 5
augcaaaaua cacuucuac                                                19

<210> SEQ ID NO 6
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 6
guagaagugu auuuugcau                                                19

<210> SEQ ID NO 7
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 7
augcaaaaua cacuucuac                                                19

<210> SEQ ID NO 8
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 8
guagaagugu auuuugcau                                                19

<210> SEQ ID NO 9
<211> LENGTH: 19
<212> TYPE: RNA
```

<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
     table at the end of the description

<400> SEQUENCE: 9
augcaaaaua cacuucuac                                                    19

<210> SEQ ID NO 10
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
     table at the end of the description

<400> SEQUENCE: 10
guagaagugu auuuugcau                                                    19

<210> SEQ ID NO 11
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
     table at the end of the description

<400> SEQUENCE: 11
augcaaaaua cacuucuac                                                    19

<210> SEQ ID NO 12
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
     table at the end of the description

<400> SEQUENCE: 12
guagaagugu auuuugcau                                                    19

<210> SEQ ID NO 13
<211> LENGTH: 19
<212> TYPE: RNA
<213> ORGANISM: Artificial Sequence
<220> FEATURE:
<223> OTHER INFORMATION: siRNA

```
<220> FEATURE:
<221> NAME/KEY: MISC_FEATURE
<223> OTHER INFORMATION: modified_base, modified as per summary sequence
      table at the end of the description

<400> SEQUENCE: 13
augcaaaaua cacuucuac                                                    19

<210> SEQ ID NO 14
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 14
guagaagugu auuuugcau                                                    19

<210> SEQ ID NO 15
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 15
augcaaaaua cacuucuac                                                    19

<210> SEQ ID NO 16
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 16
guagaagugu auuuugcau                                                    19

<210> SEQ ID NO 17
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
```

-continued table at the end of the description

<400> SEQUENCE: 17
augcaaaaua cacuucuac                                                          19

<210> SEQ ID NO 18
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 18
guagaagugu auuuugcau                                                          19

<210> SEQ ID NO 19
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 19
augcaaaaua cacuucuac                                                          19

<210> SEQ ID NO 20
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 20
guagaagugu auuuugcau                                                          19

<210> SEQ ID NO 21
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 21
auugauagaa ccaucuuca                                                    19

<210> SEQ ID NO 22
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 22
ugaagauggu ucuaucaau                                                    19

<210> SEQ ID NO 23
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 23
auugauagaa ccaucuuca                                                    19

<210> SEQ ID NO 24
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 24
ugaagauggu ucuaucaau                                                    19

<210> SEQ ID NO 25
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 25
aauguuuucc ugcugacgg                                                    19

```
<210> SEQ ID NO 26
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 26
ccgucagcag gaaaacauu                                                 19

<210> SEQ ID NO 27
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 27
aauguuuucc ugcugacgg                                                 19

<210> SEQ ID NO 28
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 28
ccgucagcag gaaaacauu                                                 19

<210> SEQ ID NO 29
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 29
aauguuuucc ugcugacgg                                                 19

<210> SEQ ID NO 30
<211> LENGTH: 19
```

```
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 30
ccgucagcag gaaaacauu                                                       19

<210> SEQ ID NO 31
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 31
aauguuuucc ugcugacgg                                                       19

<210> SEQ ID NO 32
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 32
ccgucagcag gaaaacauu                                                       19

<210> SEQ ID NO 33
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 33
aauguuuucc ugcugacgg                                                       19

<210> SEQ ID NO 34
<211> LENGTH: 19
<212> TYPE: RNA
<213> ORGANISM: Artificial Sequence
<220> FEATURE:
```

```
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 34
ccgucagcag gaaaacauu                                                19

<210> SEQ ID NO 35
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 35
aauguuuucc ugcugacgg                                                19

<210> SEQ ID NO 36
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 36
ccgucagcag gaaaacauu                                                19

<210> SEQ ID NO 37
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 37
aauguuuucc ugcugacgg                                                19

<210> SEQ ID NO 38
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
```

```
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 38
ccgucagcag gaaaacauu                                                     19

<210> SEQ ID NO 39
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 39
aauguuuucc ugcugacgg                                                     19

<210> SEQ ID NO 40
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 40
ccgucagcag gaaaacauu                                                     19

<210> SEQ ID NO 41
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 41
aauguuuucc ugcugacgg                                                     19

<210> SEQ ID NO 42
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
```

```
<223> OTHER INFORMATION: modified_base, modified as per summary sequence
      table at the end of the description

<400> SEQUENCE: 42
ccgucagcag gaaaacauu                                                19

<210> SEQ ID NO 43
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 43
aauguuuucc ugcugacgg                                                19

<210> SEQ ID NO 44
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 44
ccgucagcag gaaaacauu                                                19

<210> SEQ ID NO 45
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 45
aauguuuucc ugcugacgg                                                19

<210> SEQ ID NO 46
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description
```

```
<400> SEQUENCE: 46
ccgucagcag gaaaacauu                                                19

<210> SEQ ID NO 47
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 47
aauguuuccc ugcugacgg                                                19

<210> SEQ ID NO 48
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 48
ccgucagcag gaaaacauu                                                19

<210> SEQ ID NO 49
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 49
aauguuuccc ugcugacgg                                                19

<210> SEQ ID NO 50
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 50
ccgucagcag gaaaacauu                                                19
```

```
<210> SEQ ID NO 51
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 51 aauguuucc ugcugacgg                                                    19

<210> SEQ ID NO 52
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 52
ccgucagcag gaaaacauu                                                   19

<210> SEQ ID NO 53
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 53 aauguuucc ugcugacgg                                                    19

<210> SEQ ID NO 54
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 54
ccgucagcag gaaaacauu                                                   19

<210> SEQ ID NO 55
```

```
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 55
aauguuuucc ugcugacgg                                                19

<210> SEQ ID NO 56
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 56
ccgucagcag gaaaacauu                                                19

<210> SEQ ID NO 57
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 57
aauguuuucc ugcugacgg                                                19

<210> SEQ ID NO 58
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 58
ccgucagcag gaaaacauu                                                19

<210> SEQ ID NO 59
<211> LENGTH: 19
<212> TYPE: RNA
<213> ORGANISM: Artificial Sequence
```

```
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 59
aauguuuucc ugcugacgg                                                19

<210> SEQ ID NO 60
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 60
ccgucagcag gaaaacauu                                                19

<210> SEQ ID NO 61
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 61
aauguuuucc ugcugacgg                                                19

<210> SEQ ID NO 62
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 62
ccgucagcag gaaaacauu                                                19

<210> SEQ ID NO 63
<211> LENGTH: 19
<212> TYPE: RNA
<213> ORGANISM: Artificial Sequence
<220> FEATURE:
<223> OTHER INFORMATION: Synthetic
<220> FEATURE:
```

```
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 63
aauguuuucc ugcugacgg                                                  19

<210> SEQ ID NO 64
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 64
ccgucagcag gaaaacauu                                                  19

<210> SEQ ID NO 65
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 65
aauguuuucc ugcugacgg                                                  19

<210> SEQ ID NO 66
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 66
ccgucagcag gaaaacauu                                                  19

<210> SEQ ID NO 67
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
```

<221> NAME/KEY: MISC_FEATURE
<223> OTHER INFORMATION: modified_base, modified as per summary sequence
     table at the end of the description

<400> SEQUENCE: 67
aauguuuucc ugcugacgg                                                    19

<210> SEQ ID NO 68
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
     table at the end of the description

<400> SEQUENCE: 68
ccgucagcag gaaaacauu                                                    19

<210> SEQ ID NO 69
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
     table at the end of the description

<400> SEQUENCE: 69
aauguuuucc ugcugacgg                                                    19

<210> SEQ ID NO 70
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
     table at the end of the description

<400> SEQUENCE: 70
ccgucagcag gaaaacauu                                                    19

<210> SEQ ID NO 71
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
     table at the end of the description

```
<400> SEQUENCE: 71
aauguuuucc ugcugacgg                                                 19

<210> SEQ ID NO 72
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 72
ccgucagcag gaaaacauu                                                 19

<210> SEQ ID NO 73
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 73
aauguuuucc ugcugacgg                                                 19

<210> SEQ ID NO 74
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 74
ccgucagcag gaaaacauu                                                 19

<210> SEQ ID NO 75
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 75
aauguuuucc ugcugacgg                                                 19
```

```
<210> SEQ ID NO 76
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 76
ccgucagcag gaaaacauu                                                    19

<210> SEQ ID NO 77
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 77 aauguuucc ugcugacgg                                                     19

<210> SEQ ID NO 78
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 78
ccgucagcag gaaaacauu                                                    19

<210> SEQ ID NO 79
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 79 aauguuucc ugcugacgg                                                     19

<210> SEQ ID NO 80
<211> LENGTH: 19
<212> TYPE: RNA
```

```
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 80
ccgucagcag gaaaacauu                                                   19

<210> SEQ ID NO 81
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 81
aauguuuucc ugcugacgg                                                   19

<210> SEQ ID NO 82
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 82
ccgucagcag gaaaacauu                                                   19

<210> SEQ ID NO 83
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 83
aauguuuucc ugcugacgg                                                   19

<210> SEQ ID NO 84
<211> LENGTH: 19
<212> TYPE: RNA
<213> ORGANISM: Artificial Sequence
<220> FEATURE:
<223> OTHER INFORMATION: Synthetic
```

```
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 84
ccgucagcag gaaaacauu                                                    19

<210> SEQ ID NO 85
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 85
aauguuuucc ugcugacgg                                                    19

<210> SEQ ID NO 86
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 86
ccgucagcag gaaaacauu                                                    19

<210> SEQ ID NO 87
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 87
aauguuuucc ugcugacgg                                                    19

<210> SEQ ID NO 88
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
```

```
<220> FEATURE:
<221> NAME/KEY: MISC_FEATURE
<223> OTHER INFORMATION: modified_base, modified as per summary sequence
      table at the end of the description

<400> SEQUENCE: 88
ccgucagcag gaaaacauu                                                       19

<210> SEQ ID NO 89
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 89
aauguuuucc ugcugacgg                                                       19

<210> SEQ ID NO 90
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 90
ccgucagcag gaaaacauu                                                       19

<210> SEQ ID NO 91
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 91
aauguuuucc ugcugacgg                                                       19

<210> SEQ ID NO 92
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
``` table at the end of the description

<400> SEQUENCE: 92
ccgucagcag gaaaacauu                                                19

<210> SEQ ID NO 93
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 93 aauguuucc ugcugacgg                                                 19

<210> SEQ ID NO 94
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 94
ccgucagcag gaaaacauu                                                19

<210> SEQ ID NO 95
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 95 aauguuucc ugcugacgg                                                 19

<210> SEQ ID NO 96
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 96
ccgucagcag gaaaacauu                                                     19

<210> SEQ ID NO 97
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 97
aauguuuucc ugcugacgg                                                     19

<210> SEQ ID NO 98
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 98
ccgucagcag gaaaacauu                                                     19

<210> SEQ ID NO 99
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 99
aauguuuucc ugcugacgg                                                     19

<210> SEQ ID NO 100
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 100
ccgucagcag gaaaacauu                                                     19

-continued

```
<210> SEQ ID NO 101
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 101
aauguuuccc ugcugacgg                                              19

<210> SEQ ID NO 102
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 102
ccgucagcag gaaaacauu                                              19

<210> SEQ ID NO 103
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 103
aauguuuccc ugcugacgg                                              19

<210> SEQ ID NO 104
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 104
ccgucagcag gaaaacauu                                              19

<210> SEQ ID NO 105
<211> LENGTH: 19
```

```
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 105
aauguuuucc ugcugacgg                                               19

<210> SEQ ID NO 106
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 106
ccgucagcag gaaaacauu                                               19

<210> SEQ ID NO 107
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 107
aauguuuucc ugcugacgg                                               19

<210> SEQ ID NO 108
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 108
ccgucagcag gaaaacauu                                               19

<210> SEQ ID NO 109
<211> LENGTH: 19
<212> TYPE: RNA
<213> ORGANISM: Artificial Sequence
<220> FEATURE:
```

<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 109
aauguuuucc ugcugacgg                                                    19

<210> SEQ ID NO 110
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 110
ccgucagcag gaaaacauu                                                    19

<210> SEQ ID NO 111
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 111
aauguuuucc ugcugacgg                                                    19

<210> SEQ ID NO 112
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 112
ccgucagcag gaaaacauu                                                    19

<210> SEQ ID NO 113
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE

```
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 113
aauguuuucc ugcugacgg                                                 19

<210> SEQ ID NO 114
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 114
ccgucagcag gaaaacauu                                                 19

<210> SEQ ID NO 115
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 115
aauguuuucc ugcugacgg                                                 19

<210> SEQ ID NO 116
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 116
ccgucagcag gaaaacauu                                                 19

<210> SEQ ID NO 117
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
```

<223> OTHER INFORMATION: modified_base, modified as per summary sequence
      table at the end of the description

<400> SEQUENCE: 117
auguagccga ggaucuucu                                                      19

<210> SEQ ID NO 118
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 118
agaagauccu cggcuacau                                                      19

<210> SEQ ID NO 119
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 119
auguagccga ggaucuucu                                                      19

<210> SEQ ID NO 120
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 120
agaagauccu cggcuacau                                                      19

<210> SEQ ID NO 121
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

```
<400> SEQUENCE: 121
auguagccga ggaucuucu                                                      19

<210> SEQ ID NO 122
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 122
agaagauccu cggcuacau                                                      19

<210> SEQ ID NO 123
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 123
auguagccga ggaucuucu                                                      19

<210> SEQ ID NO 124
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 124
agaagauccu cggcuacau                                                      19

<210> SEQ ID NO 125
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 125
auguagccga ggaucuucu                                                      19
```

<210> SEQ ID NO 126
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 126
agaagauccu cggcuacau                                              19

<210> SEQ ID NO 127
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 127
auguagccga ggaucuucu                                              19

<210> SEQ ID NO 128
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 128
agaagauccu cggcuacau                                              19

<210> SEQ ID NO 129
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 129
auguagccga ggaucuucu                                              19

<210> SEQ ID NO 130

```
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 130
agaagauccu cggcuacau                                              19

<210> SEQ ID NO 131
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 131
uuaaauaacc cacagacac                                              19

<210> SEQ ID NO 132
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 132
gugucugugg guuauuuaa                                              19

<210> SEQ ID NO 133
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 133
uuaaauaacc cacagacac                                              19

<210> SEQ ID NO 134
<211> LENGTH: 19
<212> TYPE: RNA
<213> ORGANISM: Artificial Sequence
```

```
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 134
gugucugugg guuauuuaa                                                19

<210> SEQ ID NO 135
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 135
uuaaauaacc cacagacac                                                19

<210> SEQ ID NO 136
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 136
gugucugugg guuauuuaa                                                19

<210> SEQ ID NO 137
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 137
uuaaauaacc cacagacac                                                19

<210> SEQ ID NO 138
<211> LENGTH: 19
<212> TYPE: RNA
<213> ORGANISM: Artificial Sequence
<220> FEATURE:
<223> OTHER INFORMATION: Synthetic
<220> FEATURE:
```

```
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 138
gugucugugg guuauuuaa                                                    19

<210> SEQ ID NO 139
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 139
uuaaauaacc cacagacac                                                    19

<210> SEQ ID NO 140
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 140
gugucugugg guuauuuaa                                                    19

<210> SEQ ID NO 141
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 141
uuaaauaacc cacagacac                                                    19

<210> SEQ ID NO 142
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
```

<221> NAME/KEY: MISC_FEATURE
<223> OTHER INFORMATION: modified_base, modified as per summary sequence
      table at the end of the description

<400> SEQUENCE: 142
gugucugugg guuauuuaa                                                19

<210> SEQ ID NO 143
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 143
uuaaauaacc cacagacac                                                19

<210> SEQ ID NO 144
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 144
gugucugugg guuauuuaa                                                19

<210> SEQ ID NO 145
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 145
aaccagaaga agcagguga                                                19

<210> SEQ ID NO 146
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 146
ucaccugcuu cuucugguu                                          19

<210> SEQ ID NO 147
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 147
aaccagaaga agcagguga                                          19

<210> SEQ ID NO 148
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 148
ucaccugcuu cuucugguu                                          19

<210> SEQ ID NO 149
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 149
aaccagaaga agcagguga                                          19

<210> SEQ ID NO 150
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 150
ucaccugcuu cuucugguu                                        19

<210> SEQ ID NO 151
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 151
aaccagaaga agcagguga                                        19

<210> SEQ ID NO 152
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 152
ucaccugcuu cuucugguu                                        19

<210> SEQ ID NO 153
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 153
aaccagaaga agcagguga                                        19

<210> SEQ ID NO 154
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 154
ucaccugcuu cuucugguu                                        19

```
<210> SEQ ID NO 155
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 155
aaccagaaga agcagguga                                                    19

<210> SEQ ID NO 156
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 156
ucaccugcuu cuucugguu                                                    19

<210> SEQ ID NO 157
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 157
aaccagaaga agcagguga                                                    19

<210> SEQ ID NO 158
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 158
ucaccugcuu cuucugguu                                                    19

<210> SEQ ID NO 159
<211> LENGTH: 19
<212> TYPE: RNA
```

```
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 159
aaccagaaga agcagguga                                              19

<210> SEQ ID NO 160
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 160
ucaccugcuu cuucugguu                                              19

<210> SEQ ID NO 161
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 161
aaccagaaga agcagguga                                              19

<210> SEQ ID NO 162
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 162
ucaccugcuu cuucugguu                                              19

<210> SEQ ID NO 163
<211> LENGTH: 19
<212> TYPE: RNA
<213> ORGANISM: Artificial Sequence
<220> FEATURE:
<223> OTHER INFORMATION: Synthetic
```

```
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 163
aaccagaaga agcagguga                                                19

<210> SEQ ID NO 164
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 164
ucaccugcuu cuucugguu                                                19

<210> SEQ ID NO 165
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 165
aaccagaaga agcagguga                                                19

<210> SEQ ID NO 166
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 166
ucaccugcuu cuucugguu                                                19

<210> SEQ ID NO 167
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
```

```
<220> FEATURE:
<221> NAME/KEY: MISC_FEATURE
<223> OTHER INFORMATION: modified_base, modified as per summary sequence
      table at the end of the description

<400> SEQUENCE: 167
aaccagaaga agcagguga                                                      19

<210> SEQ ID NO 168
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 168
ucaccugcuu cuucugguu                                                      19

<210> SEQ ID NO 169
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 169
aaccagaaga agcagguga                                                      19

<210> SEQ ID NO 170
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 170
ucaccugcuu cuucugguu                                                      19

<210> SEQ ID NO 171
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
``` table at the end of the description

<400> SEQUENCE: 171
aaccagaaga agcagguga                                                    19

<210> SEQ ID NO 172
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 172
ucaccugcuu cuucugguu                                                    19

<210> SEQ ID NO 173
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 173
aaccagaaga agcagguga                                                    19

<210> SEQ ID NO 174
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 174
ucaccugcuu cuucugguu                                                    19

<210> SEQ ID NO 175
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 175
aaccagaaga agcagguga                                                19

<210> SEQ ID NO 176
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 176
ucaccugcuu cuucugguu                                                19

<210> SEQ ID NO 177
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 177
aaccagaaga agcagguga                                                19

<210> SEQ ID NO 178
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 178
ucaccugcuu cuucugguu                                                19

<210> SEQ ID NO 179
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 179
aaccagaaga agcagguga                                                19

```
<210> SEQ ID NO 180
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 180
ucaccugcuu cuucugguu                                                19

<210> SEQ ID NO 181
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 181
aaccagaaga agcagguga                                                19

<210> SEQ ID NO 182
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 182
ucaccugcuu cuucugguu                                                19

<210> SEQ ID NO 183
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 183
aaccagaaga agcagguga                                                19

<210> SEQ ID NO 184
<211> LENGTH: 19
```

```
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 184
ucaccugcuu cuucugguu                                                        19

<210> SEQ ID NO 185
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 185
aaccagaaga agcagguga                                                        19

<210> SEQ ID NO 186
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 186
ucaccugcuu cuucugguu                                                        19

<210> SEQ ID NO 187
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 187
aaccagaaga agcagguga                                                        19

<210> SEQ ID NO 188
<211> LENGTH: 19
<212> TYPE: DNA
<213> ORGANISM: Artificial Sequence
<220> FEATURE:
```

```
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 188
ucaccugcuu cuucugguu                                               19

<210> SEQ ID NO 189
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 189
aaccagaaga agcagguga                                               19

<210> SEQ ID NO 190
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 190
ucaccugcuu cuucugguu                                               19

<210> SEQ ID NO 191
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 191
aaccagaaga agcagguga                                               19

<210> SEQ ID NO 192
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
```

```
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 192
ucaccugctu cuucugguu                                                    19

<210> SEQ ID NO 193
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 193
aaccagaaga agcagguga                                                    19

<210> SEQ ID NO 194
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 194
ucaccugctu cuucugguu                                                    19

<210> SEQ ID NO 195
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 195
aaccagaaga agcagguga                                                    19

<210> SEQ ID NO 196
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
```

<223> OTHER INFORMATION: modified_base, modified as per summary sequence
      table at the end of the description

<400> SEQUENCE: 196
ucaccugctu cuucugguu                                                    19

<210> SEQ ID NO 197
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 197
aaccagaaga agcagguga                                                    19

<210> SEQ ID NO 198
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 198
ucaccugctu cuucugguu                                                    19

<210> SEQ ID NO 199
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 199
aauguuuucc ugctgacgg                                                    19

<210> SEQ ID NO 200
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

```
<400> SEQUENCE: 200
ccgucagcag gaaaacauu                                                19

<210> SEQ ID NO 201
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 201
aauguuuucc ugctgacgg                                                19

<210> SEQ ID NO 202
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 202
ccgucagcag gaaaacauu                                                19

<210> SEQ ID NO 203
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 203
aauguuuucc ugcugacgg                                                19

<210> SEQ ID NO 204
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 204
ccgucagcag gaaaacauu                                                19
```

<210> SEQ ID NO 205
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 205 aauguuucc ugcugacgg                                                    19

<210> SEQ ID NO 206
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 206
ccgucagcag gaaaacauu                                                   19

<210> SEQ ID NO 207
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 207 aauguuucc ugcugacgg                                                    19

<210> SEQ ID NO 208
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 208
ccgucagcag gaaaacauu                                                   19

<210> SEQ ID NO 209

```
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 209
aauguuuucc ugcugacgg                                                19

<210> SEQ ID NO 210
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 210
ccgucagcag gaaaacauu                                                19

<210> SEQ ID NO 211
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 211
aauguuuucc ugcugacgg                                                19

<210> SEQ ID NO 212
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 212
ccgucagcag gaaaacauu                                                19

<210> SEQ ID NO 213
<211> LENGTH: 19
<212> TYPE: RNA
<213> ORGANISM: Artificial Sequence
```

-continued

```
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 213
aauguuuucc ugcugacgg                                                19

<210> SEQ ID NO 214
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 214
ccgucagcag gaaaacauu                                                19

<210> SEQ ID NO 215
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 215
auguagccga ggaucuucu                                                19

<210> SEQ ID NO 216
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 216
agaagauccu cggcuacau                                                19

<210> SEQ ID NO 217
<211> LENGTH: 19
<212> TYPE: DNA
<213> ORGANISM: Artificial Sequence
<220> FEATURE:
<223> OTHER INFORMATION: Synthetic
<220> FEATURE:
```

```
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 217
auguagccga ggaucuucu                                               19

<210> SEQ ID NO 218
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 218
agaagauccu cggcuacau                                               19

<210> SEQ ID NO 219
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 219
atguagccga ggatcuucu                                               19

<210> SEQ ID NO 220
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 220
agaagauccu cggcuacau                                               19

<210> SEQ ID NO 221
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
```

<221> NAME/KEY: MISC_FEATURE
<223> OTHER INFORMATION: modified_base, modified as per summary sequence
      table at the end of the description

<400> SEQUENCE: 221
auguagccga ggaucuucu                                              19

<210> SEQ ID NO 222
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 222
agaagauccu cggcuacau                                              19

<210> SEQ ID NO 223
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 223
auguagccga ggaucuucu                                              19

<210> SEQ ID NO 224
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 224
agaagatccu cggcuacau                                              19

<210> SEQ ID NO 225
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 225
auguagccga ggaucuucu                                                19

<210> SEQ ID NO 226
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 226
agaagauccu cggcuacau                                                19

<210> SEQ ID NO 227
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 227
auguagccga ggaucuucu                                                19

<210> SEQ ID NO 228
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 228
agaagauccu cggcuacau                                                19

<210> SEQ ID NO 229
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 229
auguagccga ggaucuucu                                         19

<210> SEQ ID NO 230
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 230
agaagauccu cggcuacau                                         19

<210> SEQ ID NO 231
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 231
auguagccga ggaucuucu                                         19

<210> SEQ ID NO 232
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 232
agaagatccu cggcuacau                                         19

<210> SEQ ID NO 233
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 233
utaaauaacc cacagacac                                         19

```
<210> SEQ ID NO 234
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 234
gugucugugg guuauuuaa                                                19

<210> SEQ ID NO 235
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 235
uuaaauaacc cacagacac                                                19

<210> SEQ ID NO 236
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 236
gugucugugg guuauuuaa                                                19

<210> SEQ ID NO 237
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 237
uuaaauaacc cacagacac                                                19

<210> SEQ ID NO 238
<211> LENGTH: 19
<212> TYPE: RNA
```

<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 238
gugucugugg guuauuuaa                                                    19

<210> SEQ ID NO 239
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 239
utaaauaacc cacagacac                                                    19

<210> SEQ ID NO 240
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 240
gugucugugg guuauuuaa                                                    19

<210> SEQ ID NO 241
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 241
uuaaauaacc cacagacac                                                    19

<210> SEQ ID NO 242
<211> LENGTH: 19
<212> TYPE: RNA
<213> ORGANISM: Artificial Sequence
<220> FEATURE:
<223> OTHER INFORMATION: Synthetic

```
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 242
gugucugugg guuauuuaa                                              19

<210> SEQ ID NO 243
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 243
uuaaauaacc cacagacac                                              19

<210> SEQ ID NO 244
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 244
gugucugugg guuauuuaa                                              19

<210> SEQ ID NO 245
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 245
uuaaauaacc cacagacac                                              19

<210> SEQ ID NO 246
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
```

```
<220> FEATURE:
<221> NAME/KEY: MISC_FEATURE
<223> OTHER INFORMATION: modified_base, modified as per summary sequence
      table at the end of the description

<400> SEQUENCE: 246
gugucugugg guuauuuaa                                                    19

<210> SEQ ID NO 247
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 247
uuaaauaacc cacagacac                                                    19

<210> SEQ ID NO 248
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 248
gugucugugg guuauuuaa                                                    19

<210> SEQ ID NO 249
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 249
uuaaauaacc cacagacac                                                    19

<210> SEQ ID NO 250
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: /note="combined DNA/RNA molecule" /note="siRNA"
<220> FEATURE:
<221> NAME/KEY: MISC_FEATURE
<223> OTHER INFORMATION: modified_base, modified as per summary sequence
``` table at the end of the description

<400> SEQUENCE: 250
gugucugtgg guuauuuaa                                            19

<210> SEQ ID NO 251
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 251
auguagccga ggaucuucu                                            19

<210> SEQ ID NO 252
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 252
agaagauccu cggcuacau                                            19

<210> SEQ ID NO 253
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 253
auguagccga ggaucuucu                                            19

<210> SEQ ID NO 254
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 254
agaagauccu cggcuacau						19

<210> SEQ ID NO 255
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 255
auguagccga ggaucuucu						19

<210> SEQ ID NO 256
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 256
agaagauccu cggcuacau						19

<210> SEQ ID NO 257
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 257
auguagccga ggaucuucu						19

<210> SEQ ID NO 258
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 258
agaagauccu cggcuacau						19

<210> SEQ ID NO 259
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 259
auguagccga ggaucuucu                                              19

<210> SEQ ID NO 260
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 260
agaagauccu cggcuacau                                              19

<210> SEQ ID NO 261
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 261
auguagccga ggaucuucu                                              19

<210> SEQ ID NO 262
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 262
agaagauccu cggcuacau                                              19

<210> SEQ ID NO 263
<211> LENGTH: 19

```
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 263
auguagccga ggaucuucu                                                19

<210> SEQ ID NO 264
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per summary sequence
      table at the end of the description

<400> SEQUENCE: 264
agaagauccu cggcuacau                                                19

<210> SEQ ID NO 265
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 265
augcaaaaua cacuucuac                                                19

<210> SEQ ID NO 266
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 266
guagaagugu auuuugcau                                                19

<210> SEQ ID NO 267
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 267
auugauagaa ccaucuuca                                                19
```

<210> SEQ ID NO 268
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 268
ugaagauggu ucuaucaau                    19

<210> SEQ ID NO 269
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 269
ccgucagcag gaaaacauu                    19

<210> SEQ ID NO 270
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 270
ccgucagcag gaaaacauu                    19

<210> SEQ ID NO 271
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 271
auguagccga ggaucuucu                    19

<210> SEQ ID NO 272
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 272
agaagauccu cggcuacau                    19

<210> SEQ ID NO 273
<211> LENGTH: 19

```
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 273
uuaaauaacc cacagacac                                                19

<210> SEQ ID NO 274
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 274
gugucugugg guuauuuaa                                                19

<210> SEQ ID NO 275
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 275
aaccagaaga agcagguga                                                19

<210> SEQ ID NO 276
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 276
ucaccugcuu cuucugguu                                                19

<210> SEQ ID NO 277
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 277
aaccagaaga agcagguga                                                19

<210> SEQ ID NO 278
<211> LENGTH: 19
<212> TYPE: RNA
<213> ORGANISM: Artificial Sequence
<220> FEATURE:
<223> OTHER INFORMATION: Synthetic
```

```
<220> FEATURE:
<221> NAME/KEY: MISC_FEATURE
<223> OTHER INFORMATION: siRNA

<400> SEQUENCE: 278
ucaccugcuu cuucugguu                                                 19

<210> SEQ ID NO 279
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR00a in Figure
      18a

<400> SEQUENCE: 279
aaucagggca uucuuucca                                                 19

<210> SEQ ID NO 280
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR00b in Figure
      18a

<400> SEQUENCE: 280
uggaaagaau gcccugauu                                                 19

<210> SEQ ID NO 281
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR02a in Figure
      18a

<400> SEQUENCE: 281
aaucagggca uucuuucca                                                 19

<210> SEQ ID NO 282
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR04a in Figure
      18a
```

-continued

<400> SEQUENCE: 282
aaucagggca uucuuucca                                                19

<210> SEQ ID NO 283
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR06a in Figure
      18a

<400> SEQUENCE: 283
aaucagggca uucuuucca                                                19

<210> SEQ ID NO 284
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR08a in Figure
      18a

<400> SEQUENCE: 284
aaucagggca uucuuucca                                                19

<210> SEQ ID NO 285
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR10a in Figure
      18a

<400> SEQUENCE: 285
aaucagggca uucuuucca                                                19

<210> SEQ ID NO 286
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR12a in Figure
      18a

<400> SEQUENCE: 286
aaucagggca uucuuucca                                                19

<210> SEQ ID NO 287
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR14a in Figure
      18a

<400> SEQUENCE: 287
aaucagggca uucuuucca                                                19

<210> SEQ ID NO 288
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR16a in Figure
      18a

<400> SEQUENCE: 288
aaucagggca uucuuucca                                                19

<210> SEQ ID NO 289
<211> LENGTH: 19
<212> TYPE: RNA
<213> ORGANISM: Artificial Sequence
<220> FEATURE:
<223> OTHER INFORMATION: modified_base, modified as per GHR18a in Figure
      18a
<220> FEATURE:
<221> NAME/KEY: MISC_FEATURE
<223> OTHER INFORMATION: siRNA

<400> SEQUENCE: 289
aaucagggca uucuuucca                                                19

<210> SEQ ID NO 290
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR01a in Figure
      18a

<400> SEQUENCE: 290
aaucagggca uucuuucca                                                19

<210> SEQ ID NO 291
<211> LENGTH: 19
<212> TYPE: RNA

-continued

```
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR03a in Figure
      18a

<400> SEQUENCE: 291
aaucagggca uucuuucca                                                19

<210> SEQ ID NO 292
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR05a in Figure
      18a

<400> SEQUENCE: 292
aaucagggca uucuuucca                                                19

<210> SEQ ID NO 293
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR07a in Figure
      18a

<400> SEQUENCE: 293
aaucagggca uucuuucca                                                19

<210> SEQ ID NO 294
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR09a in Figure
      18a

<400> SEQUENCE: 294
aaucagggca uucuuucca                                                19

<210> SEQ ID NO 295
<211> LENGTH: 19
<212> TYPE: RNA
<213> ORGANISM: Artificial Sequence
<220> FEATURE:
<223> OTHER INFORMATION: Synthetic
```

```
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR11a in Figure
      18a

<400> SEQUENCE: 295
aaucagggca uucuuucca                                                 19

<210> SEQ ID NO 296
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR13a in Figure
      18a

<400> SEQUENCE: 296
aaucagggca uucuuucca                                                 19

<210> SEQ ID NO 297
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR15a in Figure
      18a

<400> SEQUENCE: 297
aaucagggca uucuuucca                                                 19

<210> SEQ ID NO 298
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
<220> FEATURE:
<221> NAME/KEY: MISC_FEATURE
<223> OTHER INFORMATION: modified_base, modified as per GHR17a in Figure
      18a

<400> SEQUENCE: 298
aaucagggca uucuuucca                                                 19

<210> SEQ ID NO 299
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
```

```
<220> FEATURE:
<221> NAME/KEY: MISC_FEATURE
<223> OTHER INFORMATION: modified_base, modified as per GHR19a in Figure
      18a

<400> SEQUENCE: 299
aaucagggca uucuuucca                                                      19

<210> SEQ ID NO 300
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 300
aaucagggca uucuuucca                                                      19

<210> SEQ ID NO 301
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 301
uggaaagaau gcccugauu                                                      19

<210> SEQ ID NO 302
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 302
auggaauacu cuugguuac                                                      19

<210> SEQ ID NO 303
<211> LENGTH: 19
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 303
guaaccaaga guauuccau                                                      19

<210> SEQ ID NO 304
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA
```

```
<400> SEQUENCE: 304
ucuugguuac augaaauccc auc                                          23

<210> SEQ ID NO 305
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 305
ugggauuuca uguaaccaag a                                            21

<210> SEQ ID NO 306
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 306
uugaaguaaa ugguguuaac cag                                          23

<210> SEQ ID NO 307
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 307
gguuaacacc auuuacuuca a                                            21

<210> SEQ ID NO 308
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 308
uauuauaaaa auaucuugcu uuutt                                        25

<210> SEQ ID NO 309
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 309
aagcaagaua uuuuuauaau a                                            21
```

```
<210> SEQ ID NO 310
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 310
uaagaugaga cacucuuucu ggu                                              23

<210> SEQ ID NO 311
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 311
cagaaagagu gucucaucuu a                                                21

<210> SEQ ID NO 312
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: MISC_FEATURE
<223> OTHER INFORMATION: siRNA

<400> SEQUENCE: 312
acaaaagcaa aacaggucua gaa                                              23

<210> SEQ ID NO 313
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: siRNA

<400> SEQUENCE: 313
cuagaccugu uuugcuuuug u                                                21

<210> SEQ ID NO 314
<211> LENGTH: 19
<212> TYPE: RNA
<213> ORGANISM: Artificial Seuqence
<220> FEATURE:
<223> OTHER INFORMATION: Synthetic
<220> FEATURE:
<221> NAME/KEY: misc_feature
<223> OTHER INFORMATION: siRNA
<220> FEATURE:
<221> NAME/KEY: misc_feature
<223> OTHER INFORMATION: modified_base, modified as per summary sequence
      table at the end of the description

<400> SEQUENCE: 314
aauguuuucc ugcugacgg                                                   19
```

```
<210> SEQ ID NO 315
<211> LENGTH: 19
<212> TYPE: DNA
<213> ORGANISM: Artificial Seuqnce
<220> FEATURE:
<223> OTHER INFORMATION: Synthetic
<220> FEATURE:
<221> NAME/KEY: misc_feature
<223> OTHER INFORMATION: siRNA
<220> FEATURE:
<221> NAME/KEY: misc_feature
<223> OTHER INFORMATION: modified_base, modified as per summary sequence
      table at the end of the description

<400> SEQUENCE: 315
ccgucagcag gaaaacauu                                                    19

<210> SEQ ID NO 316
<211> LENGTH: 21
<212> TYPE: DNA
<213> ORGANISM: Artificial Sequence
<220> FEATURE:
<223> OTHER INFORMATION: Synthetic

<400> SEQUENCE: 316
auauaaaggu ccuacuuuca g                                                 21

<210> SEQ ID NO 317
<211> LENGTH: 23
<212> TYPE: DNA
<213> ORGANISM: Artificial Seuqence
<220> FEATURE:
<223> OTHER INFORMATION: Synthetic

<400> SEQUENCE: 317
accugaaagu aggaccuuua uau                                               23

<210> SEQ ID NO 318
<211> LENGTH: 21
<212> TYPE: DNA
<213> ORGANISM: Artificial Sequence
<220> FEATURE:
<223> OTHER INFORMATION: Synthetic

<400> SEQUENCE: 318
agaaccaaug uacuuuaggg u                                                 21

<210> SEQ ID NO 319
<211> LENGTH: 23
<212> TYPE: DNA
<213> ORGANISM: Artificial Sequence
<220> FEATURE:
<223> OTHER INFORMATION: Synthetic

<400> SEQUENCE: 319
cuacccuaaa guacauuggu ucu                                               23
```

PRODUCTS AND COMPOSITIONS

CROSS REFERENCE TO RELATED APPLICATIONS

This application is a 35 U.S.C. § 371 National Phase Entry Application of International Application No. PCT/EP2018/058766 filed Apr. 5, 2018, which designates the United States, and which claims benefit under 35 U.S.C. § 119(a) of Great Britain Application No. 1707203.4 filed May 5, 2017, Great Britain Application No. 1708397.3 filed May 25, 2017, European Application No. 17165129.2 filed Apr. 5, 2017, and European Application No. 17201352.6 filed Nov. 13, 2017, the contents of each of which are incorporated herein by reference in their entireties.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "55817_SubSeqlisting.txt", which was created on Sep. 28, 2020 and is 110,040 bytes in size. The subject matter of the Sequence Listing is incorporated herein in its entirety by reference.

The present invention relates to products and compositions and their uses. In particular the invention relates to nucleic acid products that interfere with gene expression or inhibits its expression and therapeutic uses such as for the treatment of diseases and disorders.

BACKGROUND

Double-stranded RNA (dsRNA) has been shown to block gene expression (Fire et al, 1998 and Elbashir et al, 2001) and this has been termed RNA interference (RNAi). Short dsRNAs direct gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. Interfering RNA (iRNA) such as nucleic acid, antisense RNA, and micro-RNA are oligonucleotides that prevent the formation of proteins by gene-silencing i.e. inhibiting gene translation of the protein. Gene-silencing agents are becoming increasingly important for therapeutic applications in medicine.

However, delivery of nucleic acids, such as RNA, to cells avoiding degradation by cellular nucleases, whilst maintaining efficacy and target specificity has proved challenging to those in the field of developing nucleic acid molecules for therapeutic use.

According to Watts and Corey in the Journal of Pathology (2012; Vol 226, p 365-379) there are algorithms that can be used to design nucleic acid but none is perfect. It may take various experimental methods to identify potent nucleic acid, as algorithms do not take into account factors such as tertiary structure or the involvement of RNA binding proteins. Therefore the discovery of a potent nucleic acid with minimal off-target effects is a complex process but necessary for the pharmaceutical development of these highly charged molecules to be synthesised economically, distributed to target tissues, enter cells and function within acceptable limits of toxicity. Thus, means for efficient delivery of oligonucleotides, in particular double stranded siRNAs, to cells in vivo is becoming increasingly important and requires specific targeting and substantial protection from the extracellular environment, particularly serum proteins. One method of achieving specific targeting is to conjugate a targeting moiety to the iRNA duplex agent. The targeting moiety helps in targeting the iRNA duplex agent to the required target site and there is a need to design appropriate targeting moieties for the desired receptor sites for the conjugated molecules to be taken up by the cells such as by endocytosis.

However, targeting ligands developed so far do not always translate to in vivo setting and there is a clear need for more efficacious receptor specific ligand conjugated iRNA duplex agents and methods for their preparation for the in vivo delivery of oligonucleotide therapeutics, nucleic acids and double stranded siRNAs.

Rather than a lipid delivery system alone, the present invention addresses the structure of the nucleic acid itself.

Accordingly, the present invention provides a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene, wherein said first strand includes a modified nucleotides or non-modified nucleotides at a plurality of positions in order to facilitate processing of the nucleic acid by RISC.

The present invention also relates to a nucleic acid capable of inhibiting the expression of a target gene, the nucleic acid comprising a first strand and a second strand, wherein the first stand and second strand are at least partially complementary with one another, wherein said first strand is at least partially complementary to RNA transcribed from a portion of said target gene; and wherein said first strand and/or said second strand include modified nucleotides.

The nucleotides at positions 2 and 14 from the 5' end of the first strand may be modified.

The nucleotides at positions 2 and 14 from the 5' end of the first strand may not be modified with a 2' O-methyl modification.

The nucleotides at positions 2 and 14 from the 5' end of the first strand may not be modified with a modification selected from the group consisting of 2'-O-(2-Methoxyethyl), 2'-O-allyl, 2'-O-DNP, 2'-CE, 2'-EA, 2'-AEM, 2'-APM and 2'-GE.

The nucleotides at positions 2 and 14 from the 5' end of the first strand may be modified with a modification selected from the group consisting of 2'F, 4'-S, 2'-FANA and UNA.

The nucleotides at positions 2 and 14 from the 5' end of the first strand may be unmodified.

The nucleotides at position 2 and 14 from the 5' end of the second strand may be modified with a 2' O-methyl modification or with a '—O-(2-Methoxyethyl) modification.

The first strand and the second strand may be separate strands

The nucleic acid may comprise a single strand that comprises the first strand and the second strand.

The first strand and/or said second strand may each be from 17-35 nucleotides in length and the at least one duplex region may be from 10-25 nucleotides in length. The duplex may comprise two separate strands or it may comprise a single strand which comprises the first strand and the second strand.

In one aspect the second strand may be as short as 11 nucleotides in length such as 11, 12, 13, 14, 15, 16, 17, 18, 19 nucleotides or more.

The nucleic acid may: a) be blunt ended at both ends; b) have an overhang at one end and a blunt end at the other; or c) have an overhang at both ends.

One or more nucleotides on the first and/or second strand may be modified, to form modified nucleotides. One or more of the odd numbered nucleotides of the first strand may be modified.

One or more of the even numbered nucleotides of the first strand may be modified by at least a second modification, wherein the at least second modification is different from the modification on the one or more add nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first strand odd numbered nucleotides. A plurality of odd numbered nucleotides on the second strand may be modified by a second modification, wherein the second modification is different from the modification of the first strand odd numbered nucleotides.

The second strand comprises adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with a second different modification.

The nucleic acid of the invention may have the modified nucleotides of the first strand shifted by at least one nucleotide relative to the unmodified or differently modified nucleotides of the second strand.

The modification and/or modifications may each and individually be selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-O-methyl and/or at least one modification may be 2'-F.

A nucleic acid of the invention may comprise a phosphorothioate linkage between the terminal one, two or three 3' nucleotides and/or one two or three 5' nucleotides of the first and/or the second strand. It may comprise two phosphorothioate linkages between each of the three terminal 3' and between each of the three terminal κ' nucleotides on the first strand, and two phosphorothioate linkages between the three terminal nucleotides of the 3' end of the second strand.

Such a nucleic acid may be conjugated to a ligand.

The invention further provides a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene wherein said first strand includes modified nucleotides or unmodified nucleotides at a plurality of positions in order to facilitate processing of the nucleic acid by RISC, and wherein the nucleotide sequence is conjugated to a ligand.

The ligand may comprise (i) one or more N-acetyl galactosamine (GalNac) moieties and derivatives thereof, and (ii) a linker, wherein the linker conjugates the GalNac moieties to a sequence as defined in any preceding aspects. The linker may be a bivalent or trivalent or tetravalent branched structure. The nucleotides may be modified as defined herein.

The ligand may comprise the formula I:

$$[S-X^1-P-X^2]_3\text{-}A\text{-}X^3- \qquad (I)$$

wherein:

S represents a saccharide, wherein the saccharide is N-acetyl galactosamine;

$X^1$ represents $C_3$-$C_6$ alkylene or $(-CH_2-CH_2-O)_m(-CH_2)_2-$ wherein m is 1, 2, or 3;

P is a phosphate or modified phosphate (preferably a thiophosphate);

$X^2$ is alkylene or an alkylene ether of the formula $(-CH_2)_n-O-CH_2-$ where n=1-6;

A is a branching unit;

$X^3$ represents a bridging unit;

wherein a nucleic acid according to the present invention is conjugated to $X^3$ via a phosphate or modified phosphate (preferably a thiophosphate).

The present invention therefore additionally provides a conjugated nucleic acid having one of the following structures

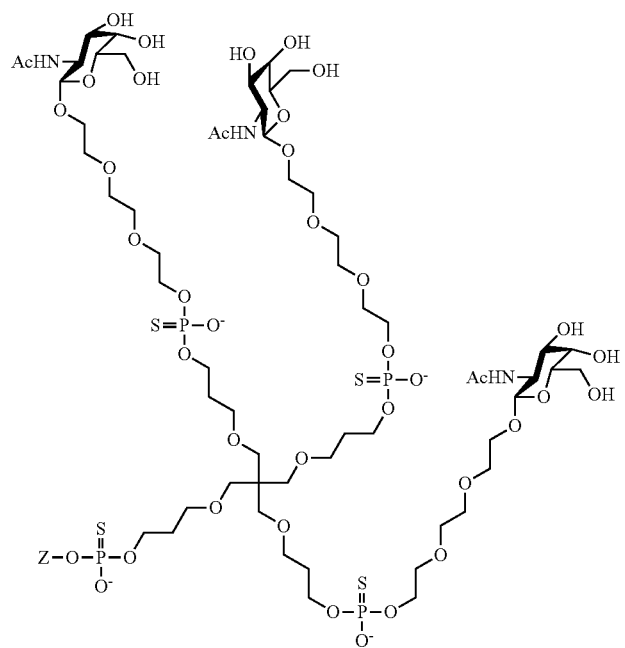
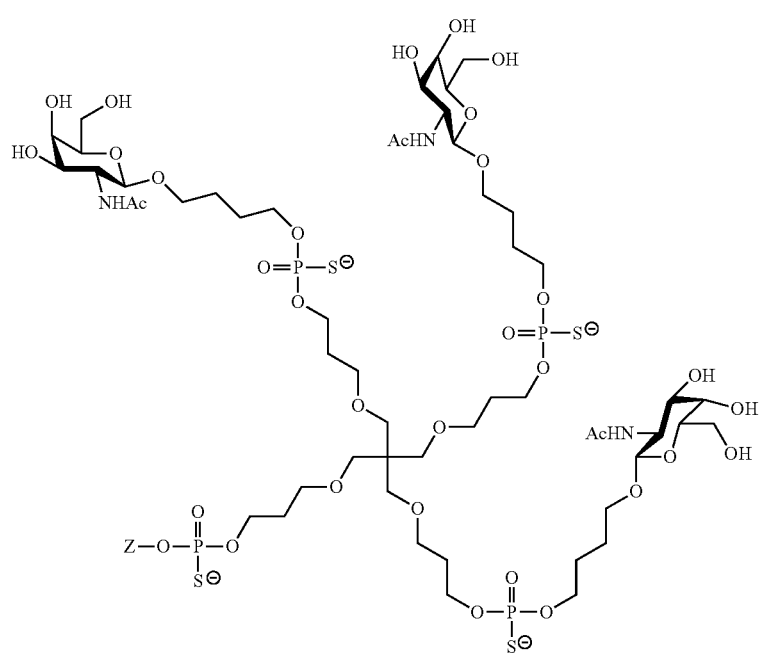

-continued
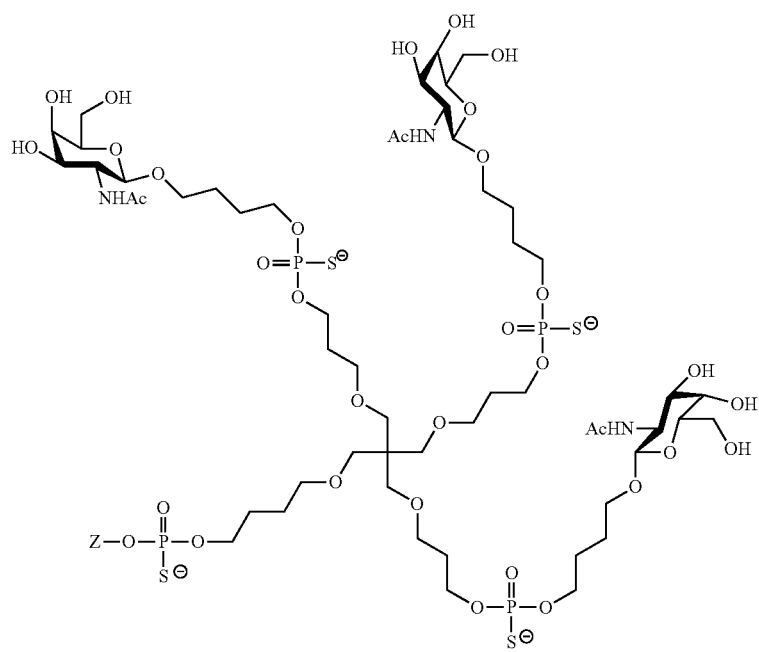
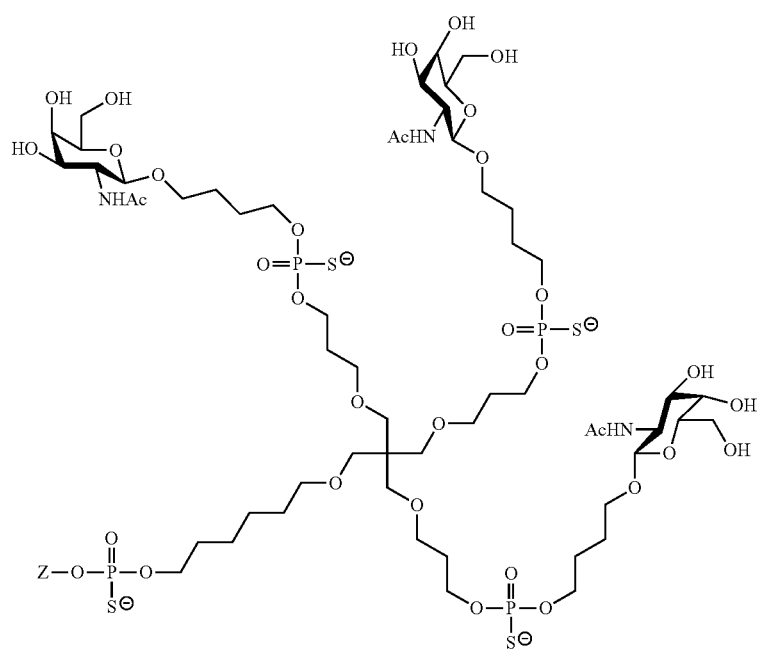

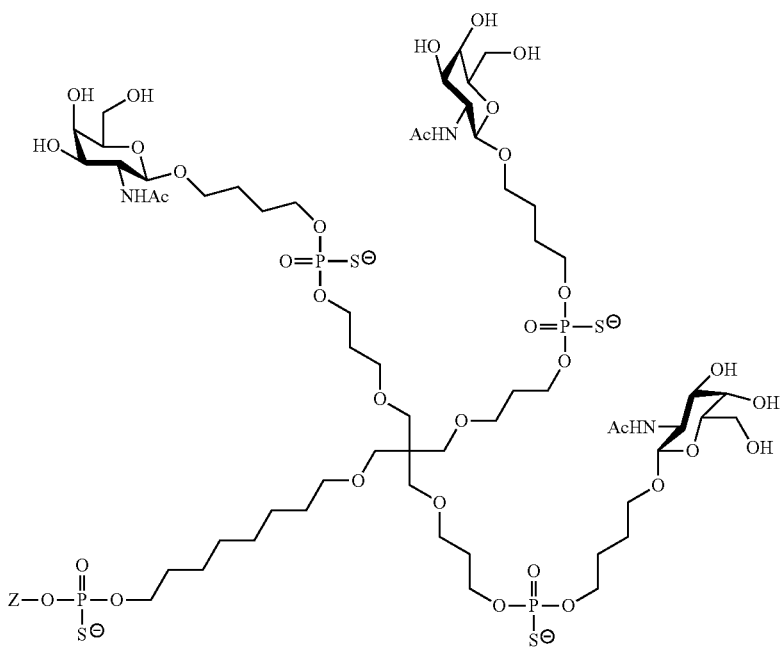
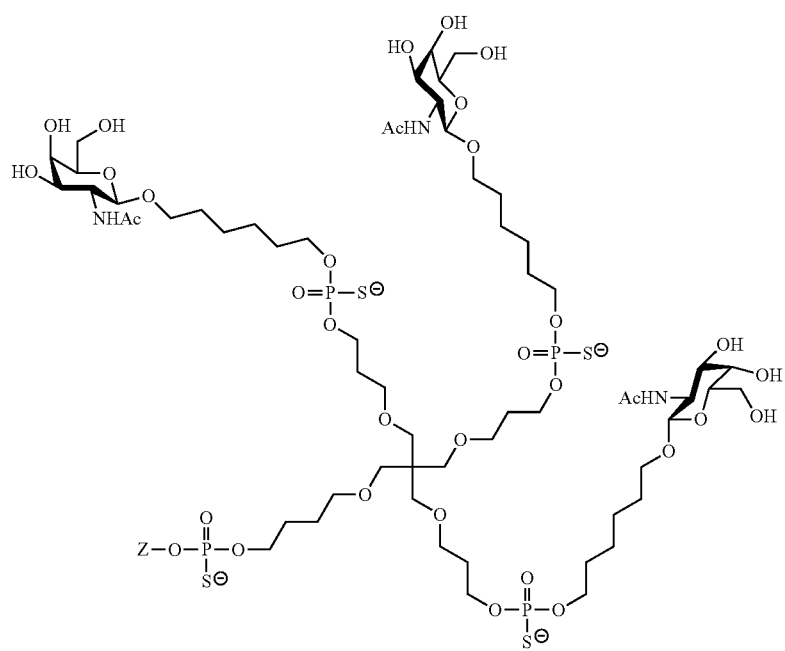

-continued
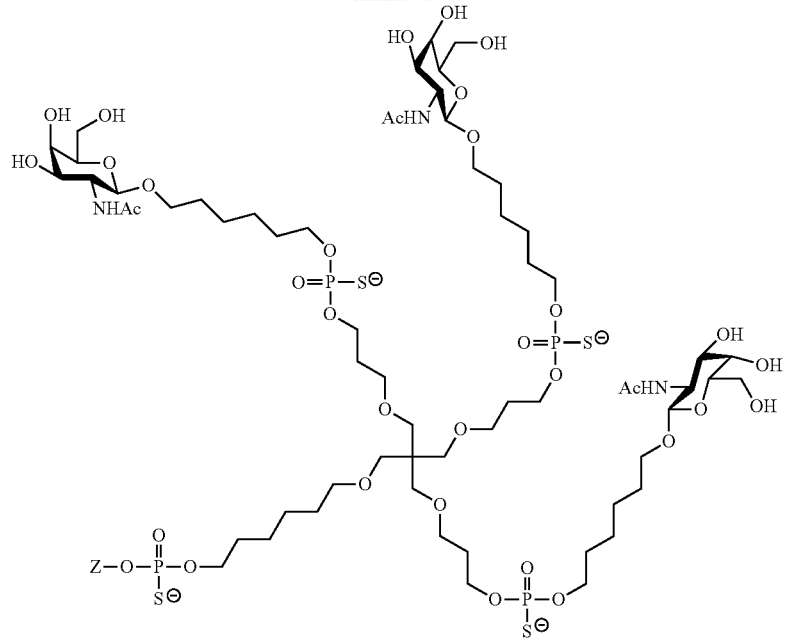
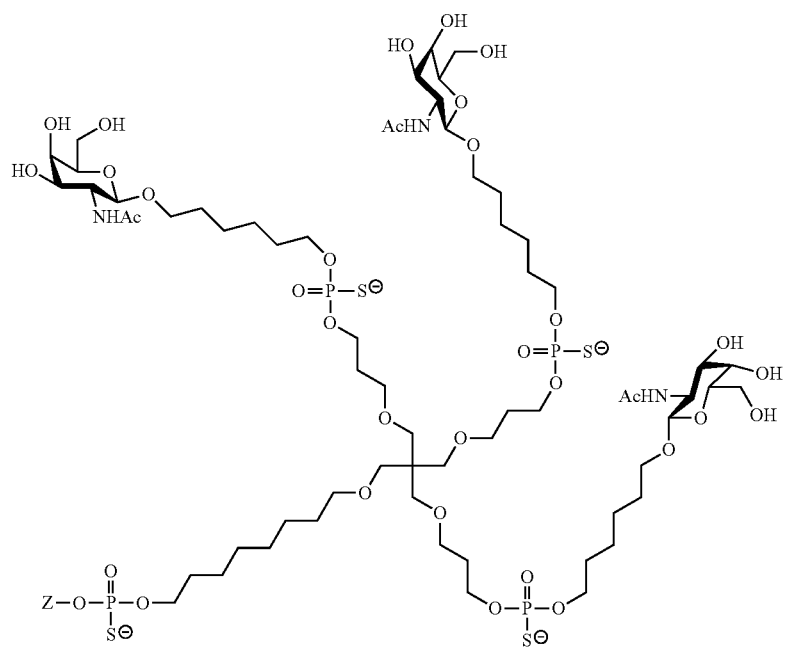
wherein Z represents a nucleic acid as defined herein before.

The ligand may comprise

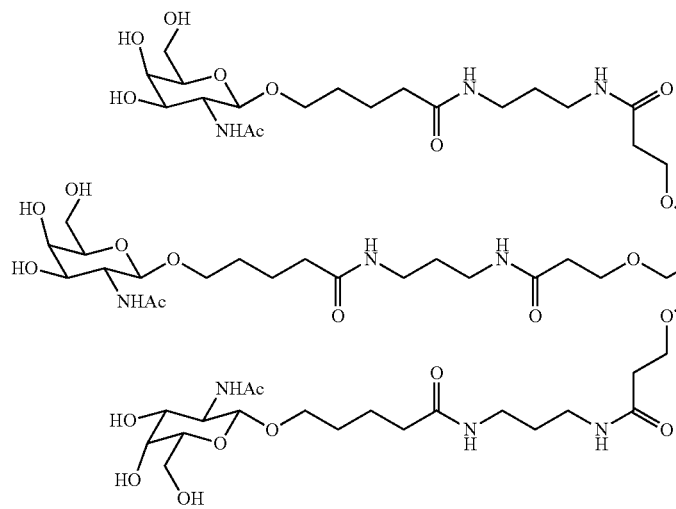

The invention also provides a composition comprising a nucleic acid or conjugated nucleic acid as defined herein and a physiologically acceptable excipient. The composition can comprise the following excipients:
  i) a cationic lipid, or a pharmaceutically acceptable salt thereof;
  ii) a steroid;
  iii) a phosphatidylethanolamine phospholipid;
  iv) a PEGylated lipid.

The content of the cationic lipid component in the composition may be from about 55 mol % to about 65 mol % of the overall lipid content of the lipid formulation, preferably about 59 mol % of the overall lipid content of the lipid composition.

The composition may comprise a cationic lipid having the structure a steroid having the structure

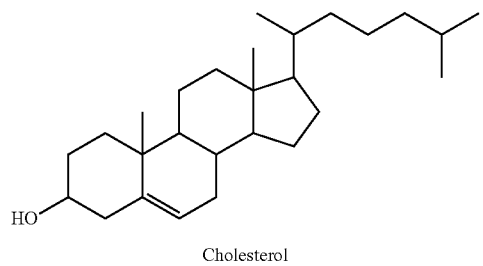

Cholesterol a phosphatidylethanolamine phospholipid having the structure

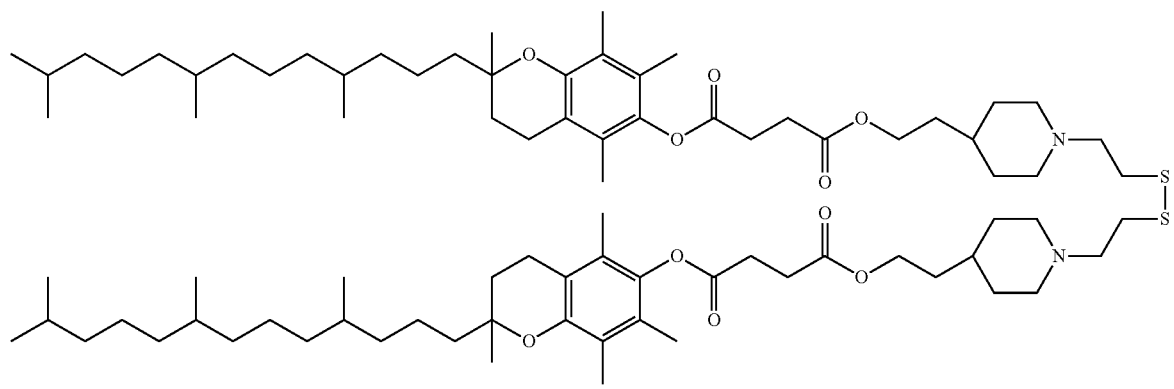 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

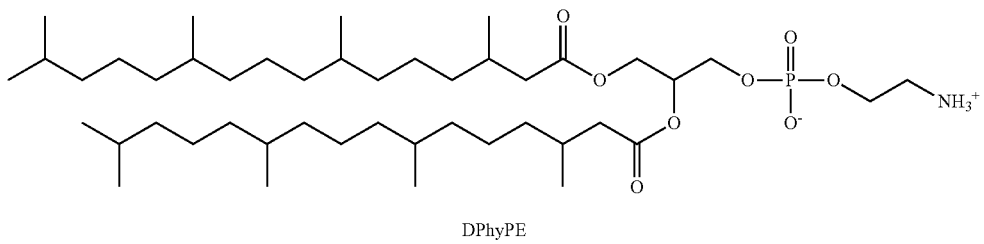 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE

And a PEGylated lipid having the structure

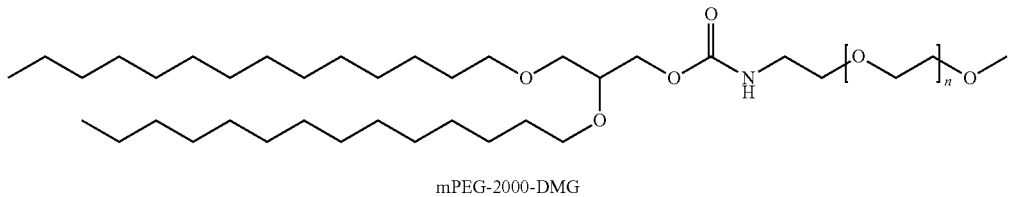

mPEG-2000-DMG

Also provided is a nucleic acid or conjugated nucleic acid according to any aspect of the invention for use in the treatment of a disease or disorder and/or in the manufacture of a medicament for treating a disease or disorder.

The invention provides a method of treating a disease or disorder comprising administration of a composition comprising a nucleic acid or conjugated nucleic acid according to any aspect of the invention to an individual in need of treatment. The nucleic acid may be administered to the subject subcutaneously, intravenously or using any other application routes such as oral, rectal or intraperitoneal.

A method of making a nucleic acid or conjugated nucleic acid according to the invention is also included.

DETAILED DESCRIPTION OF INVENTION

The present invention relates to a nucleic acid which is double stranded and directed to an expressed RNA transcript of a target gene and compositions thereof. These nucleic acids can be used in the treatment of a variety of diseases and disorders where reduced expression of the target gene product is desirable.

A first aspect of the invention relates to an nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from the target gene, wherein said first strand comprises a modified nucleotide at a selected position in order to facilitate processing of the nucleic acid by RISC. The first strand may comprise an unmodified nucleotide.

Another aspect of the invention relates to a nucleic acid capable of inhibiting the expression of a target gene, the nucleic acid comprising a first strand and a second strand, wherein the first stand and second strand are at least partially complementary with one another, wherein said first strand is at least partially complementary to RNA transcribed from a portion of said target gene; and wherein said first strand and/or said second strand include modified nucleotides.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide strand that is self complementary which 'folds' to form a double stranded molecule. The nucleic acid may be an siRNA molecule.

The nucleic acid may comprise ribonucleotides, modified ribonucleotides, deoxynucleotides, deoxyribonucleotides, or nucleotide analogous. The nucleic acid may further comprise a double-stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region refers it is meant the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single stranded regions. Further, within the duplex region, 100% complementarity is not required; substantial complementarity is allowable within a duplex region. Substantial complementarity refers to complementarity between the strands such that they are capable of annealing under biological conditions.

Techniques to empirically determine if two strands are capable of annealing under biological conditions are well known in the art. Alternatively, two strands can be synthesised and added together under biological conditions to determine if they anneal to one another.

The portion of the first strand and second strand that form at least one duplex region may be fully complementary and are at least partially complementary to each other.

Depending on the length of an nucleic acid, a perfect match in terms of base complementarity between the first strand and second strand is not necessarily required. However, the first and second strands must be able to hybridise under physiological conditions.

The complementarity between the first strand and second strand in the at least one duplex region may be perfect in that there are no nucleotide mismatches or additional/deleted nucleotides in either strand. Alternatively, the complementarity may not be perfect. The complementarity may be at least 70%, 75%, 80%, 85%, 90% or 95%.

The first strand and the second strand may each comprise a region of complementarity which comprises at least 15 contiguous nucleotides.

The nucleic acid may comprise a second sequence comprising a nucleotide sequence of SEQ ID NO:2, 4, 6, 8, 10, 12, 14, 16, 18, 20, 22, 24, 26, 28 or 30.

The nucleic acid involves the formation of a duplex region between all or a portion of the first strand and a portion of the target nucleic acid. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence however, the first strand must be able to form a duplex structure with both the second strand and the target sequence.

The complementarity between the first strand and the target sequence may be perfect (no nucleotide mismatches or additional/deleted nucleotides in either nucleic acid).

The complementarity between the first strand and the target sequence may not be perfect.

The complementarity may be at least 70%, 80%, 85%, 90% or 95%.

The identity between the first strand and the complementary sequence of the target sequence may be at least 75%, 80%, 85%, 90% or 95%, provided an nucleic acid is capable of reducing or inhibiting the expression of the target gene.

The nucleic acid may be able to reduce expression of the target gene by at least 25%, 50% or 75% of a comparative nucleic acid with perfect identity to the first strand and target sequence.

The nucleic acid may comprise a first strand and a second strand that are each from 17-35 or 19-25 nucleotides in length. The first strand and the second strand may be of different lengths.

The nucleic acid may be 15-25 nucleotide pairs in length. The nucleic acid may be 17-23 nucleotide pairs in length. The nucleic acid may be 17-25 nucleotide pairs in length. The nucleic acid may be 23-24 nucleotide pairs in length. The nucleic acid may be 19-21 nucleotide pairs in length. The nucleic acid may be 21-23 nucleotide pairs in length.

The nucleic acid may comprise a duplex region that consists of 19-25 nucleotide base pairs.

The duplex region may consist of 17, 18, 19, 20, 21, 22, 23, 24 or 25 base pairs which may be contiguous.

The nucleic acid may be blunt ended at both ends; have an overhang at one end and a blunt end at the other end; or have an overhang at both ends.

An "overhang" as used herein has its normal and customary meaning in the art, i.e. a single stranded portion of a nucleic acid that extends beyond the terminal nucleotide of a complementary strand in a double strand nucleic acid. The term "blunt end" includes double stranded nucleic acid whereby both strands terminate at the same position, regardless of whether the terminal nucleotide(s) are base paired. The terminal nucleotide of a first strand and a second strand at a blunt end may be base paired. The terminal nucleotide of a first strand and a second strand at a blunt end may not be paired. The terminal two nucleotides of an first strand and a second strand at a blunt end may be base paired. The terminal two nucleotides of an first strand and a second strand at a blunt end may not be paired.

The nucleic acid may have an overhang at one end and a blunt end at the other. The nucleic acid may have an overhang at both ends. The nucleic acid may be blunt ended at both ends.

The nucleic acid may be blunt ended at the end with the 5'-end of the first strand and the 3'-end of the second strand or at the 3'-end of the first strand and the 5'-end of the second strand.

The nucleic acid may comprise an overhang at a 3'- or 5'-end. The nucleic acid may have a 3'-overhang on the first strand. The nucleic acid may have a 3'-overhang on the second strand. The nucleic acid may have a 5'-overhang on the first strand. The nucleic acid may have a 5'-overhang on the second strand. The nucleic acid may have an overhang at both the 5'-end and 3'-end of the first strand. The nucleic acid may have an overhang at both the 5'-end and 3'-end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand.

An overhang at the 3'-end or 5' end of the second strand or the first strand may be selected from consisting of 1, 2, 3, 4 and 5 nucleotides in length. Optionally, an overhang may consist of 1 or 2 nucleotides, which may or may not be modified.

Unmodified polynucleotides, particularly ribonucleotides, may be prone to degradation by cellular nucleases, and, as such, modification/modified nucleotides may be included in the nucleic acid of the invention.

One or more nucleotides on the second and/or first strand of the nucleic acid of the invention may be modified.

Modifications of the nucleic acid of the present invention generally provide a powerful tool in overcoming potential limitations including, but not limited to, in vitro and in vivo stability and bioavailability inherent to native RNA molecules. The nucleic acid according to the invention may be modified by chemical modifications. Modified nucleic acid can also minimise the possibility of inducing interferon activity in humans. Modification can further enhance the functional delivery of a nucleic acid to a target cell. The modified nucleic acid of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution or insertion with analogues of nucleic acids or bases.

One or more nucleotides of a nucleic acid of the present invention may be modified. The nucleic acid may comprise at least one modified nucleotide. The modified nucleotide may be on the first strand. The modified nucleotide may be in the second strand. The modified nucleotide may be in the duplex region. The modified nucleotide may be outside the duplex region, i.e., in a single stranded region. The modified nucleotide may be on the first strand and may be outside the duplex region. The modified nucleotide may be on the second strand and may be outside the duplex region. The 3'-terminal nucleotide of the first strand may be a modified nucleotide. The 3'-terminal nucleotide of the second strand may be a modified nucleotide. The 5'-terminal nucleotide of the first strand may be a modified nucleotide. The 5'-terminal nucleotide of the second strand may be a modified nucleotide.

An nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, 24-26 modified nucleotides or about 26-28 modified nucleotides. In each case the nucleic acid comprising said modified nucleotides retains at least 50% of its activity as compared to the same nucleic acid but without said modified nucleotides. The nucleic acid may retain 55%, 60%, 65%, 70%, 75%, 80%, 85%, 90%, 95% or 100% or above of its activity as compared to the same nucleic acid but without said modified nucleotides The modified nucleotide may be a purine or a pyrimidine. At least half of the purines may be modified. At least half of the pyrimidines may be modified. All of the purines may be modified.

All of the pyrimidines may be modified. The modified nucleotides may be selected from the group consisting of a 3'-terminal deoxy-thymine (dT) nucleotide, a 2'-O-methyl modified nucleotide, a 2' modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified nucleotide, wherein the base is selected from 2-aminoadenosine, 2,6-diaminopurine, inosine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Nucleic acids discussed herein include unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, for example as occur naturally in the human body. Modified nucleotide as used herein refers to a nucleotide in which one or more of the components of the nucleic acid, namely sugars, bases, and phosphate moieties, are different from that which occur in nature. While they are referred to as modified nucleotides they will of course, because of the modification, include molecules which are not nucleotides, for example a polynucleotide molecules in which the ribophosphate backbone is replaced with a non-ribophosphate construct that allows hybridisation between strands i.e. the modified nucleotides mimic the ribophosphate backbone.

Many of the modifications described below that occur within a nucleic acid will be repeated within a polynucleotide molecule, such as a modification of a base, or a phosphate moiety, or the a non-linking O of a phosphate moiety. In some cases the modification will occur at all of the possible positions/nucleotides in the polynucleotide but in many cases it will not. A modification may only occur at a 3' or 5' terminal position, may only occur in a terminal regions, such as at a position on a terminal nucleotide or in the last 2, 3, 4, 5, or 10 nucleotides of a strand. A modification may occur in a double strand region, a single strand region, or in both.

A modification may occur only in the double strand region of an nucleic acid of the invention or may only occur in a single strand region of an nucleic acid of the invention. A phosphorothioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single strand regions, particularly at termini. The 5' end or 3' ends may be phosphorylated.

Stability of an nucleic acid of the invention may be increased by including particular bases in overhangs, or to include modified nucleotides, in single strand overhangs, e.g., in a 5' or 3' overhang, or in both. Purine nucleotides may be included in overhangs. All or some of the bases in a 3' or 5' overhang may be modified. Modifications can include the use of modifications at the 2' OH group of the ribose sugar, the use of deoxyribonucleotides, instead of ribonucleotides, and modifications in the phosphate group, such as phosphothioate modifications. Overhangs need not be homologous with the target sequence.

The 5'- or 3'-overhangs at the first strand, second strand or both strands of the dsRNA agent of the invention may be phosphorylated. In some embodiments, the overhang region contains two nucleotides having a phosphorothioate between the two nucleotides, where the two nucleotides can be the same or different. In one embodiment, the overhang is present at the 3'-end of the first strand, second strand or both strands. In one embodiment, this 3'-overhang is present in the first strand. In one embodiment, this 3'-overhang is present in the second strand.

Nucleases can hydrolyze nucleic acid phosphodiester bonds. However, chemical modifications to nucleic acids can confer improved properties, and, can render oligoribonucleotides more stable to nucleases.

Modified nucleic acids, as used herein, can include one or more of:

(i) alteration, e.g., replacement, of one or both of the non-linking phosphate oxygens and/or of one or more of the linking phosphate oxygens (referred to as linking even if at the 5' and 3' terminus of the nucleic acid of the invention);
(ii) alteration, e.g., replacement, of a constituent of the ribose sugar, e.g., of the 2' hydroxyl on the ribose sugar;
(iii) replacement of the phosphate moiety with "dephospho" linkers;
(iv) modification or replacement of a naturally occurring base;
(v) replacement or modification of the ribose-phosphate backbone;
(vi) modification of the 3' end or 5' end of the RNA, e.g., removal, modification or replacement of a terminal phosphate group or conjugation of a moiety, e.g., a fluorescently labeled moiety, to either the 3' or 5' end of RNA.

The terms replacement, modification, alteration, indicates a difference from a naturally occurring molecule.

Specific modifications are discussed in more detail below.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

A modified nucleotide can include modification of the sugar groups. The 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), O(CH2CH2O)nCH2CH2OR; "locked" nucleic acids (LNA) in which the 2' hydroxyl is connected, e.g., by a methylene bridge, to the 4' carbon of the same ribose sugar; O-AMINE (AMINE=NH2; alkylamino, dialkylamino, heterocyclyl, arylamino, diaryl amino, heteroaryl amino, or diheteroaryl amino, ethylene diamine, polyamino) and aminoalkoxy, O(CH2)nAMINE, (e.g., AMINE=NH2; alkylamino, dialkylamino, heterocyclyl, arylamino, diaryl amino, heteroaryl amino, or diheteroaryl amino, ethylene diamine, polyamino).

"Deoxy" modifications include hydrogen halo; amino (e.g., NH2; alkylamino, dialkylamino, heterocyclyl, arylamino, diaryl amino, heteroaryl amino, diheteroaryl amino, or amino acid); NH(CH2CH2NH)nCH2CH2-AMINE (AMINE=NH2; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substituents of certain embodiments include 2'-methoxyethyl, 2'-OCH3, 2'-O-allyl, 2'-C-allyl, and 2'-fluoro.

The sugar group can also contain one or more carbons that possess the opposite stereochemical configuration than that of the corresponding carbon in ribose. Thus, a modified nucleotides may contain a sugar such as arabinose.

Modified nucleotides can also include "abasic" sugars, which lack a nucleobase at C-I'.

These abasic sugars can further contain modifications at one or more of the constituent sugar atoms.

The 2' modifications may be used in combination with one or more phosphate linker modifications (e.g., phosphorothioate).

The phosphate group can be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

The phosphate linker and ribose sugar may be replaced by nuclease resistant nucleotides.

Examples include the mophilino, cyclobutyl, pyrrolidine and peptide nucleic acid (PNA) nucleoside surrogates. In certain embodiments, PNA surrogates may be used.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)nCH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu$^{3+}$ complexes of tetraazamacrocycles).

Terminal modifications can be added for a number of reasons, including to modulate activity or to modulate resistance to degradation. Terminal modifications useful for modulating activity include modification of the 5' end with phosphate or phosphate analogs. Nucleic acids of the invention, on the first or second strand, may be 5' phosphorylated or include a phosphoryl analog at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g., RP(OH)(O)—O-5'-, (OH)$_2$(O)P-5'-CH$_2$—), 5'vinylphosphonate, 5'-alkyletherphosphonates (R=alkylether=methoxymethyl (MeOCH$_2$—), ethoxymethyl, etc., e.g., RP(OH)(O)—O-5'-).

The nucleic acid of the present invention may include one or more phosphorothioate modifications on one or more of the terminal ends of the first and/or the second strand. Optionally, each or either end of the first strand may comprise one or two or three phosphorothioate modified nucleotides. Optionally, each or either end of the second strand may comprise one or two or three phosphorothioate modified nucleotides. Optionally, both ends of the first strand and the 5' end of the second strand may comprise two phosphorothioate modified nucleotides. By phosphorothioate modified nucleotide it is meant that the linkage between the nucleotide and the adjacent nucleotide comprises a phosphorothioate group instead of a standard phosphate group.

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N<4>-acetyl cytosine, 2-thiocytosine, N6-methyladenine, N6-isopentyladenine, 2-methylthio-N6-isopentenyladenine, N-methylguanines, or O-alkylated bases.

As used herein, the terms "non-pairing nucleotide analog" means a nucleotide analog which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

Certain moieties may be linked to the 5' terminus of the first strand or the second strand and includes abasic ribose moiety, abasic deoxyribose moiety, modifications abasic ribose and abasic deoxyribose moieties including 2' O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

The nucleic acids of the invention may be included one or more inverted nucleotides, for example inverted thymidine or inverted adenine (for example see Takei, et al., 2002. JBC 277 (26):23800-06).

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits, is reduced below that observed in the absence of a nucleic acid of the invention; for example the expression may be reduced to 90%, 80%, 70%, 60%, 50%, 40%, 30%, 20%, 15% or less than that observed in the absence of an inhibitor.

The nucleic acid of the present invention may comprise an abasic nucleotide. The term "abasic" as used herein, refers to moieties lacking a base or having other chemical groups in place of a base at the 1' position, for example a 3',3'-linked or 5',5'-linked deoxyabasic ribose derivative.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

One or more of the odd numbered nucleotides of the first strand of the nucleic acid of the invention may be modified wherein the first strand is numbered 5' to 3'. The term "odd numbered" as described herein means a number not divisible by two. Examples of odd numbers are 1, 3, 5, 7, 9, 11 and so on. One or more of the even numbered nucleotides of the first strand of the nucleic acid of the invention may be modified, wherein the first strand is numbered 5' to 3'. The term "even numbered" as described herein means a number which is evenly divisible by two. Examples of even numbers are 2, 4, 6, 8, 10, 12, 14 and so on. One or more of the odd numbered nucleotides of the second strand of the nucleic acid of the invention may be modified wherein the second strand is numbered 3' to 5'. One or more of the even numbered nucleotides of the second strand of the nucleic acid of the invention may be modified, wherein the second strand is numbered 3' to 5'.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more add nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first stand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with the second modification.

The nucleic acid of the invention may have the modified nucleotides of the first strand shifted by at least one nucleotide relative to the unmodified or differently modified nucleotides of the second strand.

One or more or each of the odd numbered nucleotides may be modified in the first strand and one or more or each of the even numbered nucleotides may be modified in the second strand. One or more or each of the alternating nucleotides on either or both strands may be modified by a second modification. One or more or each of the even numbered nucleotides may be modified in the first strand and one or more or each of the even numbered nucleotides may be modified in the second strand. One or more or each of the alternating nucleotides on either or both strands may be modified by a second modification. One or more or each of the odd numbered nucleotides may be modified in the first strand and one or more of the odd numbered nucleotides may be modified in the second strand by a common modification. One or more or each of the alternating nucleotides on either or both strands may be modified by a second modification. One or more or each of the even numbered nucleotides may be modified in the first strand and one or more or each of the odd numbered nucleotides may be modified in the second strand by a common modification. One or more or each of the alternating nucleotides on either or both strands may be modified by a second modification.

The nucleic acid of the invention may comprise single or double stranded constructs that comprise at least two regions of alternating modifications in one or both of the strands. These alternating regions can comprise up to about 12 nucleotides but preferably comprise from about 3 to about 10 nucleotides. The regions of alternating nucleotides may be located at the termini of one or both strands of the nucleic acid of the invention. The nucleic acid may comprise from 4 to about 10 nucleotides of alternating nucleotides at each termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd numbered nucleotides of the first strand. One or more nucleotides of second strand may also be modified with the second modification. One or more nucleotides with the second modification may be adjacent to each other and to nucleotides having a modification that is the same as the modification of the odd numbered nucleotides of the first strand. The first strand may also comprise phosphorothioate linkages between the two nucleotides at the 3' end and at the 5' end. The second strand may comprise a phosphorothioate linkage between the two nucleotides at 5' end. The second strand may also be conjugated to a ligand at the 5' end.

The nucleic acid of the invention may comprise a first strand comprising adjacent nucleotides that are modified with a common modification. One or more of such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of second strand may also be modified with the second modification. One or more nucleotides with the second modification may be adjacent. The first strand may also comprise phosphorothioate linkages between the two nucleotides at the 5' end and at the 3' end. The second strand may comprise a phosphorothioate linkage between the two nucleotides at 3' end. The second strand may also be conjugated to a ligand at the 5' end.

The nucleotides for the purposes of modification as described herein (unless otherwise indicated) are numbered from 5' to 3' on the first strand and 3' and 5' on the second strand. Nucleotides numbered 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand. Nucleotides are numbered for the sake of the nucleic acid of the present invention from 5' to 3' on the first strand and 3' and 5' on the second strand, unless otherwise indicated.

The nucleotides numbered 2, 4, 6, 8, 10, 12, 14, 16, 18, 20, 22 and 24 may be modified on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter or longer than 25 nucleotides in length, such as 19 nucleotides in length, there are no nucleotides numbered 20, 21, 22, 23, 24 and 25 to be modified. The skilled person understands the description above to apply to shorter or longer strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

The modification and/or modifications may each and individually be selected from the group consisting of 3'-terminal deoxy-thymine, 2'-O-methyl, a 2'-deoxy-modification, a 2'-amino-modification, a 2'-alkyl-modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-O-methyl and/or at least one modification may be 2'-F. Further modifications as described herein may be present on the first and/or second strand.

Throughout the description of the invention, "same or common modification" means the same modification to any nucleotide, be that A, G, C or U modified with a group such as such as a methyl group or a fluoro group. Is it not taken to mean the same addition on the same nucleotide. For example, 2'F-dU, 2'F-dA, 2'F-dC, 2'F-dG are all considered to be the same or common modification, as are 2'-OMe-rU, 2'-OMe-rA; 2'-OMe-rC; 2'-OMe-rG. A 2'F modification is a different modification to a 2'OMe modification.

Some representative modified nucleic acid sequences of the present invention are shown in the examples. These examples are meant to be representative and not limiting.

Preferably, the nucleic acid may comprise a modification and the second or further modification which are each and individually selected from the group comprising 2'-O-methyl modification and 2'-F modification. The nucleic acid may comprise a modification that is 2'-O-methyl (2'OMe) that may be a first modification, and a second modification that is 2'-F. The nucleic acid of the invention may also include a phosphorothioate modification and/or a deoxy modification which may be present in or between the terminal 1, 2 or 3 nucleotides of each or any end of each or both strands.

The nucleic acid of the invention may be conjugated to a ligand.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. The endosomolytic component may contain a chemical group which undergoes a change in charge or protonation in response to a change in pH. The endosomolytic component may be linear or branched.

Ligands can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics. Ligands can include a naturally occurring substance, such as a protein, carbohydrate, or lipid. The ligand may be a recombinant or synthetic molecule.

Ligands can also include targeting groups, e.g. a cell or tissue targeting agent. The targeting ligand may be a lectin, glycoprotein, lipid or protein.

Other examples of ligands include dyes, intercalating agents, cross-linkers, porphyrins, polycyclic aromatic hydrocarbons, artificial endonucleases or a chelator, lipophilic molecules, alkylating agents, phosphate, amino, mercapto, PEG, MPEG, alkyl, substituted alkyl, radiolabelled markers, enzymes, haptens, transport/absorption facilitators, synthetic ribonucleases, or imidazole clusters.

Ligands can be proteins, e.g. glycoproteins or peptides. Ligands may also be hormones or hormone receptors. They may also include non-peptidic species, such as lipids, lectins, carbohydrates, vitamins, or cofactors.

The ligand may be a substance such as a drug which can increase the uptake of the nucleic acid into a cell, for example, by disrupting the cell's cytoskeleton.

The ligand may increase uptake of the nucleic acid into the cell by activating an inflammatory response. Such ligands include tumour necrosis factor alpha (TNF-alpha), interleukin-1 beta, or gamma interferon.

The ligand may be a lipid or lipid-based molecule. The lipid or lipid-based molecule preferably binds a serum protein. Preferably, the lipid-based ligand binds human serum albumin (HSA). A lipid or lipid-based molecule can increase resistance to degradation of the conjugate, increase targeting or transport into target cell, and/or can adjust binding to a serum protein. A lipid-based ligand can be used to modulate binding of the conjugate to a target tissue.

The ligand may be a steroid. Preferably, the ligand is cholesterol or a cholesterol derivative.

The ligand may be a moiety e.g. a vitamin, which is taken up by a target cell. Exemplary vitamins include vitamin A, E, K, and the B vitamins. Vitamins may be taken up by a proliferating cell, which may be useful for delivering the nucleic acid to cells such as malignant or non-malignant tumour cells.

The ligand may be a cell-permeation agent, such as a helical cell-permeation agent. Preferably such an agent is amphipathic.

The ligand may be a peptide or peptidomimetic. A peptidomimetic is a molecule capable of folding into a defined three-dimensional structure similar to a natural peptide. The peptide or peptidomimetic ligand may include naturally occurring or modified peptides, or both. A peptide or peptidomimetic can be a cell permeation peptide, cationic peptide, amphipathic peptide, or hydrophobic peptide. The peptide moiety can be a dendrimer peptide, constrained peptide, or crosslinked peptide. The peptide moiety can include a hydrophobic membrane translocation sequence. The peptide moiety can be a peptide capable of carrying large polar molecules such as peptides, oligonucleotides, and proteins across cell membranes, e.g. sequences from the HIV Tat protein (GRKKRRQRRRPPQ) and the *Drosophila* Antennapedia protein (RQIKIWFQNRRMKWKK). Preferably the peptide or peptidomimetic is a cell targeting peptide, e.g. arginine-glycine-aspartic acid (RGD)-peptide.

The ligand may be a cell permeation peptide that is capable of permeating, for example, a microbial cell or a mammalian cell.

The ligand may be a pharmacokinetic modulator. The pharmacokinetic modulator may be lipophiles, bile acids, steroids, phospholipid analogues, peptides, protein binding agents, PEG, vitamins, etc.

When two or more ligands are present, the ligands can all have the same properties, all have different properties, or some ligands have the same properties while others have different properties. For example, a ligand can have targeting properties, have endosomolytic activity or have PK modulating properties. In a preferred embodiment, all the ligands have different properties.

Ligands can be coupled to the nucleic acid at the 3'-end, 5'-end, and/or at an internal position.

Preferably the ligand is coupled to the nucleic acid via an intervening tether or linker.

In some embodiments the nucleic acid is a double-stranded nucleic acid. In a double-stranded nucleic acid the ligand may be attached to one or both strands. In some embodiments, a double-stranded nucleic acid contains a ligand conjugated to the second strand. In other embodiments, a double-stranded nucleic acid contains a ligand conjugated to the first strand.

Ligands can be conjugated to nucleobases, sugar moieties, or internucleosidic linkages of nucleic acid molecules. Conjugation to purine nucleobases or derivatives thereof can occur at any position including endocyclic and exocyclic atoms. Conjugation to pyrimidine nucleotides or derivatives thereof can also occur at any position. Conjugation to sugar moieties of nucleosides can occur at any carbon atom. Conjugation to internucleosidic linkages may occur at the phosphorus atom of a phosphorus-containing linkage or at an oxygen, nitrogen, or sulphur atom bonded to the phosphorus atom. For amine- or amide-containing internucleosidic linkages, conjugation may occur at the nitrogen atom of the amine or amide or to an adjacent carbon atom.

The ligand is typically a carbohydrate, e.g. a monosaccharide, disaccharide, trisaccharide, tetrasaccharide or polysaccharide. The ligand may be conjugated to the nucleic acid by a linker. The saccharide may be selected from N-acetyl galactoseamine, mannose, galactose, glucose, glucosamine and fucose. The saccharide may be N-acetyl galactoseamine (GalNAc).

A ligand for use in the present invention may therefore comprise (i) one or more N-acetyl galactosamine (GalNac) moieties and derivatives thereof, and (ii) a linker, wherein the linker conjugates the GalNac moieties to a sequence as defined in any preceding aspects. The linker may be a bivalent or trivalent or tetravalent branched structure. The nucleotides may be modified as defined herein.

Means for efficient delivery of oligonucleotides, in particular double stranded nucleic acids of the invention, to cells in vivo is important and requires specific targeting and substantial protection from the extracellular environment, particularly serum proteins. One method of achieving specific targeting is to conjugate a ligand to the nucleic acid. The targeting moiety helps in targeting the nucleic acid to the required target site and there is a need to conjugate appropriate ligands for the desired receptor sites for the conjugated molecules to be taken up by the cells such as by endocytosis. The ligand can be any moiety or ligand that is capable of targeting a specific receptor.

For example, the Asialoglycoprotein receptor (ASGP-R) is a high capacity receptor, which is highly abundant on hepatocytes. One of the first disclosures of triantennary cluster glycosides was in U.S. Pat. No. 5,885,968. Conjugates having three GalNAc ligands and comprising phosphate groups are known and are described in Dubber et al. (2003). The ASGP-R shows a 50-fold higher affinity for N-Acetyl-D-Galactosylamine (GalNAc) than D-Gal.

Hepatocytes expressing the lectin (asialoglycoprotein receptor; ASGPR), which recognizes specifically terminal β-galactosyl subunits of glycosylated proteins or other oligosaccharides (P. H. Weigel et. al., 2002,) can be used for targeting a drug to the liver by covalent coupling of galactose or galactoseamine to the drug substance (S. Ishibashi, et. al. 1994). Furthermore the binding affinity can be significantly increased by the multi-valency effect, which is achieved by the repetition of the targeting unit (E. A. L. Biessen et. al., 1995).

The ASGPR is a mediator for an active endosomal transport of terminal β-galactosyl containing glycoproteins, thus ASGPR is highly suitable for targeted delivery of drug candidates like nucleic acid, which have to be delivered into a cell (Akinc et al.).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

The saccharide may be selected from N-acetyl galactoseamine, mannose, galactose, glucose, glucosamone and fucose. The saccharide may be N-acetyl galactoseamine (GalNAc).

"GalNAc" refers to 2-(Acetylamino)-2-deoxy-D-galactopyranose, commonly referred to in the literature as N-acetyl galactosamine. Reference to "GalNAc" or "N-acetyl galactoseamine" includes both the β-form: 2-(Acetylamino)-2-deoxy-β-D-galactopyranose and the α-form: 2-(Acetylamino)-2-deoxy-α-D-galactopyranose. Both the 1-form: 2-(Acetylamino)-2-deoxy-3-D-galactopyranose and α-form: 2-(Acetylamino)-2-deoxy-α-D-galactopyranose may be used interchangeably. Preferably, the compounds of the invention comprise the 1-form, 2-(Acetylamino)-2-deoxy-β-D-galactopyranose.

The ligand may comprise GalNAc.

The ligand may comprise a compound of formula I:

$$[S-X^1-P-X^2]_3-A-X^3- \quad (I)$$

wherein:
S represents a saccharide, wherein the saccharide is N-acetyl galactosamine;
$X^1$ represents $C_3$-$C_6$ alkylene or $(-CH_2-CH_2-O)_m(-CH_2)_2-$ wherein m is 1, 2, or 3;
P is a phosphate or modified phosphate (preferably a thiophosphate);
$X^2$ is alkylene or an alkylene ether of the formula $(-CH_2)_n-O-CH_2-$ where n=1-6;
A is a branching unit;
$X^3$ represents a bridging unit;
wherein a nucleic acid according to the present invention is conjugated to $X^3$ via a phosphate or modified phosphate (preferably a thiophosphate).

In formula I, branching unit "A" branches into three in order to accommodate the three saccharide ligands. The branching unit is covalently attached to the ligands and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

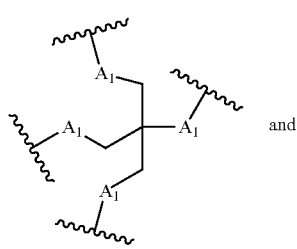

and

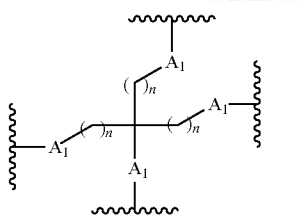

wherein each $A_1$ independently represents O, S, C=O or NH; and each n independently represents an integer from 1 to 20.

The branching unit may have a structure selected from:

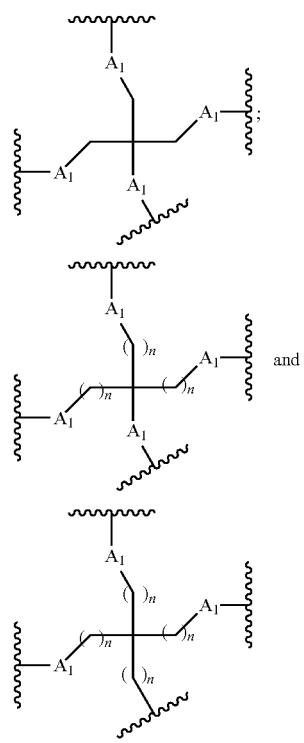

wherein each $A_1$ independently represents O, S, C=O or NH; and each n independently represents an integer from 1 to 20.

The branching unit may have a structure selected from:

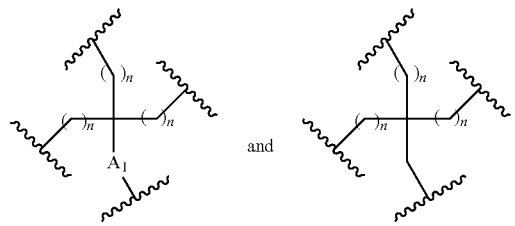

wherein $A_1$ is O, S, C=O or NH; and each n independently represents an integer from 1 to 20.

The branching unit may have the structure:

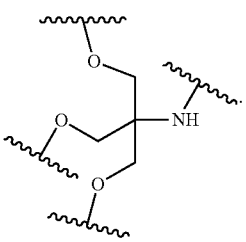 [SMILES: *NC(CO*)(CO*)CO*]

The branching unit may have the structure:

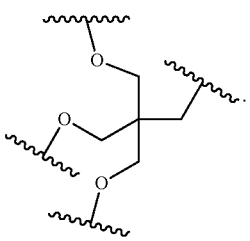 [SMILES: *CC(CO*)(CO*)CO*]

The branching unit may have the structure:

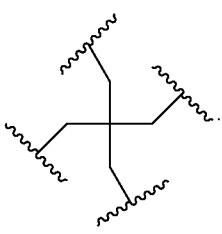 [SMILES: *CC(C*)(C*)C*]

Optionally, the branching unit consists of only a carbon atom.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene— wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula —($C_1$-$C_{20}$ alkylene)-O—($C_1$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—O—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

The ligand may comprise a compound of formula (II):

[S—$X^1$—P—$X^2$]$_3$-A-$X^3$— (II)

wherein:
S represents a saccharide;
$X^1$ represents $C_3$-$C_6$ alkylene or (—$CH_2$—$CH_2$—O)$_m$(—$CH_2$)$_2$— wherein m is 1, 2, or 3;
P is a phosphate or modified phosphate (preferably a thiophosphate);
$X^2$ is $C_1$-$C_8$ alkylene;
A is a branching unit selected from:

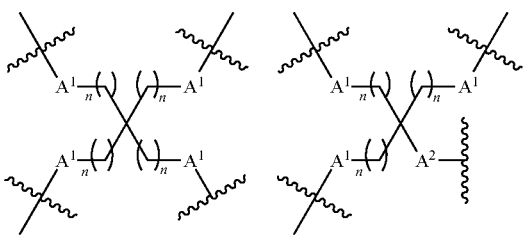

$A^1$ = O, NH
n = 1 to 4

$A^1$ = O, NH
$A^2$ = NH, CH$_2$, O
n = 1 to 4

$X^3$ is a bridging unit;
wherein a nucleic acid according to the present invention is conjugated to $X^3$ via a phosphate or modified phosphate (preferably a thiophosphate).

Branching unit A may have the structure:

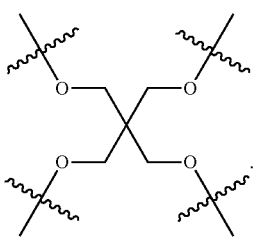 [SMILES: *OCC(CO*)(CO*)CO*]

Branching unit A may have the structure:

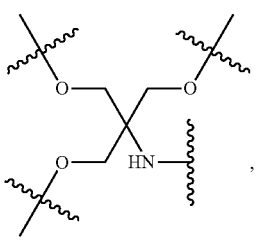

wherein $X^3$ is attached to the nitrogen atom.

$X^3$ may be $C_1$-$C_{20}$ alkylene. Preferably, $X^3$ is selected from the group consisting of —$C_3H_6$—, —$C_4H_8$—, —$C_6H_{12}$— and —$C_8H_{16}$—, especially —$C_4H_8$—, —$C_6H_{12}$— and —$C_8H_{16}$—.

The ligand may comprise a compound of formula (III):

[S—$X^1$—P—$X^2$]$_3$-A-$X^3$— (III)

wherein:
S represents a saccharide;
$X^1$ represents $C_3$-$C_6$ alkylene or (—$CH_2$—$CH_2$—O)$_m$(—$CH_2$)$_2$— wherein m is 1, 2, or 3;
P is a phosphate or modified phosphate (preferably a thiophosphate);
$X^2$ is an alkylene ether of formula —$C_3H_6$—O—$CH_2$—;

A is a branching unit;

X³ is an alkylene ether of formula selected from the group consisting of —CH₂—O—CH₂—, —CH₂—O—C₂H₄—, —CH₂—O—C₃H₆—, —CH₂—O—C₄H₈—, —CH₂—O—C₅H₁₀—, —CH₂—O—C₆H₁₂—, —CH₂—O—CO₇H₁₄—, and —CH₂—O—C₆H₁₆—, wherein in each case the —CH₂— group is linked to A, wherein a nucleic acid according to the present invention is conjugated to X³ via a phosphate or modified phosphate (preferably a thiophosphate).

The branching unit may comprise carbon. Preferably, the carbon unit is carbon.

X³ may be selected from the group consisting of —CH₂—O—C₄H₈—, —CH₂—O—C₃H₁₀—, —CH₂—O—C₆H₁₂—, —CH₂—O—C₇H₁₄—, and —CH₂—O—C₈H₁₆—. Preferably, X³ is selected from the group consisting of —CH₂—O—C₄H₈—, —CH₂—O—C₆H₁₂— and —CH₂—O—C₈H₁₆.

For any of the above aspects, P represents a modified phosphate group. P can be represented by:

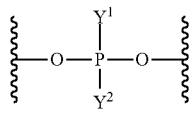

wherein Y¹ and Y² each independently represent =O, =S, —O⁻, —OH, —SH, —BH₃, —OCH₂CO₂, —OCH₂CO₂Rˣ, —OCH₂C(S)ORˣ, and —ORˣ, wherein Rˣ represents C₁-C₆ alkyl and wherein

indicates attachment to the remainder of the compound.

For example, Y¹ may represent —OH and Y² may represent =O or =S; or

Y¹ may represent —O⁻ and Y² may represent =O or =S;

Y¹ may represent =O and Y² may represent —CH₃, —SH, —ORˣ, or —BH₃

Y¹ may represent =S and Y² may represent —CH₃, ORˣ or —SH.

It will be understood by the skilled person that in certain instances there will be delocalisation between Y¹ and Y².

Preferably, the modified phosphate group is a thiophosphate group. Thiophosphate groups include bithiophosphate (i.e. where Y¹ represents=S and Y² represents —S—) and monothiophosphate (i.e. where Y¹ represents —O⁻ and Y² represents=S, or where Y¹ represents =O and Y² represents —S—). Preferably, P is a monothiophosphate. The inventors have found that conjugates having thiophosphate groups in replacement of phosphate groups have improved potency and duration of action in vivo.

P may also be an ethylphosphate (i.e. where Y¹ represents =O and Y² represents OCH₂CH₃).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

For any of the above aspects, the saccharide may be selected from N-acetyl with one or more of galactosamine, mannose, galactose, glucose, glucosamine and fructose. Preferably, the saccharide is two molecules of N-acetyl galactosamine (GalNAc). The compounds of the invention may have 3 ligands which are each preferably N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form: 2-(Acetylamino)-2-deoxy-α-D-galactopyranose may be used interchangeably. Preferably, the compounds of the invention comprise the 1-form, 2-(Acetylamino)-2-deoxy-β-D-galactopyranose.

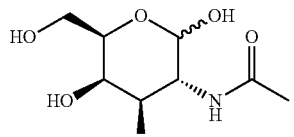

2-(Acetylamino)-2-deoxy-D-galactopyranose

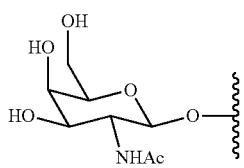

2-(Acetylamino)-2-deoxy-β-D-galactopyranose

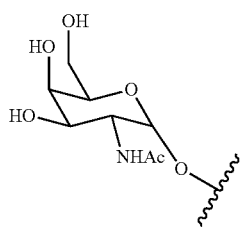

2-(Acetylamino)-2-deoxy-α-D-galactopyranose

For any of the above compounds of formula (III), X¹ may be (—CH₂—CH₂—O—)ₘ(—CH₂—)₂— wherein m is 1, 2, or 3. X¹ may be (—CH₂—CH₂—O)(—CH₂—)₂—. X¹ may be (—CH₂—CH₂—O)₂(—CH₂—)₂—. X¹ may be (—CH₂—CH₂—O)₃(—CH₂—)₂—. Preferably, X¹ is (—CH₂—CH₂—O)₂(—CH₂—)₂—. Alternatively, X¹ represents C₃-C₆ alkylene. X¹ may be propylene. X¹ may be butylene. X¹ may be pentylene. X¹ may be hexylene. Preferably the alkyl is a linear alkylene. In particular, X¹ may be butylene.

For compounds of formula (III), X² represents an alkylene ether of formula —C₃H₆—O—CH₂— i.e.

C₃ alkoxy methylene, or —CH₂CH₂CH₂OCH₂—.

The present invention therefore additionally provides a conjugated nucleic acid having one of the following structures

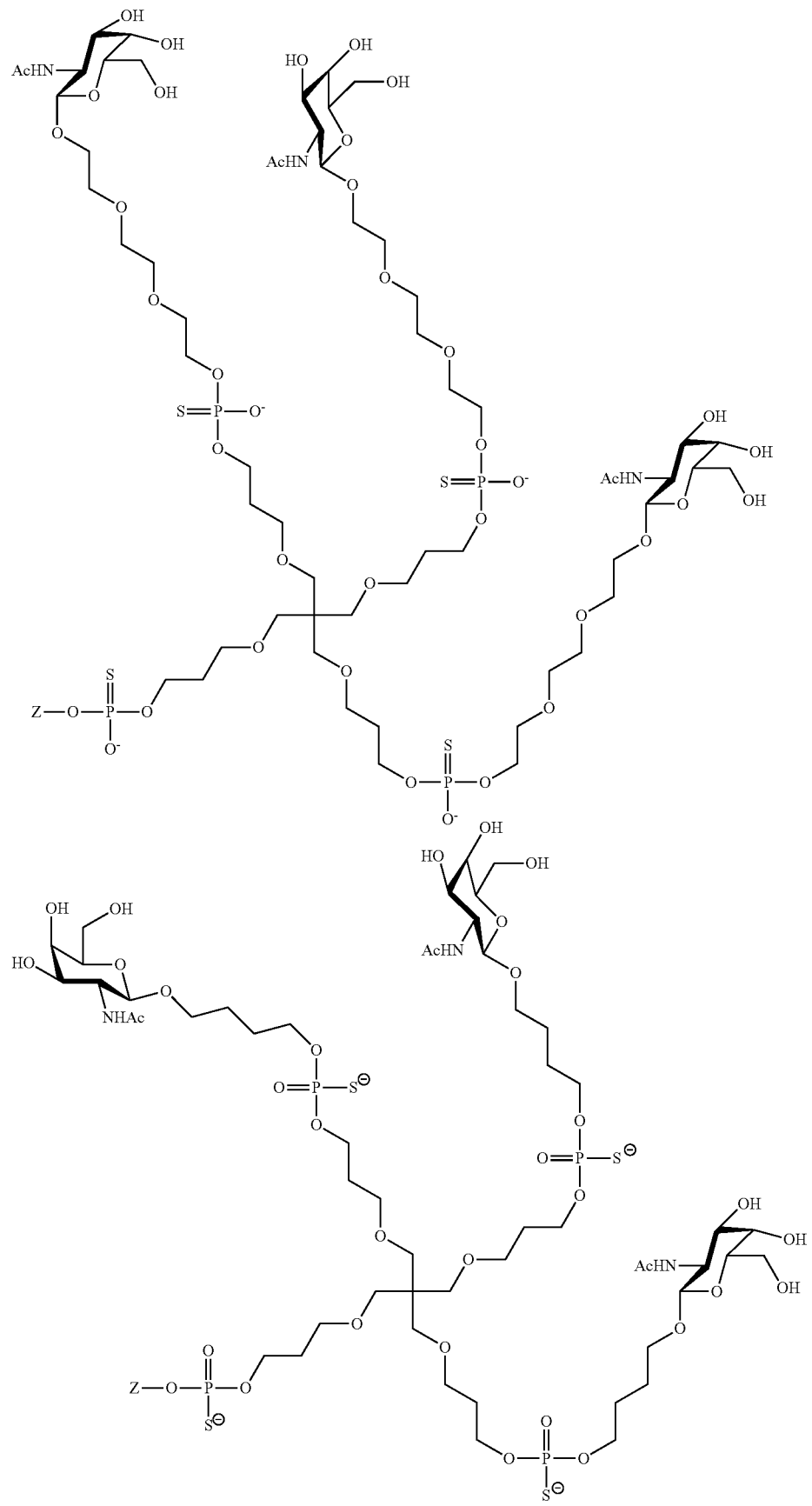

-continued
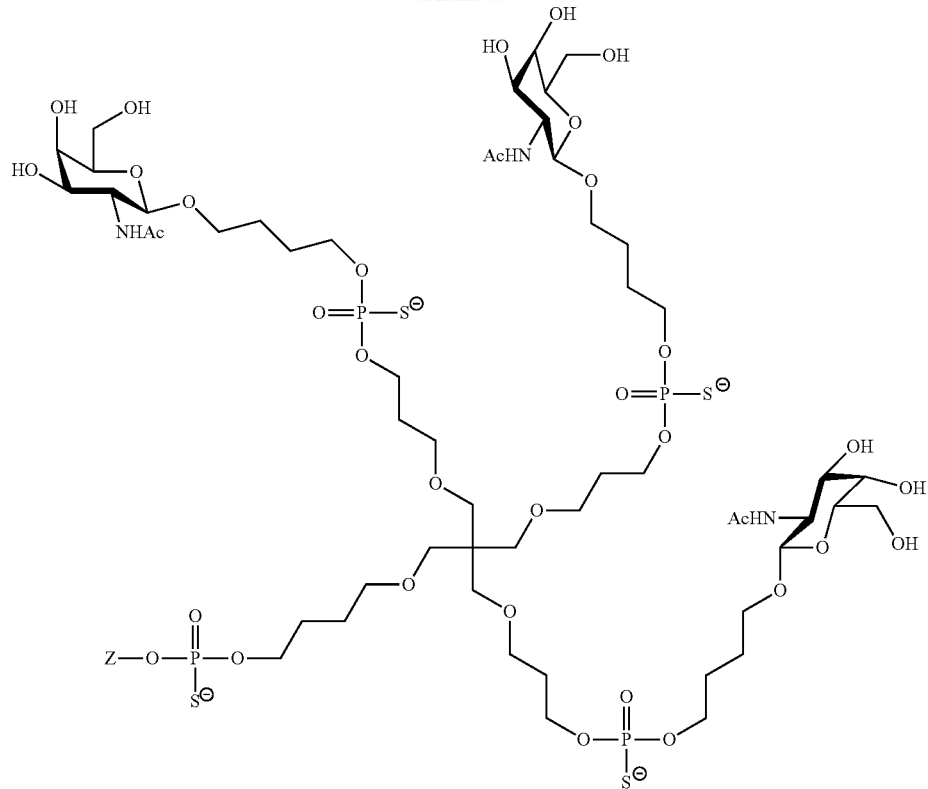
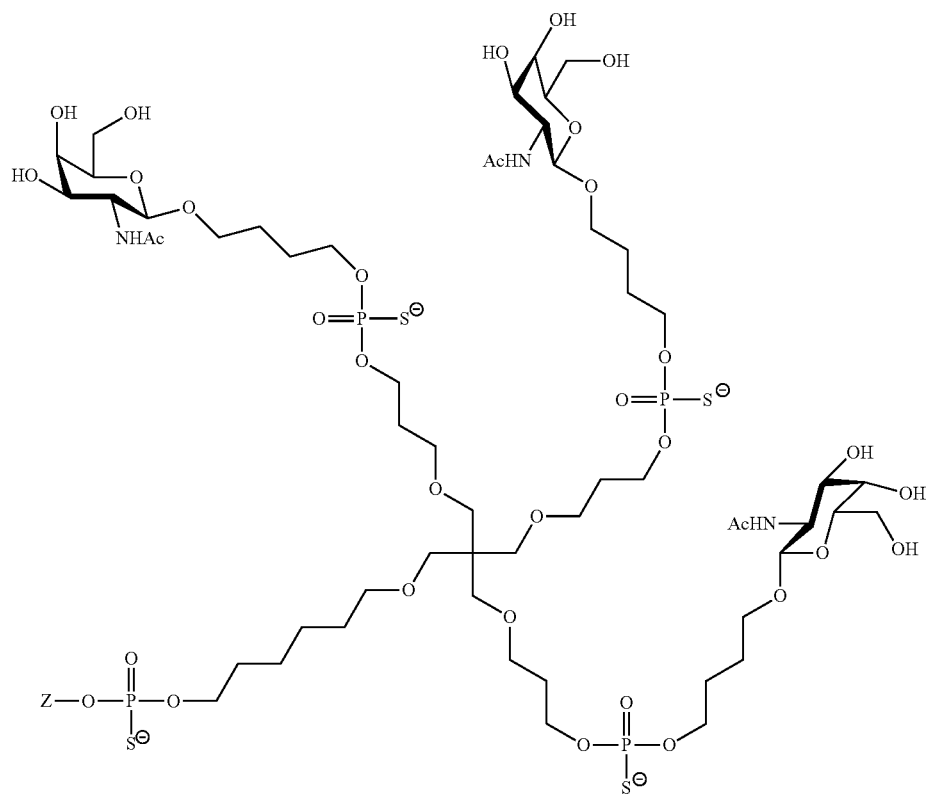

-continued
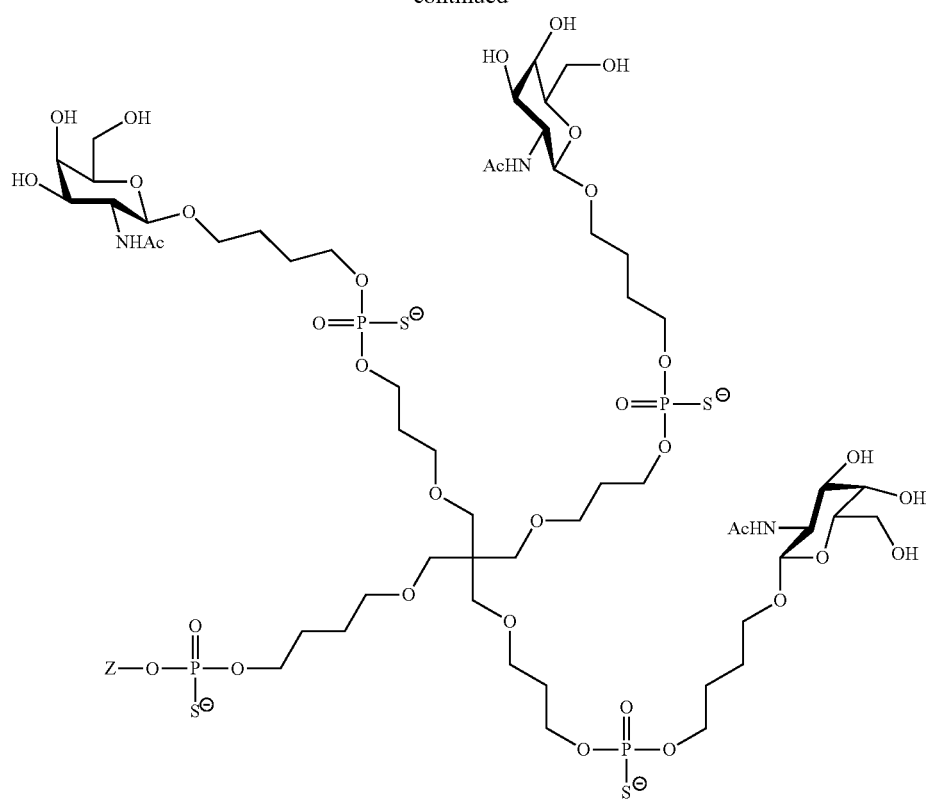
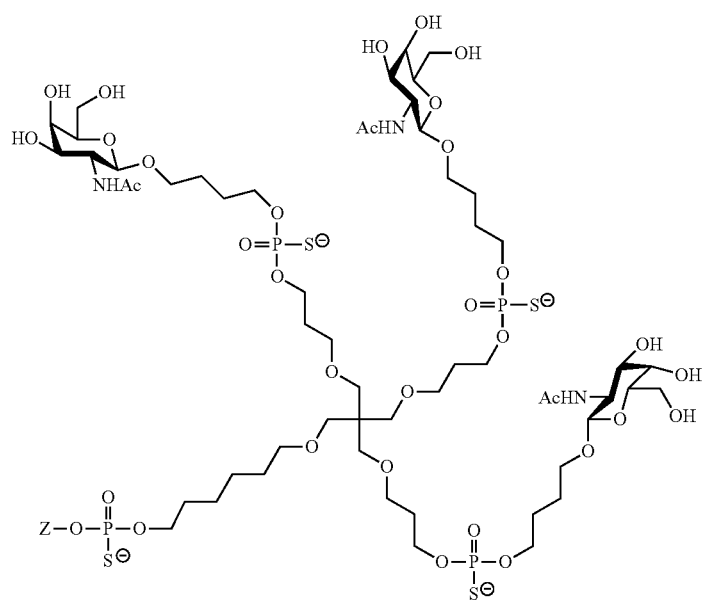

-continued

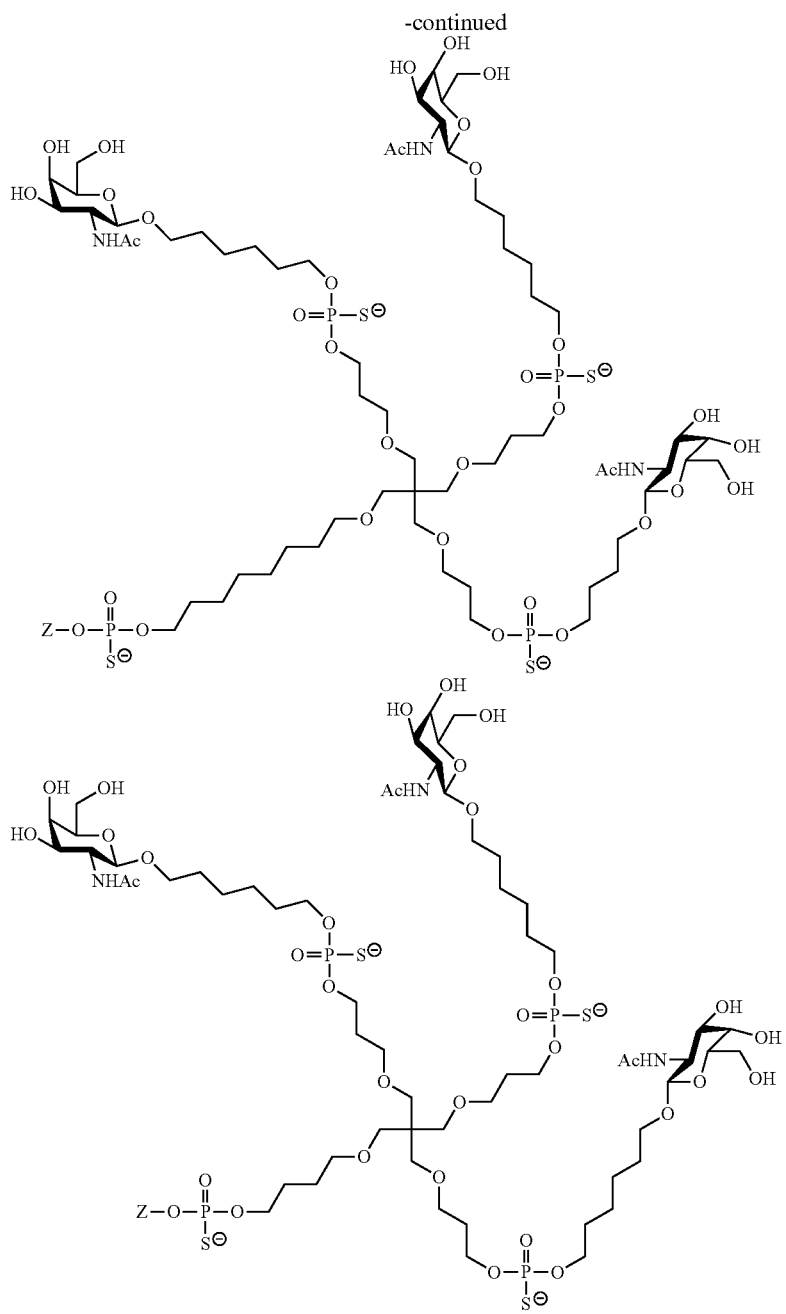

wherein Z represents a nucleic acid as defined herein before.

The invention provides, as another aspect, a nucleic acid or conjugated nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from the target gene, wherein said first strand comprises a modified nucleotide at selected position in order to facilitate processing of the nucleic acid by RISC, wherein the nucleic acid is conjugated indirectly or directly to a ligand via a linker. The nucleic acid may be conjugated to a ligand as herein described. The nucleotides of the first and/or second strand may be modified, as herein described.

The ligand may be conjugated to the nucleic acid via a linker as set out in formula I and wherein the first strand is modified with a 2'OMe modification on the odd numbered nucleotides, and modified with a 2'F on the even numbered nucleotides, and the second strand is modified with a 2'OMe on the even numbered nucleotides and modified with a 2'F on the odd numbered nucleotides.

The ligand may GalNac and be attached via a linker.

The nucleic acid as described herein may be formulated with a lipid in the form of a liposome. Such a formulation may be described in the art as a lipoplex. The formulation with a lipid/liposome may be used to assist with delivery of the nucleic acid of the invention to the target cells. The lipid delivery system herein described may be used as an alternative to a conjugated ligand. The modifications herein described may be present when using a nucleic acid of the invention with a lipid delivery system or with a ligand conjugate delivery system.

Such a lipoplex may comprise a lipid formulation comprising:
i) a cationic lipid, or a pharmaceutically acceptable salt thereof;
ii) a steroid;
iii) a phosphatidylethanolamine phospholipid;
iv) a PEGylated lipid.

The cationic lipid may be an amino cationic lipid.
The cationic lipid may have the formula (I):

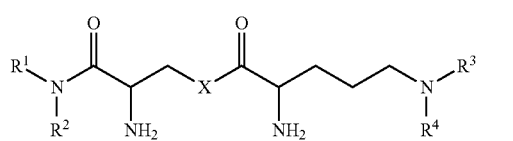

or a pharmaceutically acceptable salt thereof, wherein:
X represents O, S or NH;
$R^1$ and $R^2$ each independently represents a $C_4$-$C_{22}$ linear or branched alkyl chain or a $C_4$-$C_{22}$ linear or branched alkenyl chain with one or more double bonds, wherein the alkyl or alkenyl chain optionally contains an intervening ester, amide or disulfide;
when X represents S or NH, $R^3$ and $R^4$ each independently represent hydrogen, methyl, ethyl, a mono- or polyamine moiety, or $R^3$ and $R^4$ together form a heterocyclyl ring;
when X represents O, $R^3$ and $R^4$ each independently represent hydrogen, methyl, ethyl, a mono- or polyamine moiety, or $R^3$ and $R^4$ together form a heterocyclyl ring, or $R^3$ represents hydrogen and $R^4$ represents $C(NH)(NH_2)$.

The cationic lipid may have the formula (IA):

The content of the cationic lipid component may be from about 55 mol % to about 65 mol % of the overall lipid content of the formulation. In particular, the cationic lipid component is about 59 mol % of the overall lipid content of the formulation.

The formulations further comprise a steroid. the steroid may be cholesterol. The content of the steroid may be from about 26 mol % to about 35 mol % of the overall lipid content of the lipid formulation. More particularly, the content of steroid may be about 30 mol % of the overall lipid content of the lipid formulation.

The phosphatidylethanolamine phospholipid may be selected from group consisting of 1,2-diphytanoyl-sn-glycero-3-phosphoethanolamine (DPhyPE), 1,2-dioleoyl-sn-glycero-3-phosphoethanolamine (DOPE), 1,2-distearoyl-sn-glycero-3-phosphoethanolamine (DSPE), 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Dilinoleoyl-sn-glycero-3-phosphoethanolamine (DLoPE), 1-Palmitoyl-2-oleoyl-sn-glycero-3-phosphoethanolamine (POPE), 1,2-Dierucoyl-sn-glycero-3-phosphoethanolamine (DEPE), 1,2-Disqualeoyl-sn-glycero-3-phosphoethanolamine (DSQPE) and 1-Stearoyl-2-linoleoyl-sn-glycero-3-phosphoethanolamine (SLPE). The content of the phospholipid may be about 10 mol % of the overall lipid content of the formulation.

The PEGylated lipid may be selected from the group consisting of 1,2-dimyristoyl-sn-glycerol, methoxypolyethylene glycol (DMG-PEG) and $C_{16}$-Ceramide-PEG. The content of the PEGylated lipid may be about 1 to 5 mol % of the overall lipid content of the formulation.

The content of the cationic lipid component in the formulation may be from about 55 mol % to about 65 mol % of the overall lipid content of the lipid formulation, preferably about 59 mol % of the overall lipid content of the lipid formulation.

The formulation may have a molar ratio of the components of i):ii):iii):iv) selected from 55:34:10:1; 56:33:10:1; 57:32:10:1; 58:31:10:1; 59:30:10:1; 60:29:10:1; 61:28:10:1; 62:27:10:1; 63:26:10:1; 64:25:10:1; and 65:24:10:1.

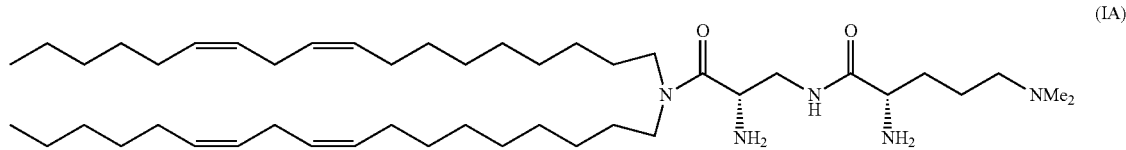 [SMILES: CCCCC/C=C\C/C=C\CCCCCCCCN(CCCCCCCC/C=C\C/C=C\CCCCC)C(=O)[C@@H](N)CNC(=O)[C@@H](N)CCCN(C)C]

or a pharmaceutically acceptable salt thereof.
The cationic lipid may have the formula (IB):

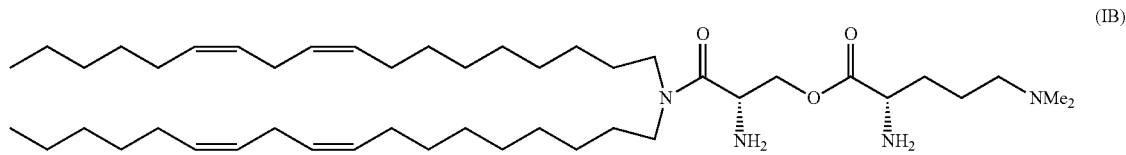 [SMILES: CCCCC/C=C\C/C=C\CCCCCCCCN(CCCCCCCC/C=C\C/C=C\CCCCC)C(=O)[C@@H](N)COC(=O)[C@@H](N)CCCN(C)C]

or a pharmaceutically acceptable salt thereof.

The formulation may comprise a cationic lipid having the structure

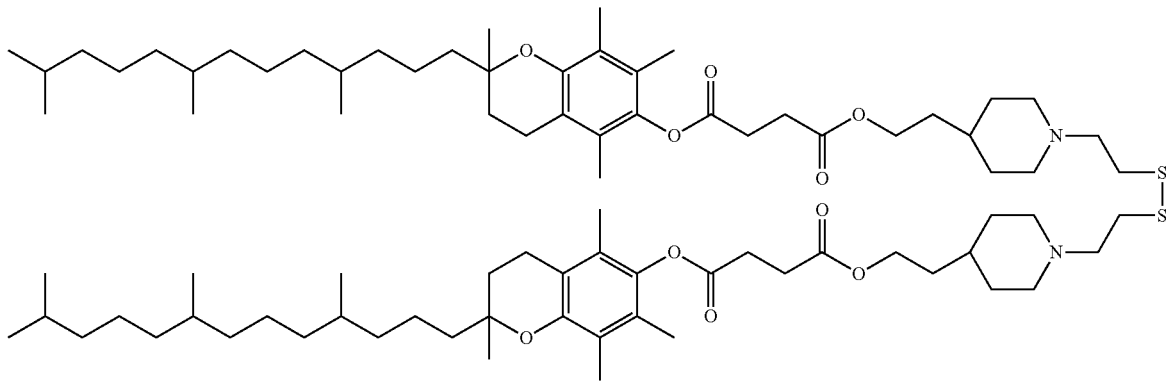 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

a steroid having the structure

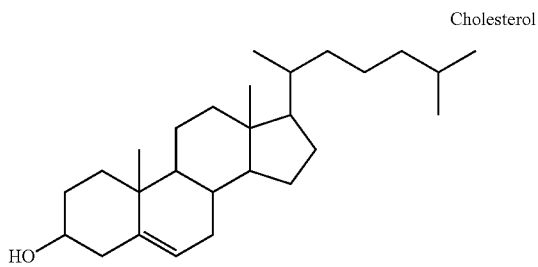 [SMILES: CC(C)CCCC(C)C1CCC2C3CC=C4CC(O)CCC4(C)C3CCC12C]

Cholesterol a phosphatidylethanolamine phospholipid having the structure

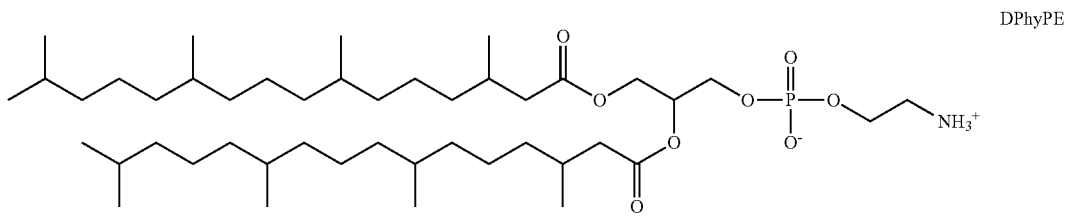 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE

And a PEGylated lipid having the structure

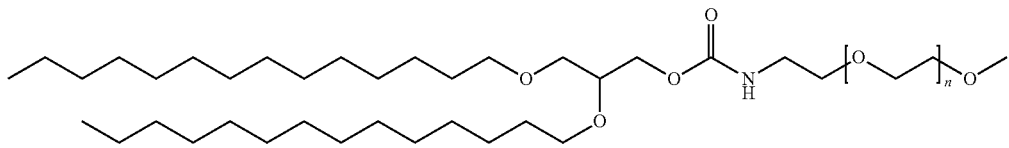

mPEF-2000-DMG

Neutral liposome compositions may be formed from, for example, dimyristoyl phosphatidylcholine (DMPC) or dipalmitoyl phosphatidylcholine (DPPC). Anionic liposome compositions may be formed from dimyristoyl phosphatidylglycerol, while anionic fusogenic liposomes may be formed primarily from dioleoyl phosphatidylethanolamine (DOPE). Another type of liposomal composition may be formed from phosphatidylcholine (PC) such as, for example, soybean PC, and egg PC. Another type is formed from mixtures of phospholipid and/or phosphatidylcholine and/or cholesterol.

A positively charged synthetic cationic lipid, N—[I-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells. DOTMA analogues can also be used to form liposomes.

Derivatives and analogues of lipids described herein may also be used to form liposomes.

A liposome containing a nucleic acid can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The nucleic acid preparation is then added to the micelles that include the lipid component. The cationic groups on the lipid interact with the nucleic acid and condense around the nucleic acid to form a liposome. After condensation, the detergent is removed, e.g., by dialysis, to yield a liposomal preparation of nucleic acid.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favour condensation.

Nucleic acid formulations may include a surfactant. In one embodiment, the nucleic acid is formulated as an emulsion that includes a surfactant.

A surfactant that is not ionized is a non-ionic surfactant. Examples include non-ionic esters, such as ethylene glycol esters, propylene glycol esters, glyceryl esters etc., nonionic alkanolamides, and ethers such as fatty alcohol ethoxylates, propoxylated alcohols, and ethoxylated/propoxylated block polymers.

A surfactant that carries a negative charge when dissolved or dispersed in water is an anionic surfactant. Examples include carboxylates, such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates.

A surfactant that carries a positive charge when dissolved or dispersed in water is a cationic surfactant. Examples include quaternary ammonium salts and ethoxylated amines.

A surfactant that has the ability to carry either a positive or negative charge is an amphoteric surfactant. Examples include acrylic acid derivatives, substituted alkylamides, N-alkylbetaines and phosphatides.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic. A micelle may be formed by mixing an aqueous solution of the nucleic acid, an alkali metal alkyl sulphate, and at least one micelle forming compound.

Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Phenol and/or m-cresol may be added to the mixed micellar composition to act as a stabiliser and preservative. An isotonic agent such as glycerine may as be added.

A nucleic acid preparation may be incorporated into a particle such as a microparticle. Microparticles can be produced by spray-drying, lyophilisation, evaporation, fluid bed drying, vacuum drying, or a combination of these methods.

The present invention also provides pharmaceutical compositions comprising a nucleic acid or conjugated nucleic acid of the invention. The pharmaceutical compositions may be used as medicaments or as diagnostic agents, alone or in combination with other agents. For example, a nucleic acid or conjugated nucleic acid of the invention can be combined with a delivery vehicle (e.g., liposomes) and excipients, such as carriers, diluents. Other agents such as preservatives and stabilizers can also be added. Methods for the delivery of nucleic acids are known in the art and within the knowledge of the person skilled in the art.

A nucleic acid or conjugated nucleic acid of the present invention can also be administered in combination with other therapeutic compounds, either administrated separately or simultaneously, e.g., as a combined unit dose. The invention also includes a pharmaceutical composition comprising a nucleic acid or conjugated nucleic acid according to the present invention in a physiologically/pharmaceutically acceptable excipient, such as a stabilizer, preservative, diluent, buffer, and the like.

The pharmaceutical composition may be specially formulated for administration in solid or liquid form. The composition may be formulated for oral administration, parenteral administration (including, for example, subcutaneous, intramuscular, intravenous, or epidural injection), topical application, intravaginal or intrarectal administration, sublingual administration, ocular administration, transdermal administration, or nasal administration. Delivery using subcutaneous or intravenous methods are preferred.

Dosage levels for the medicament and pharmaceutical compositions of the invention can be determined by those skilled in the art by routine experimentation. In one embodiment, a unit dose may contain between about 0.01 mg/kg and about 100 mg/kg body weight of nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Dosage levels may also be calculated via other parameters such as, e.g., body surface area.

The pharmaceutical composition may be a sterile injectable aqueous suspension or solution, or in a lyophilized form. In one embodiment, the pharmaceutical composition may comprise lyophilized lipoplexes or an aqueous suspension of lipoplexes. The lipoplexes preferably comprises a nucleic acid of the present invention. Such lipoplexes may be used to deliver the nucleic acid of the invention to a target cell either in vitro or in vivo.

The pharmaceutical compositions and medicaments of the present invention may be administered to a mammalian subject in a pharmaceutically effective dose. The mammal may be selected from humans, dogs, cats, horses, cattle, pig, goat, sheep, mouse, rat, hamster and guinea pig.

A further aspect of the invention relates to a nucleic acid or conjugated nucleic acid of the invention or the pharmaceutical composition comprising a nucleic acid or conjugated nucleic acid of the invention for use in the treatment of a disease or disorder. The invention includes a pharmaceutical composition comprising a nucleic acid or conjugated nucleic acid according to the present invention in a physiologically/pharmaceutically acceptable excipient, such as a stabiliser, preservative, diluent, buffer and the like.

The pharmaceutical composition may be a sterile injectable aqueous suspension or solution, or in a lyophilised form.

Pharmaceutically acceptable compositions may comprise a therapeutically-effective amount of a nucleic acid or conjugated nucleic acid in any embodiment according to the invention, taken alone or formulated with one or more pharmaceutically acceptable carriers, excipient and/or diluents.

Examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

Stabilisers may be agents that stabilise a nucleic acid or conjugated nucleic acid, for example a protein that can complex with the nucleic acid, chelators (e.g. EDTA), salts, RNAse inhibitors, and DNAse inhibitors.

In some cases it is desirable to slow the absorption of the drug from subcutaneous or intramuscular injection in order to prolong the effect of a drug. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The nucleic acid described herein may be capable of inhibiting the expression of the target gene in a cell. The nucleic acid described herein may be capable of partially inhibiting the expression of the target gene in a cell. Inhibition may be complete, i.e. 0% of the expression level of target gene expression in the absence of the nucleic acid of the invention. Inhibition of target gene expression may be partial, i.e. it may be 15%, 20%, 30%, 40%, 50%, 60%, 70%, 75%, 80%, 85%, 90%, 95% of target gene expression in the absence of a nucleic acid of the invention. Inhibition may last 4 weeks, 5 weeks, 6 weeks, 7 weeks, 8 weeks, 10 weeks, 11 weeks, 12 weeks, 13 weeks, 14 weeks or up to 3 months, when used in a subject, such as a human subject. The nucleic acid or conjugated nucleic acid or composition comprising the same may be for use once, every week, every two weeks, every three weeks, every four weeks, every five weeks, every six weeks, every seven weeks, or every eight weeks. The nucleic acid or conjugated nucleic acid may be for use subcutaneously or intravenously.

In cells and/or subjects treated with or receiving a nucleic acid or conjugated nucleic acid of the present invention, the target gene expression may be inhibited compared to untreated cells and/or subjects by at least about 30%, 35%, 40%, 45%, 50%, 55%, 60%, 65%, 70%, 75%, 80%, 85%, 90%, 95%, 98%, or 100%. The level of inhibition may allow treatment of a disease associated with target gene expression or overexpression, or may allow further investigation into the functions of the target gene product.

The target gene may be Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erkl/2 gene, PCNA(p21) gene, MYB gene, JU gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF I/CIPI) gene, mutations in the p27(KIPI) gene, mutations in the PPM ID gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene. In particular, the target gene may be TMPRSS6 or ALDH2.

A further aspect of the invention relates to nucleic acid of the invention in the manufacture of a medicament for treating a disease or disorder.

Also included in the invention is a method of treating a disease or disorder comprising administration of a pharmaceutical composition comprising an nucleic acid as described herein, to an individual in need of treatment. The nucleic acid composition may be administered twice every week, once every week, every two weeks, every three weeks, every four weeks, every five weeks, every six weeks, every seven weeks, or every eight weeks. The nucleic acid may be administered to the subject subcutaneously or intravenously.

In one embodiment, a subject is administered an initial dose and one or more maintenance doses of a nucleic acid or conjugated nucleic acid. The maintenance dose or doses can be the same or lower than the initial dose, e.g., one-half less of the initial dose. The maintenance doses are, for example, administered no more than once every 2, 5, 10, or 30 days. The treatment regimen may last for a period of time which will vary depending upon the nature of the particular disease, its severity and the overall condition of the patient.

In one embodiment, the composition includes a plurality of nucleic acid agent species. In another embodiment, the nucleic acid agent species has sequences that are non-overlapping and non-adjacent to another species with respect to a naturally occurring target sequence. In another embodiment, the plurality of nucleic acid agent species is specific for different naturally occurring target genes. In another embodiment, the nucleic acid agent is allele specific.

The nucleic acid or conjugated nucleic acid of the present invention can also be administered or for use in combination with other therapeutic compounds, either administered separately or simultaneously, e.g. as a combined unit dose.

The nucleic acid or conjugated nucleic acid of the present invention can be produced using routine methods in the art including chemically synthesis or expressing the nucleic acid either in vitro (e.g., run off transcription) or in vivo. For example, using solid phase chemical synthesis or using an expression vector. In one embodiment, the expression vector can produce the nucleic acid of the invention in a target cell. Methods for the synthesis of the nucleic acid described herein are known to persons skilled in the art.

In one aspect the invention relates to a nucleic acid capable of inhibiting the expression of a target gene, the nucleic acid comprising a first strand and a second strand, wherein the first stand and second strand are at least partially complementary with one another, wherein said first strand is at least partially complementary to RNA transcribed from a portion of said target gene; and wherein said first strand and/or said second strand include modified nucleotides. Further preferred features of the nucleic acid disclosed herein are as follows:

A nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene, wherein said first strand includes modified nucleotides or unmodified nucleotides at a plurality of positions in order to facilitate processing of the nucleic acid by RISC.

In one aspect "facilitate processing by RISC" means that the nucleic acid can be processed by RISC, for example any modification present will permit the nucleic acid to be processed by RISC, suitably such that SiRNA activity can take place.

A nucleic acid as disclosed herein, wherein the nucleotides at positions 2 and 14 from the 5' end of the first strand are not modified with a 2' O-methyl modification, and the nucleotide on the second strand which corresponds to position 13 of the first strand is not modified with a 2' O-methyl modification.

A nucleotide on the second strand that "corresponds to" a position on the first strand is suitably the nucleotide that base pairs with that nucleotide on the first strand.

In one aspect the nucleotide on the second strand which corresponds to position 13 of the first strand is the nucleotide that forms a base pair with position 13 of the first strand.

In one aspect the nucleotide on the second strand which corresponds to position 11 of the first strand is the nucleotide that forms a base pair with position 11 of the first strand.

In one aspect the nucleotide on the second strand which corresponds to position 12 of the first strand is the nucleotide that forms a base pair with position 12 of the first strand.

This nomenclature may be applied to other positions of the second strand.

For example, in a 19-mer nucleic acid which is double stranded and blunt ended, position 13 of the first strand would pair with position 7 of the second strand. Position 11 of the first strand would pair with position 9 of the second strand. This nomenclature may be applied to other positions of the second strand.

The nucleotide that corresponds to position 13 of the first strand is suitably position 13 of the second strand, counting from the 3' of the second strand, starting from the first nucleotide of the double stranded region. Likewise position 11 of the second strand is suitably the 11th nucleotide from the 3' of the second strand, starting from the first nucleotide of the double stranded region. This nomenclature may be applied to other positions of the second strand.

In one aspect, in the case of a partially complementary first and second strand, the nucleotide on the second strand that "corresponds to" a position on the first strand may not necessarily form a base pair if that position is the position in which there is a mismatch, but the principle of the nomenclature still applies.

Preferred is a first and second strand that are fully complementary over the duplex region (ignoring any overhang regions) and there are no mismatches within the double stranded region of the nucleic acid.

Also preferred are:

A nucleic acid as disclosed herein, wherein the nucleotides at positions 2 and 14 from the 5' end of the first strand are not modified with a 2' O-methyl modification, and the nucleotide on the second strand which corresponds to position 11 of the first strand is not modified with a 2' O-methyl modification.

A nucleic acid as disclosed herein, wherein the nucleotides at positions 2 and 14 from the 5' end of the first strand are not modified with a 2' O-methyl modification, and the nucleotides on the second strand which corresponds to position 11 and 13 of the first strand are not modified with a 2' O-methyl modification.

In one aspect the nucleotide on the second strand which corresponds to position 12 of the first strand is not modified with a 2' O-methyl modification. This limitation on the nucleic acid may be seen with any other limitation described herein.

Therefore another aspect of the invention is a nucleic acid as disclosed herein, wherein the nucleotides at positions 2 and 14 from the 5' end of the first strand are not modified with a 2' O-methyl modification, and the nucleotides on the second strand which corresponds to position 11-13 of the first strand are not modified with a 2' O-methyl modification.

A nucleic acid as disclosed herein, wherein the nucleotides at positions 2 and 14 from the 5' end of the first strand are not modified with a 2' O-methyl modification, and the nucleotides on the second strand which correspond to position 11, or 13, or 11 and 13, or 11-13 of the first strand are modified with a 2' fluoro modification.

A nucleic acid as disclosed herein, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are not modified with a 2' O-methyl modification A nucleic acid as disclosed herein, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are modified with a 2' fluoro modification.

A nucleic acid as disclosed herein wherein greater than 50% of the nucleotides of the first and/or second strand comprise a 2' O-methyl modification, such as greater than 55%, 60%, 65%, 70%, 75%, 80%, or 85%, or more, of the first and/or second strand comprise a 2' O-methyl modification, preferably measured as a percentage of the total nucleotides of both the first and second strands.

A nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification, preferably measured as a percentage of the total nucleotides of both the first and second strands. Suitable naturally occurring modifications include, as well as 2O' methyl, other 2' sugar modifications, in particular a 2' H modification resulting in a DNA nucleotide.

A nucleic acid as disclosed herein comprising no more than 20%, such as no more than 15% such as more than 10%, of nucleotides which have 2' modifications that are not 2' O methyl modifications on the first and/or second strand, preferably as a percentage of the total nucleotides of both the first and second strands.

A nucleic acid as disclosed herein comprising no more than 20%, (such as no more than 15% or no more than 10%) of 2' fluoro modifications on the first and/or second strand, preferably as a percentage of the total nucleotides of both strands.

A nucleic acid as disclosed herein, wherein all nucleotides are modified with a 2' O-methyl modification except positions 2 and 14 from the 5' end of the first strand and the nucleotides on the second strand which correspond to position 11, or 13, or 11 and 13, or 11-13 of the first strand. Preferably the nucleotides that are not modified with 2' O-methyl are modified with fluoro at the 2' position.

Preferred is a nucleic acid as disclosed herein wherein all nucleotides of the nucleic acid are modified at the 2' position of the sugar. Preferably these nucleotides are modified with a 2'-fluoro modification where the modification is not a 2' O-Methyl modification.

Nucleic acids of the invention may comprise one or more nucleotides modified at the 2' position with a 2' H, and therefore having a DNA nucleotide within the nucleic acid. Nucleic acids of the invention may comprise DNA nucleotides at positions 2 and/or 14 of the first strand counting from the 5' end of the first strand. Nucleic acids may comprise DNA nucleotides on the second strand which correspond to position 11, or 13, or 11 and 13, or 11-13 of the first strand.

In one aspect there is no more than one DNA per nucleic acid of the invention.

Nucleic acids of the invention may comprise one or more LNA nucleotides. Nucleic acids of the invention may comprise LNA nucleotides at positions 2 and/or 14 of the first strand counting from the 5' end of the first strand. Nucleic acids may comprise LNA on the second strand which correspond to position 11, or 13, or 11 and 13, or 11-13 of the first strand.

Preferably the nucleic acid as disclosed herein is an SiRNA.

In one aspect the nucleic acid is modified on the first strand with alternating 2-0 methyl modifications and 2 fluoro modifications, and positions 2 and 14 (starting from the 5' end) are modified with 2' fluoro. Preferably the second strand is modified with 2' fluoro modifications at nucleotides on the second strand which correspond to position 11, or 13, or 11 and 13, or 11-13 of the first strand. Preferably the second strand is modified with 2' fluoro modifications at positions 11-13 counting from the 3' end starting at the first position of the complementary (double stranded) region, and the remaining modifications are naturally occurring modifications, preferably 2' O-methyl.

In one aspect the nucleic acid of the invention comprise one or more inverted ribonucleotides, preferably an inverted adenine, using a 5'-5' linkage or a 3'-3' linkage, preferably a 3'-3' linkage at the 3' end of the second strand.

In one aspect the nucleic acid comprises one or more phosphorodithioate linkages, such as 1, 2, 3 or 4 phosphorodithioate linkages. Preferably there are up to 4 phosphorodithioate linkages, one each at the 5' and 3' ends of the first and second strands.

All the features of the nucleic acids can be combined with all other aspects of the invention disclosed herein.

In particular, preferred are nucleic acids which are SiRNA molecules wherein the nucleotides at positions 2 and 14 from the 5' end of the first strand are not modified with a 2' O-methyl modification, and the nucleic acid comprises one or more or all of:
(i) an inverted nucleotide, preferably a 3'-3' linkage at the 3' end of the second strand;
(ii) one or more phosphorodithioate linkages;
(iii) the second strand nucleotide corresponding to position 11 or 13 of the first strand is not modified with a 2' O-methyl modification, preferably wherein one or both of these positions comprise a 2' fluoro modification
(iv) the nucleic acid comprises at least 80% of all nucleotides having a 2'-O-methly modification
(v) the nucleic acid comprises no more than 20% of nucleotides which have 2' fluoro modifications.

Also provided by the present invention is a nucleic acid as disclosed herein, wherein the nucleotides at positions 2 and 14 from the 5' end of the first strand and the nucleotides at positions 7 and/or 9, or 7-9 from the 5' end of the second strand are modified with a 2' fluoro modification, and at least 90% of the remaining nucleotides are 2'-0 methyl modified or comprise another naturally occurring 2' modification.

Specific preferred examples, for a blunt double stranded 19 base nucleic acid, with no overhang, are:

A nucleic acid as disclosed herein, wherein the nucleotides at positions 2 and 14 from the 5' end of the first strand are not modified with a 2' O-methyl modification, and the nucleotide at position 7 from the 5' end of the second strand is not modified with a 2' O-methyl modification.

A nucleic acid as disclosed herein, wherein the nucleotides at positions 2 and 14 from the 5' end of the first strand are not modified with a 2' O-methyl modification, and the nucleotide at position 9 from the 5' end of the second strand is not modified with a 2' O-methyl modification A nucleic acid as disclosed herein, wherein the nucleotides at positions 2 and 14 from the 5' end of the first strand are not modified with a 2' O-methyl modification, and the nucleotides at position 7 and 9 from the 5' end of the second strand are not modified with a 2' O-methyl modification.

A nucleic acid as disclosed herein, wherein the nucleotides at positions 2 and 14 from the 5' end of the first strand are not modified with a 2' O-methyl modification, and the nucleotides at positions 7-9 from the 5' end of the second strand are not modified with a 2' O-methyl modification.

A nucleic acid as disclosed herein, wherein the nucleotides at positions 2 and 14 from the 5' end of the first strand are not modified with a 2' O-methyl modification, and the nucleotides at positions 7 and/or 9, or 7-9 from the 5' end of the second strand are modified with a 2' fluoro modification.

A nucleic acid as disclosed herein, wherein the nucleotides at positions 2 and 14 from the 5' end of the first strand are modified with a 2' fluoro modification, and the nucleotides at positions 7 and/or 9, or 7-9 from the 5' end of the second strand are not modified with a 2' O-methyl modification A nucleic acid as disclosed herein, wherein the nucleotides at positions 2 and 14 from the 5' end of the first strand are modified with a 2' fluoro modification, and the nucleotides at positions 7 and/or 9, or 7-9 from the 5' end of the second strand are modified with a 2' fluoro modification.

A nucleic acid as disclosed herein wherein greater than 50% of the nucleotides of the first and/or second strand comprise a 2' O-methyl modification, such as greater than 55%, 60%, 65%, 70%, 75%, 80%, or 85%, or more, of the first and/or second strand comprise a 2' O-methyl modification, preferably measured as a percentage of the total nucleotides of both the first and second strands.

A nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification, preferably measured as a percentage of the total nucleotides of both the first and second strands. Suitable naturally occurring modifications include, as well as 2O' methyl, other 2' sugar modifications, in particular a 2' H modification resulting in a DNA nucleotide.

A nucleic acid as disclosed herein comprising no more than 20%, such as no more than 15% such as more than 10%, of nucleotides which have 2' modifications that are not 2' O methyl modifications on the first and/or second strand, preferably as a percentage of the total nucleotides of both the first and second strands.

A nucleic acid as disclosed herein comprising no more than 20%, (such as no more than 15% or no more than 10%)

of 2' fluoro modifications on the first and/or second strand, preferably as a percentage of the total nucleotides of both strands.

A nucleic acid as disclosed herein, wherein all nucleotides are modified with a 2' O-methyl modification except positions 2 and 14 from the 5' end of the first strand and the nucleotides at positions 7 and/or 9 from the 5' end of the second strand. Preferably the nucleotides that are not modified with 2' O-methyl are modified with fluoro at the 2' position.

A nucleic acid as disclosed herein, wherein all nucleotides are modified with a 2' O-methyl modification except positions 2 and 14 from the 5' end of the first strand and the nucleotides at positions 7-9 from the 5' end of the second strand. Preferably the nucleotides that are not modified with 2' O-methyl are modified with fluoro at the 2' position.

For a nucleic acid comprising a 20 base pair duplex region, the second strand preferably does not have a 2' O-methyl group at nucleotides 8 or 9 or 10 counting from the 5' end of the duplex corresponding to positions 13, 12, and 11 of the first strand respectively.

For a nucleic acid comprising a 21 base pair duplex region, the second strand preferably does not have a 2' O-methyl group at nucleotides 9 or 10 or 11 counting from the 5' end of the duplex corresponding to positions 13, 12, and 11 of the first strand respectively.

In one aspect the nucleic acid is not any one or more or all of Patisiran, Revusiran, Fitusiran, Cemdisiran, Givosiran, Inclisiran, lumasiran, Votrisiran, Cosdosiran and Teprasiran.

These have the sequences below.

```
Patisiran
                                        (SEQ ID NO: 302)
3'CAUUGGUUCUCAUAAGGUA 5'

(SEQ ID NO: 303)
5'GUAACCAAGAGUAUUCCAU 3'

Revusiran
                                        (SEQ ID NO: 304)
3'-CUACCCUAAAGUACAUUGGUUCU-5'

(SEQ ID NO: 305)
5'-UGGGAUUUCAUGUAACCAAGA 3'

Fitusiran
                                        (SEQ ID NO: 306)
3'-GACCAAUUGUGGUAAAUGAAGUU-5'

(SEQ ID NO: 307)
5'-GGUUAACACCAUUUACUUCAA 3'

Cemdisiran
                                        (SEQ ID NO: 308)
3'-TTUUUUCGUUCUAUAAAAAUAUUAU-5'

(SEQ ID NO: 309)
5'-AAGCAAGAUAUUUUUAUAAUA 3'

Givosiran
                                        (SEQ ID NO: 310)
3'-UGGUCUUUCUCACAGAGUAGAAU 5'

(SEQ ID NO: 311)
5'-CAGAAAGAGUGUCUCAUCUUA 3'

Inclisiran
                                        (SEQ ID NO: 312)
3'-AAGAUCUGGACAAAACGAAAACA 5'

(SEQ ID NO: 313)
5'-CUAGACCUGUUUGCUUUUGU 3'
```

Sequences of these molecules are also available on the WHO website http://www.who.int/medicines/services/inn/en/

For example,

Cemdisian is duplex of [(2S,4R)-1-{1-[(2-acetamido-2-deoxy-β-Dgalactopyranosyl) oxy]-16,16-bis({3-[(5-[(2-acetamido-2-deoxy-β-D-galactopyranosyl)oxy]pentanamido}propyl) amino]-3-oxopropoxy}methyl)-5,11,18-trioxo-14-oxa-6,10, 17-triazanonacosan-29-oyl}-4-hydroxypyrrolidin-2-yl] methyl hydrogen all-P-ambo-2'-O-methyl-Pthioadenylyl-(3'→5')-2'-O-methyl-P-thioadenylyl-(3'→5')-2'-deoxy-2'-fluoroguanylyl-(3'→5')-2'-O-methylcytidylyl-(3'→5')-2'-deoxy-2'-fluoroadenylyl-(3'→5')-2'-Omethyladenylyl-(3'→5')-2'-deoxy-2'-fluoroguanylyl-(3'→5')-2'-O-methyladenylyl-(3'→5')-2'-deoxy-2'-fluorouridylyl-(3'→5')-2'-deoxy-2'-fluoroadenylyl-(3'→5')-2'-deoxy-2'-fluorouridylyl-(3'→5')-2'-O-methyluridylyl-(3'→5')-2'-deoxy-2'-fluorouridylyl-(3'→5')-2'-O-methyluridylyl-(3'→5')-2'-Omethyluridylyl-(3'→5')-2'-deoxy-2'-fluoroadenylyl-(3'→5')-2'-O-methyluridylyl-(3'→5')-2'-deoxy-2'-fluoroadenylyl-(3'→5')-2'-O-methyladenylyl-(3'→5')-2'-O-methyluridylyl-(3'→5')-2'-O-methyl-3'-adenylate and all-P-ambo-thymidylyl-(5'→3')-thymidylyl-(5'→3')-2'-O-methyl-P-thioadenylyl-(5'→3')-2'-Omethyl-P-thiouridylyl-(5'→3')-2'-O-methyluridylyl-(5'→3')-2'-Omethyluridylyl-(5'→3')-2'-O-methylcytidylyl-(5'→3')-2'-deoxy-2'-fluoroguanylyl-(5'→3')-2'-O-methyluridylyl-(5'→3')-2'-deoxy-2'-fluorouridylyl-(5'→3')-2'-Omethylcytidylyl-(5'→3')-2'-deoxy-2'-fluorouridylyl-(5'→3')-2'-O-methyladenylyl-(5'→3')-2'-O-methyluridylyl-(5'→3')-2'-O-methyladenylyl-(5'→3')-2'-deoxy-2'-fluoroadenylyl-(5'→3')-2'-O-methyladenylyl-(5'→3')-2'-deoxy-2'-fluoroadenylyl-(5'→3')-2'-O-methyladenylyl-(5'→3')-2'-Omethyluridylyl-(5'→3')-2'-deoxy-2'-fluoroadenylyl-(5'→3')-2'-O-methyluridylyl-(5'→3')-2'-deoxy-2'-fluoro-P-thiouridylyl-(5'→3')-2'-deoxy-2'-fluoro-P-thioadenylyl-(5'→3')-2'-Omethyluridine Patisiran is RNA duplex of guanylyl-(3'→5')-2'-O-methyluridylyl-(3'→5')-adenylyl-(3'→5')-adenylyl-(3'→5')-2'-O-methylcytidylyl-(3'→5')-2'-Omethylcytidylyl-(3'→5')-adenylyl-(3'→5')-adenylyl-(3'→5')-guanylyl-(3'→5')-adenylyl-(3'→5')-guanylyl-(3'→5')-2'-O-methyluridylyl-(3'→5')-adenylyl-(3'→5')-2'-O-methyluridylyl-(3'→5')-2'-Omethyluridylyl-(3'→5')-2'-O-methylcytidylyl-(3'→5')-2'-Omethylcytidylyl-(3'→5')-adenylyl-(3'→5')-2'-O-methyluridylyl-(3'→5')-thymidylyl-(3'→5')-thymidine with thymidylyl-(5'→3')-thymidylyl-(5'→3')-cytidylyl-(5'→3')-adenylyl-(5'→3')-2'-O-methyluridylyl-(5'→3')-uridylyl-(5'→3')-guanylyl-(5'→3')-guanylyl-(5'→3')-uridylyl-(5'→3')-uridylyl-(5'→3')-cytidylyl-(5'→3')-uridylyl-(5'→3')-cytidylyl-(5'→3')-adenylyl-(5'→3')-2'-O-methyluridylyl-(5'→3')-adenylyl-(5'→3')-adenylyl-(5'→3')-guanylyl-(5'→3')-guanylyl-(5'→3')-uridylyl-(5'→3')-adenosine Inclisiran is duplex of [(2S,4R)-1-{1-[(2-acetamido-2-deoxy-β-Dgalactopyranosyl) oxy]-16,16-bis({3-[(3-{5-[(2-acetamido-2-deoxy-β-D-galactopyranosyl)oxy]pentanamido} propyl) amino]-3-oxopropoxy}methyl)-5,11,18-trioxo-14-oxa-6,10, 17-triazanonacosan-29-oyl}-4-hydroxypyrrolidin-2-yl] methyl hydrogen all-P-ambo-2'-O-methyl-Pthiocytidylyl-(3'→5')-2'-O-methyl-P-thiouridylyl-(3'→5')-2'-Omethyladenylyl-(3'→5')-2'-O-methylguanylyl-(3'→5')-2'-Omethyladenylyl-(3'→5')-2'-O-methylcytidylyl-(3'→5')-2'-deoxy-2'-fluorocytidylyl-(3'→5')-2'-O-methyluridylyl- (3'→5')-2'-deoxy-2'-fluoroguanylyl-(3'→5')-2'-O-methyluridylyl-(3'→5')-thymidylyl-(3'→5')-2'-O-methyluridylyl-(3'→5')-2'-Omethyluridylyl-(3'→5')-2'-O-methylguanylyl-(3'→5')-2'-Omethylcytidylyl-(3'→5')-2'-O-methyluridylyl-(3'→5')-2'-Omethyluridylyl-(3'→5')-2'-O-methyluridylyl-(3'→5')-2'-Omethyluridylyl-(3'→5')-2'-O-methylguanylyl-(3'→5')-2'-Omethyl-3'-uridylate and all-P-ambo-2'-O-methyl-P-thioadenylyl-(5'→3')-2'-O-methyl-P-thioadenylyl-(5'→3')-2'-O-methylguanylyl-(5'→3')-2'-O-methyladenylyl-(5'→3')-2'-O-methyluridylyl-(5'→3')-2'-deoxy-2'-fluorocytidylyl-(5'→3')-2'-O-methyluridylyl-(5'→3')-2'-deoxy-2'-fluoroguanylyl-(5'→3')-2'-O-methylguanylyl-(5'→3')-2'-deoxy-2'-fluoroadenylyl-(5'→3')-2'-O-methylcytidylyl-(5'→3')-2'-deoxy-2'-fluoroadenylyl-(5'→3')-2'-Omethyladenylyl-(5'→3')-2'-deoxy-2'-fluoroadenylyl-(5'→3')-2'-O-methyladenylyl-(5'→3')-2'-deoxy-2'-fluorocytidylyl-(5'→3')-2'-O-methylguanylyl-(5'→3')-2'-deoxy-2'-fluoroadenylyl-(5'→3')-2'-deoxy-2'-fluoroadenylyl-(5'→3')-2'-deoxy-2'-fluoroadenylyl-(5'→3')-2'-O-methyl-P-thioadenylyl-(5'→3')-2'-deoxy-2'-fluoro-P-thiocytidylyl-(5'→3')-2'-O-methyladenosine Givosiran is
duplex of [(2S,4R)-1-{1-[(2-acetamido-2-deoxy-β-Dgalactopyranosyl) oxy]-16,16-bis({3-[(3-{5-[(2-acetamido-2-deoxy-β-D-galactopyranosyl)oxy]pentanamido}propyl)amino]-3-oxopropoxy}methyl)-5,11,18-trioxo-14-oxa-6,10,17-triazanonacosan-29-oyl}-4-hydroxypyrrolidin-2-yl] methyl hydrogen all-P-ambo-2'-O-methyl-P-thiocytidylyl-(3'→5')-2'-O-methyl-P-thioadenylyl-(3'→5')-2'-Omethylguanylyl-(3'→5')-2'-O-methyladenylyl-(3'→5')-2'-Omethyladenylyl-(3'→5')-2'-O-methyladenylyl-(3'→5')-2'-deoxy-2'-fluoroguanylyl-(3'→5')-2'-O-methyladenylyl-(3'→5')-2'-deoxy-2'-fluoroguanylyl-(3'→5')-2'-Omethyluridylyl-(3'→5')-2'-deoxy-2'-fluoroguanylyl-(3'→5')-2'-O-methyluridylyl-(3'→5')-2'-deoxy-2'-fluorocytidylyl-(3'→5')-2'-O-methyluridylyl-(3'→5')-2'-deoxy-2'-fluorocytidylyl-(3'→5')-2'-O-methyladenylyl-(3'→5')-2'-O-methyluridylyl-(3'→5')-2'-O-methylcytidylyl-(3'→5')-2'-O-methyluridylyl-(3'→5')-2'-O-methyluridylyl-(3'→5')-2'-O-methyl-3'-adenylate and all-P-ambo-2'-O-methyl-P-thiouridylyl-(5'→3')-2'-O-methyl-P-thioguanylyl-(5'→3')-2'-Omethylguanylyl-(5'→3')-2'-deoxy-2'-fluorouridylyl-(5'→3')-2'-O-methylcytidylyl-(5'→3')-2'-deoxy-2'-fluorouridylyl-(5'→3')-2'-O-methyluridylyl-(5'→3')-2'-deoxy-2'-fluorouridylyl-(5'→3')-2'-O-methylcytidylyl-(5'→3')-2'-deoxy-2'-fluorouridylyl-(5'→3')-2'-O-methylcytidylyl-(5'→3')-2'-deoxy-2'-fluoroadenylyl-(5'→3')-2'-Omethylcytidylyl-(5'→3')-2'-deoxy-2'-fluoroadenylyl-(5'→3')-2'-O-methylguanylyl-(5'→3')-2'-deoxy-2'-fluoroadenylyl-(5'→3')-2'-O-methylguanylyl-(5'→3')-2'-deoxy-2'-fluorouridylyl-(5'→3')-2'-O-methyladenylyl-(5'→3')-2'-deoxy-2'-fluoroguanylyl-(5'→3')-2'-deoxy-2'-fluoro-P-thioadenylyl-(5'→3')-2'-deoxy-2'-fluoro-P-thioadenylyl-(5'→3')-2'-O-methyluridine Revusiran is
[(2S,4R)-1-{30-(2-acetamido-2-deoxy-β-D-galactopyranosyl)-14,14-bis[16-(2-acetamido-2-deoxy-β-Dgalactopyranosyl)-5,11-dioxo-2,16-dioxa-6,10-diazahexadecyl]-12,19,25-trioxo-16,30-dioxa-13,20,24-triazatriacontanoyl}-4-hydroxypyrrolidin-2-yl]methyl hydrogen 2'-deoxy-2'-fluorouridylyl-(3'→5')-2'-O-methylguanylyl-(3'→5')-2'-deoxy-2'-fluoroguanylyl-(3'→5')-2'-O-methylguanylyl-(3'→5')-2'-deoxy-2'-fluoroadenylyl-(3'→5')-2'-O-methyluridylyl-(3'→5')-2'-deoxy-2'-fluorouridylyl-(3'→5')-2'-O-methyluridylyl-(3'→5')-2'-deoxy-2'-fluorocytidylyl-(3'→5')-2'-deoxy-2'-fluoroadenylyl-(3'→5')-2'-deoxy-2'-fluorouridylyl-(3'→5')-2'-O-methylguanylyl-(3'→5')-2'-deoxy-2'-fluorouridylyl-(3'→5')-2'-O-methyladenylyl-(3'→5')-2'-O-methylcytidylyl-(3'→5')-2'-deoxy-2'-fluorocytidylyl-(3'→5')-2'-O-methyladenylyl-(3'→5')-2'-deoxy-2'-fluoroadenylyl-(3'→5')-2'-O-methylguanylyl-(3'→5')-2'-deoxy-2'-fluoroadenylate duplex with 2'-O-methyl-Pthiocytidylyl-(5'→3')-2'-deoxy-2'-fluoro-P-thiouridylyl-(5'→3')-2'-O-methyladenylyl-(5'→3')-2'-deoxy-2'-fluorocytidylyl-(5'→3')-2'-O-methylcytidylyl-(5'→3')-2'-deoxy-2'-fluorocytidylyl-(5'→3')-2'-O-methyluridylyl-(5'→3')-2'-deoxy-2'-fluoroadenylyl-(5'→3')-2'-O-methyladenylyl-(5'→3')-2'-deoxy-2'-fluoroadenylyl-(5'→3')-2'-O-methylguanylyl-(5'→3')-2'-O-methyluridylyl-(5'→3')-2'-Omethyladenylyl-(5'→3')-2'-deoxy-2'-fluorocytidylyl-(5'→3')-2'-Omethyladenylyl-(5'→3')-2'-deoxy-2'-fluorouridylyl-(5'→3')-2'-deoxy-2'-fluorouridylyl-(5'→3')-2'-deoxy-2'-fluoroguanylyl-(5'→3')-2'-O-methylguanylyl-(5'→3')-2'-deoxy-2'-fluorouridylyl-(5'→3')-2'-O-methyluridylyl-(5'→3')-2'-deoxy-2'-fluorocytidylyl-(5'→3')-2'-O-methyluridine Fitusiran is
duplex of [(2S,4R)-1-{30-(2-acetamido-2-deoxy-β-Dgalactopyranosyl)-14,14-bis[16-(2-acetamido-2-deoxy-β-Dgalactopyranosyl)-5,11-dioxo-2,16-dioxa-6,10-diazahexadecyl]-12,19,25-trioxo-16,30-dioxa-13,20,24-triazatriacontanoyl}-4-hydroxypyrrolidin-2-yl]methyl hydrogen (P—RS)-2'-deoxy-2'-fluoro-P-thioguanylyl-(3'→5')-(P—RS)-2'-O-methyl-P-thioguanylyl-(3'→5')-2'-deoxy-2'-fluorouridylyl-(3'→5')-2'-O-methyluridylyl-(3'→5')-2'-deoxy-2'-fluoroadenylyl-(3'→5')-2'-O-methyladenylyl-(3'→5')-2'-deoxy-2'-fluorocytidylyl-(3'→5')-2'-O-methyladenylyl-(3'→5')-2'-deoxy-2'-fluorocytidylyl-(3'→5')-2'-deoxy-2'-fluorocytidylyl-(3'→5')-2'-deoxy-2'-fluoroadenylyl-(3'→5')-2'-O-methyluridylyl-(3'→5')-2'-deoxy-2'-fluorouridylyl-(3'→5')-2'-O-methyluridylyl-(3'→5')-2'-deoxy-2'-fluorouridylyl-(3'→5')-2'-O-methyluridylyl-(3'→5')-2'-deoxy-2'-fluorocytidylyl-(3'→5')-2'-O-methyladenylyl-(3'→5')-2'-deoxy-2'-fluoroadenylate and and (P—RS)-2'-O-methyl-P-thiouridylyl-(3'→5')-(P—RS)-2'-deoxy-2'-fluoro-P-thiouridylyl-(3'→5')-2'-O-methylguanylyl-(3'→5')-2'-deoxy-2'-fluoroadenylyl-(3'→5')-2'-Omethyladenylyl-(3'→5')-2'-deoxy-2'-fluoroguanylyl-(3'→5')-2'-O-methyluridylyl-(3'→5')-2'-deoxy-2'-fluoroadenylyl-(3'→5')-2'-O-methyladenylyl-(3'→5')-2'-deoxy-2'-fluoroadenylyl-(3'→5')-2'-O-methyluridylyl-(3'→5')-2'-Omethylguanylyl-(3'→5')-2'-O-methylguanylyl-(3'→5')-2'-deoxy-2'-fluorouridylyl-(3'→5')-2'-Omethylguanylyl-(3'→5')-2'-deoxy-2'-fluorouridylyl-(3'→5')-2'-O-methyluridylyl-(3'→5')-2'-deoxy-2'-fluoroadenylyl-(3'→5')-2'-Omethyladenylyl-(3'→5')-2'-deoxy-2'-fluorocytidylyl-(3'→5')-(P—RS)-2'-O-methyl-P-thiocytidylyl-(3'→5')-(P—RS)-2'-Omethyl-P-thioadenylyl-(3'→5')-2'-O-methylguanosine Lumasiran is
{(2S,4R)-1-{1-[(2-acetamido-2-deoxy-β-Dgalactopyranosyl) oxy]-16,16-bis-(13-[(3-{5-[(2-acetamido-2-deoxy-β-Dgalactopyranosyl) oxy]pentanamido}propyl)amino]-3-oxopropoxy}methyl)-5,11,18-trioxo-14-oxa-6,10,17-triazanonacosan-29-oyl}-4-hydroxypyrrolidin-2-yl}methyl hydrogen all-P-ambo-2'-O-methyl-P-thioguanylyl-(3'→5')-2'-O-methyl-P-thioadenylyl-(3'→5')-2'-O-methylcytidylyl-(3'→5')-2'-O-methyluridylyl-(3'→5')-2'-O-methyluridylyl-(3'→5')-2'-O-methyluridylyl-(3'→5')-2'-deoxy-2'- fluorocytidylyl-(3'→5')-2'-O-methyladenylyl-(3'→5')-2'-deoxy-2'-fluorouridylyl-(3'→5')-2'-deoxy-2'-fluorocytidylyl-(3'→5')-2'-deoxy-2'-fluorocytidylyl-(3'→5)-2'-Omethyluridylyl-(3'→5')-2'-O-methylguanylyl-(3'→5')-2'-Omethylguanylyl-(3'→5')-2'-O-methyladenylyl-(3'→5')-2'-Omethyladenylyl-(3'→5')-2'-O-methyladenylyl-(3'→5')-2'-Omethyluridylyl-(3'→5')-2'-O-methyladenylyl-(3'→5')-2'-Omethyluridylyl-(3'-5')-2'-O-methyl-3'-adenylate duplex with all-P-ambo-2'-O-methyl-P-thioadenylyl-(5'→3')-2'-O-methyl-P-thiocytidylyl-(5'→3')-2'-O-methylcytidylyl-(5'→3')-2'-O-methyluridylyl-(5'→3')-2'-O-methylguanylyl-(5'→3')-2'-O-methyladenylyl-(5'→3')-2'-O-methyladenylyl-(5'→3')-2'-deoxy-2'-fluoroadenylyl-(5'→3')-2'-Omethylguanylyl-(5'→3')-2'-deoxy-2'-fluorouridylyl-(5'→3')-2'-O-methyladenylyl-(5'→3')-2'-O-methylguanylyl-(5'→3')-2'-O-methylguanylyl-(5'→3')-2'-O-methyladenylyl-(5'→3')-2'-deoxy-2'-fluorocytidylyl-(5'→3')-2'-deoxy-2'-fluorocytidylyl-(5'→3')-2'-O-methyluridylyl-(5'→3')-2'-deoxy-2'-fluorouridylyl-(5'→3')-2'-O-methyluridylyl-(5'→3')-2'-Omethyladenylyl-(5'→3')-2'-O-methyl-P-thiouridylyl-(5'→3')-2'-deoxy-2'-fluoro-P-thioadenylyl-(5'→3')-2'-Omethyluridine

SEQ ID NO: 316

(3-5) G=A=C-U-U-C-A-U-C-C-U-G-G-A-A-A-U-A-U-A- (R1)
 · · · · · · · · · · · · · · · · · · ·
(5'-3') A=C=C-U-G-A-A-A-G-U-A-G-G-A-C-C-U-U-U-A-U=A=U

SEQ ID NO: 317

X: 2'-deoxy-2'-fluoro-X/X: 2'-désoxy-2'-fluoro-X
X: 2'-O-methyl-X/X: 2'-O-méthyl-X

— : P(=O)(OH)(O)
= : P(=O)(SH)(O)

R1— = R-NH-C(R)(R)-C(=O)-NH-...-C(=O)-N(pyrrolidine-CH₂—, OH)

R— = (GalNAc-O-CH₂CH₂CH₂-C(=O)-NH-CH₂CH₂CH₂-NH-C(=O)-CH₂CH₂-O-CH₂—)

Votrisiran is:
{(2S,4R)-1-{1-[(2-acetamido-2-deoxy-β-Dgalactopyranosyl) oxy]-16,16-bis-(13-[(3-{5-[(2-acetamido-2-deoxy-β-Dgalactopyranosyl) oxy]pentanamido}propyl)amino]-3-oxopropoxy}methyl)-5,11,18-trioxo-14-oxa-6,10,17-triazanonacosan-29-oyl}-4-hydroxypyrrolidin-2-yl}methyl hydrogen all-P-ambo-2'-O-methyl-P-thiouridylyl-(3'→5')-2'-O-methyl-P-thioguanylyl-(3'→5')-2'-O-methylguanylyl-(3'→5')-2'-O-methylguanylyl-(3'→5')-2'-O-methyladenylyl-(3'→5')-2'-O-methyluridylyl-(3'→5')-2'-deoxy-2'-fluorouridylyl-(3'→5')-2'-O-methyluridylyl-(3'→5')-2'-deoxy-2'-fluorocytidylyl-(3'→5')-2'-deoxy-2'-fluoroadenylyl-(3'→5')-2'-deoxy-2'-fluorouridylyl-(3'→5')-2'-O-methylguanylyl-(3'→5')-2'-O-methyluridylyl-(3'→5')-2'-O-methyladenylyl-(3'→5')-2'-O-methyladenylyl-(3'→5')-2'-O-methyladenylyl-(3'→5')-2'-O-methylcytidylyl-(3'→5')-2'-O-methylcytidylyl-(3'→5')-2'-O-methyladenylyl-(3'→5')-2'-O-methyladenylyl-(3'→5')-2'-O-methylguanylyl-(3'→5')-2'-O-methyl-3'-adenylate duplex with all-P-ambo-2'-O-methyl-P-thiocytidylyl-(5'→3')-2'-O-methyl-P-thiouridylyl-(5'→3')-2'-O-methyladenylyl-(5'→3')-2'-O-methylcytidylyl-(5'→3')-2'-O-methylcytidylyl-(5'→3')-2'-O-methylcytidylyl-(5'→3')-2'-O-methyluridylyl-(5'→3')-2'-deoxy-2'-fluoroadenylyl-(5'→3')-2'-O-methyladenylyl-(5'→3')-2'-deoxy-2'-fluoroadenylyl-(5'→3')-2'-O-methylguanylyl-(5'→3')-2'-O-methyluridylyl-(5'→3')-2'-O-methyladenylyl-(5'→3')-2'-O-methylcytidylyl-(5'→3')-2'-deoxy-2'-fluoroadenylyl-(5'→3')-2'-O-methyluridylyl-(5'→3')-2'-Omethyluridylyl-(5'→3')-2'-deoxy-2'-fluoroguanylyl-(5'→3')-2'-O-methylguanylyl-(5'→3')-2'-O-methyluridylyl-(5'→3')-2'-Omethyl-P-thiouridylyl-(5'→3')-2'-deoxy-2'-fluoro-Pthiocytidylyl-(5'→3')-2'-O-methyluridine

SEQ ID NO: 318

(3'-5') U=G=G-G-A-U-U-U-C-A-U-
 · · · · · · · · · · ·
(5'-3') C=U=A=C-C-C-U-A-A-A-G-U-A-
          G-U-A-C-C-A-A-G-A- (R1)
          C-A-U-G-G-U-U=C=U

SEQ ID NO: 319

X: 2'deoxy-2'-fluoro-X/X: 2'-désoxy-2'-fluoro-X
X: 2'-O-methyl-X/X: 2'-O-méthyl-X

— : P(=O)(OH)(O)
= : P(=O)(SH)(O)

R1— = R-NH-C(R)(R)-C(=O)-N(pyrrolidine-CH₂—, OH)

R— = (GalNAc-O-CH₂CH₂CH₂-C(=O)-NH-CH₂CH₂CH₂-NH-C(=O)-CH₂CH₂-O-CH₂—)

Cosdosiran is:
adenylyl-(3'→5')-2'-O-methylguanylyl-(3'→5')-guanylyl-(3'→5')-2'-O-methyladenylyl-(3'→5')-guanylyl-(3'→5')-2'-Omethyluridylyl-(3'→5')-uridylyl-(3'→5')-2'-O-methylcytidylyl-(3'→5')-cytidylyl-(3'→5')-adenylyl-(3'→5')-2'-Omethylcytidylyl-(3'→5')-adenylyl-(3'→5')-2'-Omethyluridylyl-(3'→5')-uridylyl-(3'→5')-2'-O-methylcytidylyl-(3'→5')-uridylyl-(3'→5')-2'-O-methylguanylyl-(3'→5')-guanylyl-(3'→5')-2'-O-methylcytidine duplex with [(2R,3S)-3-hydroxyoxolan-2-yl]methyl hydrogen uridylyl-(5'→3')-2'-deoxycytidylyl-(5'→3')-cytidylyl-(5'→3')-uridylyl-(5'→3')-cytidylyl-(5'→3')-adenylyl-(5'→3')-adenylyl-(5'→3')-guanylyl-(5'→3')-guanylyl-(5'→3')-uridylyl-(5'→3')-guanylyl-(5'→3')-uridylyl-(5'→3')-adenylyl-(5'→3')-adenylyl-(5'→3')-guanylyl-(5'→3')-adenylyl-(5'→3')-cytidylyl-(5'→3')-cytidylyl-(5'→3')-5'-guanylate Teprasiran is:
guanylyl-(3'→5')-2'-O-methyladenylyl-(3'→5')-guanylyl-(3'→5')-2'-O-methyladenylyl-(3'→5')-adenylyl-(3'→5')-2'-

Omethyluridylyl-(3'→5')-adenylyl-(3'→5')-2'-O-methyluridylyl-(3'→5')-uridylyl-(3'→5')-2'-O-methyluridylyl-(3'→5')-cytidylyl-(3'→5')-2'-O-methyladenylyl-(3'→5')-cytidylyl-(3'→5')-2'-O-methylcytidylyl-(3'→5')-cytidylyl-(3'→5')-2'-Omethyluridylyl-(3'→5')-uridylyl-(3'→5')-2'-O-methylcytidylyl-(3'→5')-adenosine duplex with 2'-O-methyluridylyl-(3'→5')-guanylyl-(3'→5')-2'-O-methyladenylyl-(3'→5')-adenylyl-(3'→5')-2'-O-methylguanylyl-(3'→5')-guanylyl-(3'→5')-2'-Omethylguanylyl-(3'→5')-uridylyl-(3'→5')-2'-Omethylguanylyl-(3'-5')-adenylyl-(3'-5')-2'-Omethyladenylyl-(3'-5')-adenylyl-(3'-5')-2'-Omethyluridylyl-(3'→5')-adenylyl-(3'→5')-2'-O-methyluridylyl-(3'→5')-uridylyl-(3'→5')-2'-O-methylcytidylyl-(3'→5')-uridylyl-(3'→5')-2'-O-methylcytidine Screening Method The present invention relates to a method for selecting an siRNA molecule having RNAi [RNA interference] activity, the method comprising the steps of
(1) modification of a nucleotide on the second (sense) strand which corresponds to position 11 or 13 of the first (antisense) strand to introduce a 2' O methyl modification on the nucleotide sugar,
(2) determining whether the 2' O methyl modification reduces the activity of the siRNA compared with an siRNA differing only in that there is no modification at that 2' position, or having a 2' fluoro modification at the same nucleotide; and
(3) if the modification affects SiRNA activity, select a molecule which does not have a modification which is a 2' O methyl modification at the position which reduces activity of the siRNA, and/or modify the 2' position of the nucleotide with 2 fluoro, or use an unmodified nucleotide at that position.

A method for selecting an siRNA molecule having RNAi [RNA interference] activity, the method comprising the steps of
(1) modification of a nucleotide on the second (sense) strand which corresponds to position 11 or 13 of the first (antisense) strand to introduce a nucleotide having a modification other than a 2' fluoro modification on the nucleotide sugar,
(2) determining whether the modification reduces the activity of the siRNA compared with an siRNA differing only in that there is no modification at that 2' position, or having a 2' fluoro modification at the same nucleotide; and
(3) if the modification affects siRNA activity, select a molecule which does not have that modification which reduces activity of the siRNA, and/or modify the 2' position of the nucleotide with 2' fluoro modification, or use an unmodified nucleotide at that position of the siRNA.

In another aspect, the method involves a method as above, but the modification of a nucleotide on the second (sense) strand which corresponds to position 11 or 13 of the first (antisense) introduces a modification at the 2' position which is bulky, such as a modification that is bulkier than fluoro or an unmodified RNA nucleotide, and the assessment on siRNA activity is made in respect of that 2' bulky modification. The O-methyl modification is considered to be bulky, and in one aspect the modification is at least as bulky or large as 2 O methyl.

The modification may be a modification containing a group which is of 2'-O-(2-Methoxyethyl), 2'-O-allyl, 2'-O-DNP, 2'-CE, 2'-EA, 2'-AEM, 2'-APM and 2'-GE.

The present invention also relates to a method for selecting an siRNA molecule having RNAi [RNA interference] activity, the method comprising the steps of
1 modifying an siRNA molecule by changing the 2' position of the sugar moiety of each base to be a 2' O-methyl residue;
2 assessing activity of the SiRNA to identify positions in which 2' O-methyl modification reduces the activity of the siRNA compared with the same siRNA having a 2' fluoro modification at the same position, or compared with an siRNA having no modification at the same position; and
3 selecting an siRNA molecule modified with 2' O methyl at all positions which do not show reduced activity in step 2.

In another aspect, the method involves the method as above, but the modification of a 2' nucleotide position in step (1) introduces a modification at the 2' position which is bulky, such as a modification that is bulkier than fluoro or an unmodified RNA nucleotide, and the assessment on siRNA activity is made in respect of that 2' bulky modification. The modification may be a modification containing a group which is of 2'-O-(2-Methoxyethyl), 2'-O-allyl, 2'-O-DNP, 2'-CE, 2'-EA, 2'-AEM, 2'-APM and 2'-GE.

RNAi activity may be assessed by any method disclosed herein, or others known in the art.

The invention also relates to a method for providing an siRNA molecule, comprising formulating into a pharmaceutical composition those siRNA molecules comprising 2' O methyl modifications at all positions which do not show reduced siRNA activity vs a 2' fluoro modification at the same position. Suitably these siRNA molecules have been identified using one of the above methods. For example, the siRNA having may be linked to GalNac or other targeting ligand as described herein.

The siRNA is preferably a nucleic acid of the present invention, as described above.

In the preceding disclosure, a 2'-NH2 modification may be used as an alternative to a 2' fluoro modification in any aspect of the invention, especially in siRNA modification. A 2' fluoro modification is however more preferred.

In any aspect or embodiment of the invention described herein, the nucleic acid (or use, method, composition or any other teaching involving a nucleic acid) comprises one DNA nucleotide at position 2, or 14, counting from the 5' end of the first strand and additionally, and/or alternatively, comprises 1, 2, or 3 DNA nucleotides at positions on the second strand which correspond to any one, two or three positions 11, 12 and 13 of the first strand.

In any aspect or embodiment of the invention described herein, the nucleic acid (or use, method, composition or any other teaching involving a nucleic acid) comprises a DNA nucleotide, or a 2'fluoro modification, at a position or positions on the second strand which corresponds to positions 11-13 of the first strand. More than one modification may be present.

In any aspect or embodiment of the invention described herein, the nucleic acid—or any use, method, composition or any other teaching involving a nucleic acid herein—does not comprise a bulky modification group—such as a 2'-O methyl group—at any one of position 2, or 14, or both, counting from the 5' end of the first strand, and/or at any position of the second strand which corresponds to positions 11, 12 or 13 of the first strand. A bulky modification may be any modification that is bigger than an 'OH group, for example, at the 2' position of the RNA sugar moiety.

In further embodiments of the invention, the invention relates to any nucleic acid, conjugated nucleic acid, nucleic acid for use, method, composition or use according to any disclosure herein, wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, optionally wherein
  a. the 3' and/or 5' inverted nucleotide of the first and/or second strand is attached to the adjacent nucleotide via a phosphate group by way of a phosphodiester linkage; or
  b. the 3' and/or 5' inverted nucleotide of the first and/or second strand is attached to the adjacent nucleotide via a phosphorothioate group or
  c. the 3' and/or 5' inverted nucleotide of the first and/or second strand is attached to the adjacent nucleotide via a phosphorodithioate group.

In further embodiments of the invention, the invention relates to any nucleic acid, conjugated nucleic acid, nucleic acid for use, method, composition or use according to any disclosure herein, wherein the nucleic acid comprises a phosphorodithioate linkage, optionally wherein the linkage is between the 2 most 5' nucleosides and/or the 2 most 3' nucleosides of the second strand, and/or optionally wherein the nucleic acid additionally does not comprise any internal phosphorothioate linkages.

The invention also relates to any first strand or any second strand of nucleic acid as disclosed herein, which comprises no more than 2 base changes when compared to the specific sequence ID provided. For example, one base may be changed within any sequence.

In one embodiment, the change may be made to the 5' most nucleotide of the antisense (first) strand. In one embodiment, the change may be made to the 3' most nucleotide of the antisense (first) strand. In one embodiment, the change may be made to the 5' most nucleotide of the sense (second) strand. In one embodiment, the change may be made to the 3' most nucleotide of the sense (second) strand.

Figures 2A, 2B:
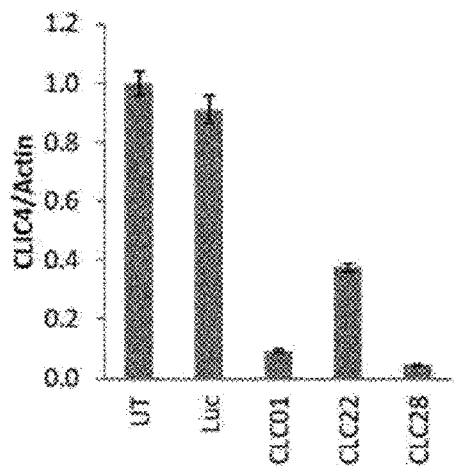
Figures 3A, 3B:
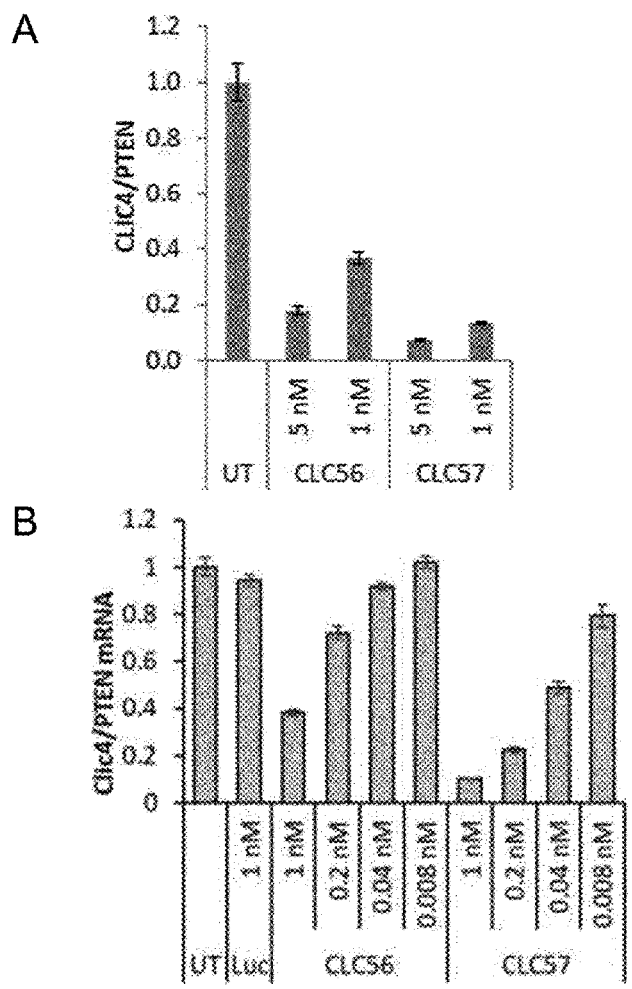
Figures 5A, 5B:
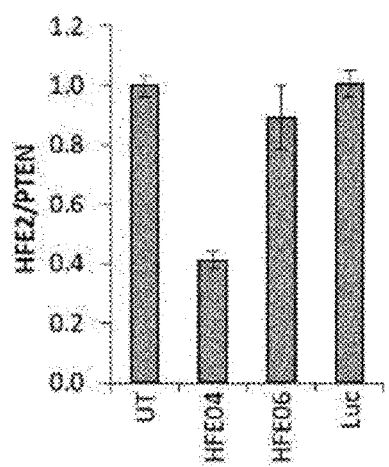

In one embodiment, the change is made to the 5' most nucleotide of the antisense (first) strand. The base of the 5' nucleotide may be changed to any other nucleotide. An A or a U at the 5' end are preferred, and an A or a U are taught herein as the potential 5' terminal base for all of the antisense sequences disclosed herein The invention will now be described with reference to the following non-limiting figures and examples in which:

FIGS. 1a and 1b show in vitro knockdown activity of siRNAs that are modified with 2'-OMe or 2'-OH at position 14 of the first strand;

FIGS. 2a and 2b show in vitro knockdown activity of siRNAs with 2'-OMe or 2'-OH at position 14 of the first strand;

FIGS. 3a and 3b show in vitro knockdown activity of siRNAs with 2'-OMe or 2'-OH at positions 2, 3 and 4 of the first strand;

FIGS. 4a and 4b show in vitro knockdown activity of siRNAs with 2'-OMe and 2'-OH at positions 2, 3 and 4 of the first strand;

FIGS. 5a and 5b show in vitro knockdown activity of siRNAs with 2'-OMe and 2'-F at position 2 of the first strand;

FIG. 6 a-c show knockdown activity of differently modified ALDH2 variants derived from one sequence;

FIGS. 7a and b show knockdown activity of differently modified ALDH2 sequences;

FIGS. 8a and b show knockdown activity of differently modified ALDH2 sequences;

FIGS. 9a and b show knockdown activity of differently modified DGAT2 sequences;

FIGS. 10a and b show the effect of DNA modifications at certain positions of a TMPRSS6 siRNA sequence;

FIGS. 11 a and b show the effect of LNA modifications at certain positions of a TMPRSS6 siRNA sequence;

FIG. 12a-d show knockdown activity of GalNAc conjugates with different modification patterns both in liposomal transfections and receptor-mediated uptake;

FIGS. 13a and b show tolerance for DNA modification at more than one position in a TMPRSS6 siRNA sequence;

FIGS. 14a and b disclose tolerance for DNA in an siRNA targeting ALDH2;

FIG. 15 and b disclose tolerance for DNA in a second siRNA targeting ALDH2;

FIGS. 16a and b disclose tolerance for DNA in an siRNA targeting DGAT2;

FIGS. 17a and b disclose the effect of 2-O-MOE at certain positions; and

Figure 18B:
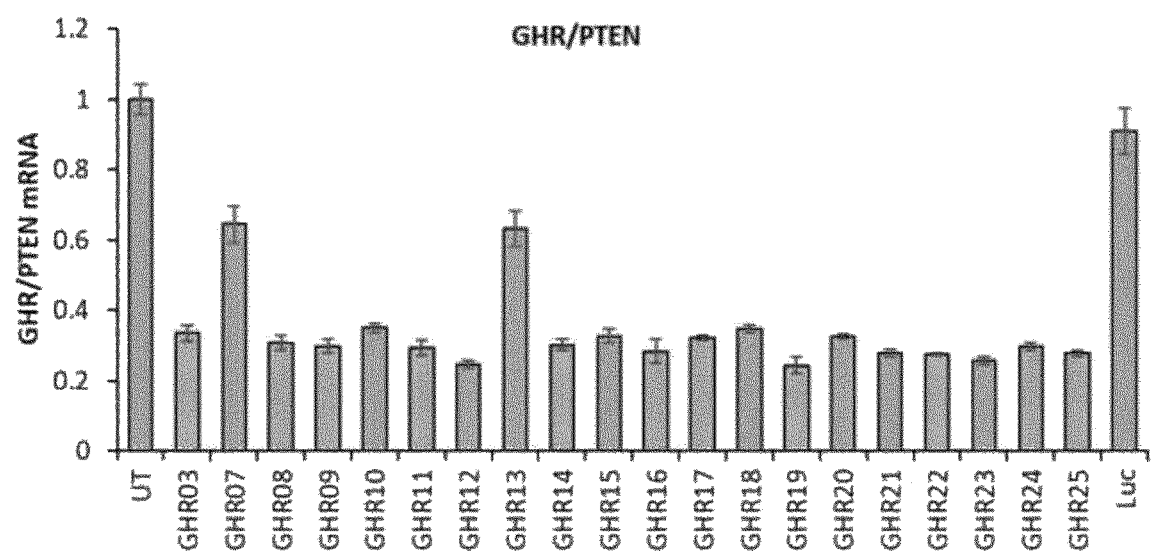

FIGS. 18a and b disclose tolerance for 2'-OMe in an siRNA targeting GHR.

EXAMPLES

Example 1

All Oligonucleotides were either obtained from a commercial oligonucleotide manufacturer (Eurogentec, Belgium) or synthesized on an AKTA oligopilot 10 synthesiser (GE Healthcare) in a 10 µmol scale using phosphoramidite chemistry. Commercially available base loaded CPG solid support (500A, 50 µmol/g), 2'O-Methyl RNA phosphoramidites and 2'Fluoro DNA phosphoramidites (ChemGenes and LinkTech) were used according to the manufacturers recommended procedures. Amidite coupling was performed using 0.1 M solutions of the phosphoramidite in acetonitrile in presence of 0.3 M benzylthiotetrazole (BTT) activator. As ancillary reagents, 0.05 M $I_2$ in pyridine/$H_2O$ (9/1, v/v) as oxidizer, 40% Ac2O in acetonitrile as CapA, 20% N-methylimidazole in acetonitrile as CapB, 3% dichloroacetic acid in toluene as DMT removal and 20% diethylamine in acetonitrile as final wash were used (EMP Biotech). EDITH (LinkTech) was used as thiolation reagent. Acetonitrile (<20 ppm $H_2O$) was purchased from EMP Biotech. All other reagents and solvents were commercially available and used in standard reagent quality.

ST23 is a GalNac C4 phosphoramidite (structure components as below, described in WO2017/174657):

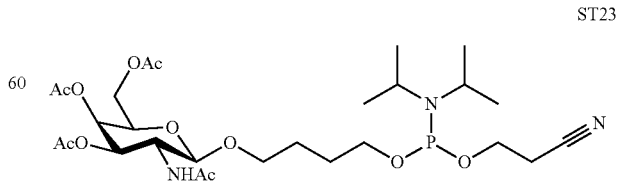

ST23

ST41 is as follows (and as described in WO2017/174657):

ST41

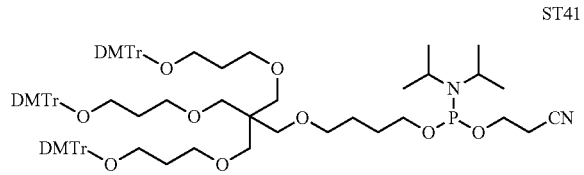

Phosphorothioates were introduced using 50 mM EDITH in acetonitrile. All oligonucleotides were synthesised in DMT-off mode. Diethylamine wash was performed upon completion of the assembly of the oligonucleotide chain on the solid support.

The single strands were cleaved off the CPG and all remaining protective groups were removed by using in 40% aq. methylamine solution (90 min, RT). The crude product was concentrated and purified by Ion exchange chromatography (Resource Q, 6 mL, GE Healthcare) on a AKTA Pure HPLC System (GE Healthcare) using a Sodium chloride gradient (10 mM Tris buffer pH=7.5, 10% acetonitril). Product containing fractions were analysed and pooled and concentrated. Salt removal was achieved by size exclusion chromatography (Zetadex, EMP Biotech). Finally, the individual single strands were lyophilised.

For duplex formation, single strands were reconstituted in 2 mg/mL concentration in water. Equimolar amounts of the respective single strands were added, mixed and heated to 80° C. for 5 min. After cooling the resulting siRNA was analyzed for full double strand formation by native IP-RP HPLC. Product solutions were stored at −20° C. until further use.

The present examples utilise 19mer SiRNAs, unless otherwise apparent from the description and figures.

Example 2

The influence of 2'-OMe at position 14 of the first strand on siRNA activity was tested using a sequence targeting mouse CLIC4. CLC01 is modified with alternating 2'-OMe/2'-OH. CLC15 is modified with 2'-OMe at position 14 of the first strand, whereas CLC16 is not modified with 2'-OMe at this position. All other positions in CLC15 and CLC16 are modified similarly. "UT" indicates an untreated sample the siRNA-treated samples were normalized to. "Luc" was used as non-targeting control.

The experiment was conducted in MS1. Cells were seeded at a density of 40,000 cells per 6-well 24 h before transfection, transfected with 5 nM siRNA and 1 µg/ml Atufect and lysed after 48 h. Total RNA was extracted and CLIC4 and PTEN mRNA levels were determined by Taqman qRT-PCR. Each bar represents mean±SD of three technical replicates.

Data are shown in FIGS. 1a and 1b.

Example 3

The influence of 2'-OMe at position 14 of the first strand on siRNA activity was tested using a sequence targeting mouse CLIC4. CLC01 is modified with alternating 2'-OMe/2'-OH. CLC22 is modified with 2'-OMe at position 4, 9 and 14 of the first strand, whereas CLC28 is modified with 2'-OMe at positions 4, 9 and 15 of the first strand. The second strands of CLC22 and CLC28 are modified similarly. "UT" indicates an untreated sample the siRNA-treated samples were normalized to. "Luc" was used as non-targeting control.

The experiment was conducted in MS1. Cells were seeded at a density of 40,000 cells per 6-well 24 h before transfection, transfected with 5 nM siRNA and 1 µg/ml Atufect and lysed after 48 h. Total RNA was extracted and CLIC4 and Actin mRNA levels were determined by Taqman qRT-PCR. Each bar represents mean±SD of three technical replicates.

Data are shown in FIGS. 2a and 2b.

Example 4

The influence of 2'-OMe at position 2 of the first strand on siRNA activity was tested using a sequence targeting mouse CLIC4. CLC56 is modified with 2'-OMe at position 2 and 4 of the first strand, and 2'-OH at position 3. In contrast, CLC57 has 2'-OH at positions 2 and 4, and 2'-OMe at position 3. All other positions of the first and second strand are modified similarly. "UT" indicates an untreated sample the siRNA-treated samples were normalized to. "Luc" was used as non-targeting control.

The experiment was conducted in MS1. Cells were seeded at a density of 40,000 cells per 6-well 24 h before transfection, transfected with 5 and 1 nM siRNA and 1 µg/ml Atufect and lysed after 48 h. Total RNA was extracted and CLIC4 and PTEN mRNA levels were determined by Taqman qRT-PCR. Each bar represents mean±SD of three technical replicates.

Data are shown in FIGS. 3a and 3b (A).

Example 5

The influence of 2'-OMe at position 2 of the first strand on siRNA activity was tested using a sequence targeting mouse CLIC4. CLC56 is modified with 2'-OMe at position 2 and 4 of the first strand, and 2'-OH at position 3. In contrast, CLC57 has 2'-OH at positions 2 and 4, and 2'-OMe at position 3. All other positions of the first and second strand are modified similarly. "UT" indicates an untreated sample the siRNA-treated samples were normalized to. "Luc" was used as non-targeting control.

The experiment was conducted in MS1. Cells were seeded at a density of 40,000 cells per 6-well 24 h before transfection, transfected with 1 to 0.008 nM siRNA and 1 µg/ml Atufect and lysed after 48 h. Total RNA was extracted and CLIC4 and PTEN mRNA levels were determined by Taqman qRT-PCR. Each bar represents mean±SD of three technical replicates.

Data are shown in FIGS. 3a and 3b (B).

Example 6

The influence of 2'-OMe at position 2 of the first strand on siRNA activity was tested using a sequence targeting mouse CLIC4. CLC01 is modified with alternating 2'-OMe/2'-OH. CLC28 has 2'-OMe at position 4 of the first strand, whereas CLC59 has 2'-OMe at position 2 and CLC60 has 2'-OMe at position 3 of the first strand. All other positions of the first and second strand are modified similarly. "UT" indicates an untreated sample the siRNA-treated samples were normalized to. "Luc" was used as non-targeting control.

The experiment was conducted in MS1. Cells were seeded at a density of 40,000 cells per 6-well 24 h before transfection, transfected with 5 and 1 nM siRNA (A) or 1 to 0.008 nM siRNA (B) and 1 µg/ml Atufect and lysed after 48 h. Total RNA was extracted and CLIC4 and PTEN mRNA levels were determined by Taqman qRT-PCR. Each bar represents mean±SD of three technical replicates.

Data are shown in FIGS. 4a and 4b.

Example 7

The influence of 2'-OMe at position 2 of the first strand on siRNA activity was tested using a sequence targeting human HFE2. In the first strand, HFE04 is modified with 2'-F at position 2 and 2'-OMe at position 3, whereas HFE06 is modified with 2'-OMe at position 2 and 2'-F at position 3. All other positions of the first and second strand are modified similarly. "UT" indicates an untreated sample the siRNA-treated samples were normalized to. "Luc" was used as non-targeting control.

The experiment was conducted in Hep3B. Cells were seeded at a density of 120,000 cells per 6-well 24 h before transfection, transfected with 1 nM siRNA and 1 µg/ml Atufect and lysed after 72 h. Total RNA was extracted and HFE2 and PTEN mRNA levels were determined by Taqman qRT-PCR. Each bar represents mean±SD of three technical replicates.

Data are shown in FIGS. 5a and 5b.

Example 8

Examples 8a and 8b represent biological replicates of the same experiment.

Example 8a

The tolerance for 2'-OMe was investigated by addressing one position at a time in the context of an alternating pattern (change 2'-OMe into 2'-F and vice versa). ALD01 is completely alternating, ALD13-ALD21 contains 2'-F into 2'-Me changes at all even positions of the first strand, ALD22-ALD31 contains 2'-OMe into 2'-F changes at all odd positions of the first strand, ALD32-ALD41 contains 2'-F into 2'-OMe changes at all odd positions of the second strand, ALD42-ALD50 contains 2'-OMe into 2'-F changes at all even positions of the second strand. ALD13 contains 2'-OMe at first strand position 2, ALD19 contains 2'-OMe at first strand position 14, ALD35 contains 2'-OMe at second strand position 7, ALD36 contains 2'-OMe at second strand position 9.

The experiment was conducted in Hep3B. Cells were seeded at a density of 150,000 cells per 6-well 24 h before transfection, transfected with 0.1 nM siRNA and 1 µg/ml Atufect and lysed after 48 h. Total RNA was extracted and ALDH2 and actin mRNA levels were determined by Taqman qRT-PCR. Each bar represents mean±SD of three technical replicates.

Sequences are listed in FIG. 6a and results are shown in FIG. 6b.

Example 8b

The tolerance for 2'-OMe was investigated by addressing one position at a time in the context of an alternating pattern (change 2'-OMe into 2'-F and vice versa). ALD01 is completely alternating, ALD13-ALD21 contains 2'-F into 2'-Me changes at all even positions of the first strand, ALD22-ALD31 contains 2'-OMe into 2'-F changes at all odd positions of the first strand, ALD32-ALD41 contains 2'-F into 2'-OMe changes at all odd positions of the second strand, ALD42-ALD50 contains 2'-OMe into 2'-F changes at all even positions of the second strand. ALD13 contains 2'-OMe at first strand position 2, ALD19 contains 2'-OMe at first strand position 14, ALD35 contains 2'-OMe at second strand position 7, ALD36 contains 2'-OMe at second strand position 9.

The experiment was conducted in Hep3B. Cells were seeded at a density of 150,000 cells per 6-well 24 h before transfection, transfected with 0.1 nM siRNA and 1 µg/ml Atufect and lysed after 48 h. Total RNA was extracted and ALDH2 and actin mRNA levels were determined by Taqman qRT-PCR. Each bar represents mean±SD of three technical replicates.

Figure 6C:
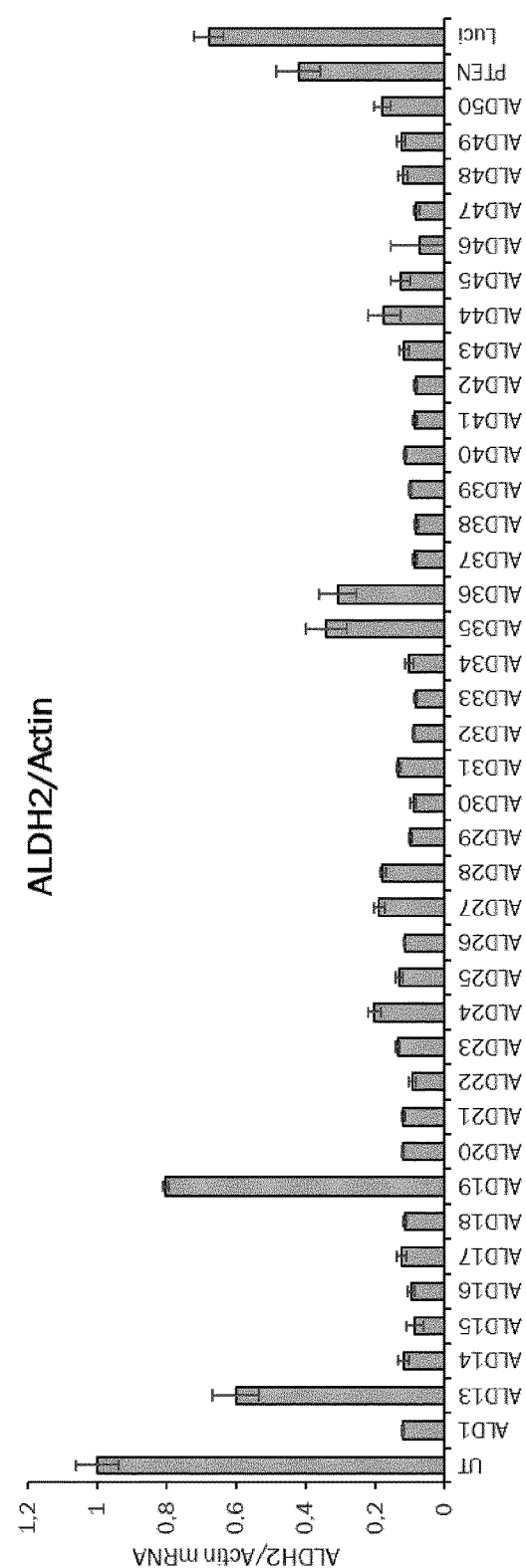

Sequences are listed in FIG. 6a and results are shown in FIG. 6c.

Example 9

Influence of modifications on the activity of two different ALDH2 siRNA sequences Experiment 9-1 Tolerance of positions 2 and 14 for 2'-OMe in the first strand and tolerance of positions 7 and 9 for 2'-OMe in the second strand of an siRNA against ALDH2 was analysed. ALD58 contains alternating 2'-OMe/2'-F in both strands. ALD59-ALD61 contain 2'-F at position 2 and/or 14 of the first strand with an all alternating second strand, whereas ALD62-ALD64 contain 2'-F at position 7 and/or 9 of the second strand with an all alternating first strand. Positions 2 (ALD60) and 14 (ALD59) loose activity upon modification with 2'-OMe, whereas no 2'-OMe at position 2 and 14 restores activity (ALD61). Of the second strand, position 7 (ALD63) and position 9 (ALD62) loose activity upon modification with 2'OMe, whereas no 2'-OMe at positions 7 and 9 restores activity (ALD64).

The experiment was conducted in Hep3B. Cells were seeded at a density of 150,000 cells per 6-well, transfected with 0.1 nM siRNA and 1 µg/ml Atufect after 24 h and lysed after 48 h. Total RNA was extracted and ALDH2 and PTEN mRNA levels were determined by Taqman qRT-PCR. Each bar represents mean±SD from three technical replicates.

Results are shown in FIGS. 7a and b.

Experiment 9-2

Tolerance of positions 2 and 14 for 2'-OMe in the first strand and tolerance of positions 7 and 9 for 2'-OMe in the second strand of a different siRNA against ALDH2 was analyzed. ALD72 contains alternating 2'-OMe/2'-F in both strands. ALD73-ALD75 contain 2'-F at position 2 and/or 14 of the first strand with an all alternating second strand, whereas ALD76-ALD78 contain 2'-F at position 7 and/or 9 of the second strand with an all alternating first strand. Positions 2 (ALD74) and 14 (ALD73) loose activity upon modification with 2'-OMe, whereas no 2'-OMe at position 2 and 14 restores activity (ALD75). Of the second strand, position 7 (ALD77) and position 9 (ALD76) loose activity upon modification with 2'OMe, whereas no 2'-OMe at positions 7 and 9 restores activity (ALD78).

The experiment was conducted in Hep3B. Cells were seeded at a density of 150,000 cells per 6-well, transfected with 0.1 nM siRNA and 1 µg/ml Atufect after 24 h and lysed after 48 h. Total RNA was extracted and ALDH2 and PTEN mRNA levels were determined by Taqman qRT-PCR. Each bar represents mean±SD from three technical replicates.

Results are shown in FIGS. 8a and b.

Example 10

Influence of Modifications on the Activity of an siRNA Targeting DGAT2

Tolerance of positions 2 and 14 for 2'-OMe in the first strand and tolerance of positions 7 and 9 for 2'-OMe in the second strand of an siRNA against DGAT2 was analyzed. DGT01 contains alternating 2'-OMe/2'-F in both strands. DGT02-DGT04 contain 2'-F at position 2 and/or 14 of the first strand with an all alternating second strand, whereas DGT05-DGT07 contain 2'-F at position 7 and/or 9 of the second strand with an all alternating first strand. Positions 2 (DGT03) and 14 (DGT02) loose activity upon modification with 2'-OMe, whereas no 2'-OMe at position 2 and 14 restores activity at least partially (DGT04). Of the second strand, Position 7 (DGT06) and position 9 (DGT05) loose activity upon modification with 2'OMe, whereas no 2'-OMe at positions 7 and 9 restores activity (DGT07).

The experiment was conducted in Huh-7. Cells were seeded at a density of 80,000 cells per 6-well, transfected with 1 nM siRNA and 1 µg/ml Atufect after 24 h and lysed after 48 h. Total RNA was extracted and ALDH2 and PTEN mRNA levels were determined by Taqman qRT-PCR. Each bar represents mean±SD of three technical replicates.

Results are shown in FIGS. 9a and b.

Example 11

Influence of DNA Modifications on siRNA Activity

Tolerance of positions 2 and 14 for DNA modification in the first strand and tolerance of positions 7 and 9 for DNA modification in the second strand of an siRNA against TMPRSS6 was analszed. TMP01 contains alternating 2'-OMe/2'-F in both strands. TMP93 contains 2'-OMe at position 14 of the first strand, whereas TMP113 contains 2'-H at the same position. TMP94 contains 2'-OMe at position 2 of the first strand, whereas TMP112 contains 2'-H at the same position. TMP97 contains 2'-OMe at position 9 of the second strand, whereas TMP117 contains 2'-H at the same position. TMP98 contains 2'-OMe at position 7 of the second strand, whereas TMP116 contains 2'-H at the same position.

The experiment was conducted in Hep3B. Cells were seeded at a density of 150,000 cells per 6-well, transfected with 0.1 nM siRNA and 1 µg/ml Atufect after 24 h and lysed after 48 h. Total RNA was extracted and ALDH2 and Actin mRNA levels were determined by Taqman qRT-PCR. Each bar represents mean±SD from three technical replicates.

Results are shown in FIGS. 10 a and b.

Example 12

Influence of LNA Modifications on siRNA Activity

Tolerance of positions 2 and 14 for LNA modification in the first strand and tolerance of positions 7 and 9 for LNA modification in the second strand of an siRNA against TMPRSS6 was analysed. TMP01 contains alternating 2'-OMe/2'-F in both strands. TMP93 contains 2'-OMe at position 14 of the first strand, whereas TMP111 contains LNA at the same position. TMP94 contains 2'-OMe at position 2 of the first strand, whereas TMP110 contains LNA at the same position. TMP97 contains 2'-OMe at position 9 of the second strand, whereas TMP115 contains LNA at the same position. TMP98 contains 2'-OMe at position 7 of the second strand, whereas TMP114 contains LNA at the same position.

The experiment was conducted in Hep3B. Cells were seeded at a density of 150,000 cells per 6-well, transfected with 0.1 nM siRNA and 1 µg/ml Atufect after 24 h and lysed after 48 h. Total RNA was extracted and ALDH2 and Actin mRNA levels were determined by Taqman qRT-PCR. Each bar represents mean±SD from three technical replicates.

Results are shown in FIGS. 11a and b.

Example 13

Knockdown Activity of Different GalNAc-siRNA Conjugates Targeting TMPRSS6

13A

The influence of 2'-O-methylation at certain second strand strand positions was investigated in the context of GalNAc-siRNA conjugates. All conjugates contain the same first strand. STS12009V23 contains an all-2'-O-methylated second strand, STS12009V25 has one 2'-F modification at second strand position 9, STS12009V26 has one 2'-F modification at second strand position 7, and STS12009V27 has three 2'-F modifications at second strand positions 7-9.

The experiment was conducted in Hep3B. Cells were seeded at a density of 150,000 cells per 6-well, transfected with 5 to 0.005 nM siRNA and 1 µg/ml Atufect after 24 h and lysed after 72 h. Total RNA was extracted and TMPRSS6 and PTEN mRNA levels were determined by Taqman qRT-PCR. Each bar represents mean±SD from three technical replicates.

13B

The influence of 2'-O-methylation at certain second strand positions was investigated in the context of GalNAc-siRNA conjugates. All conjugates contain the same first strand. STS12009V41L4 contains a second strand with alternating 2'-F/2'-OMe, STS12009V23 contains an all-2'-O-methylated second strand, STS12009V25 has one 2'-F modification at second strand position 9, STS12009V26 has one 2'-F modification at second strand position 7, and STS12009V27 has three 2'-F modifications at second strand positions 7-9.

The experiment was conducted in Hep3B. Cells were seeded at a density of 150,000 cells per 6-well, transfected with 10 to 0.001 nM siRNA and 1 µg/ml Atufect after 24 h and lysed after 72 h. Total RNA was extracted and TMPRSS6 and PTEN mRNA levels were determined by Taqman qRT-PCR. Each bar represents mean±SD from three technical replicates.

13C

The influence of 2'-O-methylation at certain second strand positions was investigated in the context of GalNAc-siRNA conjugates. All conjugates contain the same first strand. STS12009V23 contains an all-2'-O-methylated second strand, STS12009V25 has one 2'-F modification at second strand position 9, STS12009V26 has one 2'-F modification at second strand position 7, and STS12009V27 has three 2'-F modifications at second strand positions 7-9.

The experiment was conducted in mouse primary hepatocytes. Cells were seeded at a density of 250,000 cells per 6-well and treated with 100 to 0.25 nM GalNAc-siRNA. Transfections with 10 nM GalNAc-siRNA and 1 µg/ml Atufect served as control.

Cells were lysed after 24 h, total RNA was extracted and TMPRSS6 and Actin mRNA levels were determined by Taqman qRT-PCR. Each bar represents mean±SD from three technical replicates.

Results are shown in FIG. 12a-d.

Example 14

Influence of DNA Modification at Multiple Positions

Tolerance of positions 2 and 14 for DNA in the first strand and tolerance of positions 7-9 for DNA in the second strand of an siRNA against TMPRSS6 was analyzed. TMP70 contains alternating 2'-OMe/2'-F in both strands, whereas TMP119 contains 2'-OMe at all positions except of first strand positions 2 and 14 and second strand positions 7-9. TMP120-TMP126 contain a different number of DNA substitutions at 2'-F positions.

The experiment was conducted in Hep3B. Cells were seeded at a density of 150,000 cells per 6-well, transfected with 1 nM and 0.1 nM siRNA and 1 µg/ml Atufect after 24 h and lysed after 48 h. Total RNA was extracted and TMPRSS6 and PTEN mRNA levels were determined by Taqman qRT-PCR. Each bar represents mean±SD from three technical replicates.

Results are shown in FIGS. 13a and b.

Example 15

Incorporation of DNA at Key Positions.

Tolerance of first strand positions 2 and 14 for DNA and tolerance of second strand positions 7-9 for DNA was analyzed with an siRNA targeting human ALDH2. ALD58 contains alternating 2'-OMe/2'-F in both strands, whereas ALD61 and ALD90-ALD92 contain a reduced 2'-F pattern in the first strand with DNA at position 2 (ALD90), DNA at position 14 (ALD91) and DNA at position 2 and 14 (ALD92), ALD93-ALD96 contain a reduced 2'-F pattern in the second strand with DNA at position 7 (ALD94), DNA at position 9 (ALD95) and DNA at position 7 and 9 (ALD96). ALD97 contains 2'-F at positions 7, 8 and 9 of the second strand, whereas ALD98 contains DNA at these positions.

The experiment was conducted in Hep3B. Cells were seeded at a density of 150,000 cells per 6-well, transfected with 0.1 nM and 0.01 nM siRNA and 1 µg/ml Atufect after 24 h and lysed after 48 h. Total RNA was extracted and ALDH2 and PTEN mRNA levels were determined by Taqman qRT-PCR. Each bar represents mean±SD of three technical replicates.

Data is shown in FIGS. 14a and b.

Example 16

Incorporation of DNA at Key Positions.

Tolerance of first strand positions 2 and 14 for DNA and tolerance of second strand positions 7-9 for DNA was analyzed with a second siRNA targeting human ALDH2. ALD72 contains alternating 2'-OMe/2'-F in both strands, whereas ALD75 and ALD99-ALD101 contain a reduced 2'-F pattern in the first strand with DNA at position 2 (ALD99), DNA at position 14 (ALD100) and DNA at position 2 and 14 (ALD101). ALD102-ALD105 contain a reduced 2'-F pattern in the second strand with DNA at position 7 (ALD103), DNA at position 9 (ALD104) and DNA at position 7 and 9 (ALD105). ALD106 contains 2'-F at positions 7, 8 and 9 of the second strand, whereas ALD107 contains DNA at these positions.

The experiment was conducted in Hep3B. Cells were seeded at a density of 150,000 cells per 6-well, transfected with 0.1 nM and 0.01 nM siRNA and 1 µg/ml Atufect after 24 h and lysed after 48 h. Total RNA was extracted and ALDH2 and PTEN mRNA levels were determined by Taqman qRT-PCR. Each bar represents mean±SD of three technical replicates.

Data is shown in FIGS. 15a and b.

Example 17

Incorporation of DNA at Key Positions.

Tolerance of first strand positions 2 and 14 for DNA and tolerance of second strand positions 7-9 for DNA was analyzed with an siRNA targeting human DGAT2. DGT01 contains alternating 2'-OMe/2'-F in both strands, whereas DGT04 and DGT11-DGT13 contain a reduced 2'-F pattern in the first strand with DNA at position 2 (DGT11), DNA at position 14 (DGT12) and DNA at position 2 and 14 (DGT13). DGT14-DGT17 contain a reduced 2'-F pattern in the second strand with DNA at position 7 (DGT15), DNA at position 9 (DGT16) and DNA at position 7 and 9 (DGT17). DGT18 contains 2'-F at positions 7, 8 and 9 of the second strand, whereas DGT19 contains DNA at these positions.

The experiment was conducted in Huh7. Cells were seeded at a density of 80,000 cells per 6-well, transfected with 10 nM and 1 nM siRNA and 1 µg/ml Atufect after 24 h and lysed after 72 h. Total RNA was extracted and DGAT2 and PTEN mRNA levels were determined by Taqman qRT-PCR. Each bar represents mean±SD of three technical replicates.

Data is shown in FIGS. 16a and b.

Example 18

Incorporation of 2'-O-Methoxyethyl (MOE) at Key Positions.

Tolerance of first strand positions 2 and 14 for 2'-O-MOE and tolerance of second strand positions 7 and 9 for 2'-O-MOE was analyzed with an siRNA targeting ALDH2. ALD108 contains a reduced number of 2'-F in both strands. In this context, 2'-O-MOE is placed at position 2 (ALD115), at position 14 (ALD116) or at both positions 2 and 14 of the first strand (ALD117). Similarly, 2'-O-MOE is placed at position 7 (ALD118), position 9 (ALD119) or at both positions 7 and 9 of the second strand (ALD120). An siRNA against Luciferase was used as non-targeting control ("Luc").

The experiment was conducted in Hep3B. Cells were seeded at a density of 150,000 cells per 6-well, transfected with 0.1 nM siRNA and 1 µg/ml Atufect after 24 h and lysed after 48 h. Total RNA was extracted and ALDH2 and Actin mRNA levels were determined by Taqman qRT-PCR. Each bar represents mean±SD of three technical replicates.

Data is shown in FIGS. 17a and b.

Example 19

Identification of Key Positions in the First Strand.

The tolerance for 2'-OMe was investigated by addressing one position at a time in the context of an alternating pattern (change 2'-OMe into 2'-F and vice versa) in an siRNA targeting GHR. GHR03 contains completely alternating 2'-OMe/2'-F, GHR07-GHR15 contain 2'-F into 2'-OMe changes at all even positions of the first strand, GHR16-GHR25 contain 2'-OMe into 2'-F changes at all odd positions of the first strand. GHR07 contains 2'-OMe at first strand position 2, GHR13 contains 2'-OMe at first strand position 14. An siRNA targeting Luciferase ("Luc") was used as control.

The experiment was conducted in MCF-7 cells. The cells were seeded at a density of 120,000 cells per 6-well 24 h before transfection, transfected with 1 nM siRNA and 1 µg/ml Atufect and lysed after 48 h. Total RNA was extracted and GHR and PTEN mRNA levels were determined by Taqman qRT-PCR. Each bar represents mean±SD of three technical replicates.

Data is shown in FIGS. 18a and b.

| SEQ ID | Name | Sequence (5'-3') |
| --- | --- | --- |
| 1 | CLC28-a | AUGmCAAAAmUACACUmUCUAC |
| 2 | CLC28-b | GmUAGAAGmUGmUAmUmUmUmUGmCAmU |
| 3 | CLC59-a | AmUGCAAAAmUACACUmUCUAC |

-continued

| SEQ ID | Name | Sequence (5'-3') |
|---|---|---|
| 4 | CLC59-b | GmUAGAAGmUGmUAmUmUmUmUGmCAmU |
| 5 | CLC60-a | AUmGCAAAAmUACACUmUCUAC |
| 6 | CLC60-b | GmUAGAAGmUGmUAmUmUmUmUGmCAmU |
| 7 | CLC56-a | AmUGmCAmAAmAUmACmACUUmCUmAC |
| 8 | CLC56-b | mGUmAGmAAmGUGUmAUmUUmUGmCAmU |
| 9 | CLC57-a | AUmGCAmAAmAUmACmACUUmCUmAC |
| 10 | CLC57-b | mGUmAGmAAmGUGUmAUmUUmUGmCAmU |
| 11 | CLC01-a | mAUmGCmAAmAAmUAmCAmCUmUCmUAmC |
| 12 | CLC01-b | GmUAmGAmAGmUGmUAmUUmUUmUGmCmAU |
| 13 | CLC22-a | AUGmCAAAAmUACACmUUCUAC |
| 14 | CLC22-b | GmUAGAAGmUGmUAmUmUmUmUGmCAmU |
| 15 | CLC28-a | AUGmCAAAAmUACACUmUCUAC |
| 16 | CLC28-b | GmUAGAAGmUGmUAmUmUmUmUGmCAmU |
| 17 | CLC16-a | AmUGmCAmAAmAUmACmACUUmCUmAC |
| 18 | CLC16-b | mGUmAGmAAmGUmGUmAUmUUmUGmCAmU |
| 19 | CLC15-a | AmUGmCAmAAmAUmACmACmUUmCUmAC |
| 20 | CLC15-b | mGUmAGmAAmGUmGmUAmUUmUGmCAmU |
| 21 | HFE04-a | fAfUmUfGfAmUfAfGfAfAmCfCfAfUmCfUfUmCfA |
| 22 | HFE04-b | mUfGfAfAfGfAmUfGfGmUmUmCmUfAmUmCfAfAmU |
| 23 | HFE06-a | fAmUfUfGfAmUfAfGfAfAmCfCfAfUmCfUfUmCfA |
| 24 | HFE06-b | mUfGfAfAfGfAmUfGfGmUmUmCmUfAmUmCfAfAmU |
| 25 | ALD01-a | mA(ps)fA(ps)mUfGmUfUmUfUmCfCmUfGmCfUmGfAmC(ps)fG(ps)mG |
| 26 | ALD01-b | fC(ps)mC(ps)fGmUfCmAfGmCfAmGfGmAfAmAfAmCfA(ps)mU(ps)fU |
| 27 | ALD13-a | mA(ps)mA(ps)mUfGmUfUmUfUmCfCmUfGmCfUmGfAmC(ps)fG(ps)mG |
| 28 | ALD13-b | fC(ps)mC(ps)fGmUfCmAfGmCfAmGfGmAfAmAfAmCfA(ps)mU(ps)fU |
| 29 | ALD14-a | mA(ps)fA(ps)mUmGmUfUmUfUmCfCmUfGmCfUmGfAmC(ps)fG(ps)mG |
| 30 | ALD14-b | fC(ps)mC(ps)fGmUfCmAfGmCfAmGfGmAfAmAfAmCfA(ps)mU(ps)fU |
| 31 | ALD15-a | mA(ps)fA(ps)mUfGmUmUmUfUmCfCmUfGmCfUmGfAmC(ps)fG(ps)mG |
| 32 | ALD15-b | fC(ps)mC(ps)fGmUfCmAfGmCfAmGfGmAfAmAfAmCfA(ps)mU(ps)fU |
| 33 | ALD16-a | mA(ps)fA(ps)mUfGmUfUmUmUmCfCmUfGmCfUmGfAmC(ps)fG(ps)mG |
| 34 | ALD16-b | fC(ps)mC(ps)fGmUfCmAfGmCfAmGfGmAfAmAfAmCfA(ps)mU(ps)fU |
| 35 | ALD17-a | mA(ps)fA(ps)mUfGmUfUmUfUmCmCmUfGmCfUmGfAmC(ps)fG(ps)mG |
| 36 | ALD17-b | fC(ps)mC(ps)fGmUfCmAfGmCfAmGfGmAfAmAfAmCfA(ps)mU(ps)fU |
| 37 | ALD18-a | mA(ps)fA(ps)mUfGmUfUmUfUmCfCmUmGmCfUmGfAmC(ps)fG(ps)mG |
| 38 | ALD18-b | fC(ps)mC(ps)fGmUfCmAfGmCfAmGfGmAfAmAfAmCfA(ps)mU(ps)fU |
| 39 | ALD19-a | mA(ps)fA(ps)mUfGmUfUmUfUmCfCmUfGmCmUmGfAmC(ps)fG(ps)mG |
| 40 | ALD19-b | fC(ps)mC(ps)fGmUfCmAfGmCfAmGfGmAfAmAfAmCfA(ps)mU(ps)fU |
| 41 | ALD20-a | mA(ps)fA(ps)mUfGmUfUmUfUmCfCmUfGmCfUmGmAmC(ps)fG(ps)mG |
| 42 | ALD20-b | fC(ps)mC(ps)fGmUfCmAfGmCfAmGfGmAfAmAfAmCfA(ps)mU(ps)fU |

-continued

| SEQ ID | Name | Sequence (5'-3') |
|---|---|---|
| 43 | ALD21-a | mA(ps)fA(ps)mUfGmUfUmUfUmCfCmUfGmCfUmGfAmC(ps)mG(ps)mG |
| 44 | ALD21-b | fC(ps)mC(ps)fGmUfCmAfGmCfAmGfGmAfAmAfAmCfA(ps)mU(ps)fU |
| 45 | ALD22-a | fA(ps)fA(ps)mUfGmUfUmUfUmCfCmUfGmCfUmGfAmC(ps)fG(ps)mG |
| 46 | ALD22-b | fC(ps)mC(ps)fGmUfCmAfGmCfAmGfGmAfAmAfAmCfA(ps)mU(ps)fU |
| 47 | ALD23-a | mA(ps)fA(ps)fUfGmUfUmUfUmCfCmUfGmCfUmGfAmC(ps)fG(ps)mG |
| 48 | ALD23-b | fC(ps)mC(ps)fGmUfCmAfGmCfAmGfGmAfAmAfAmCfA(ps)mU(ps)fU |
| 49 | ALD24-a | mA(ps)fA(ps)mUfGfUfUmUfUmCfCmUfGmCfUmGfAmC(ps)fG(ps)mG |
| 50 | ALD24-b | fC(ps)mC(ps)fGmUfCmAfGmCfAmGfGmAfAmAfAmCfA(ps)mU(ps)fU |
| 51 | ALD25-a | mA(ps)fA(ps)mUfGmUfUfUfUmCfCmUfGmCfUmGfAmC(ps)fG(ps)mG |
| 52 | ALD25-b | fC(ps)mC(ps)fGmUfCmAfGmCfAmGfGmAfAmAfAmCfA(ps)mU(ps)fU |
| 53 | ALD26-a | mA(ps)fA(ps)mUfGmUfUmUfUfCfCmUfGmCfUmGfAmC(ps)fG(ps)mG |
| 54 | ALD26-b | fC(ps)mC(ps)fGmUfCmAfGmCfAmGfGmAfAmAfAmCfA(ps)mU(ps)fU |
| 55 | ALD27-a | mA(ps)fA(ps)mUfGmUfUmUfUmCfCfUfGmCfUmGfAmC(ps)fG(ps)mG |
| 56 | ALD27-b | fC(ps)mC(ps)fGmUfCmAfGmCfAmGfGmAfAmAfAmCfA(ps)mU(ps)fU |
| 57 | ALD28-a | mA(ps)fA(ps)mUfGmUfUmUfUmCfCmUfGfCfUmGfAmC(ps)fG(ps)mG |
| 58 | ALD28-b | fC(ps)mC(ps)fGmUfCmAfGmCfAmGfGmAfAmAfAmCfA(ps)mU(ps)fU |
| 59 | ALD29-a | mA(ps)fA(ps)mUfGmUfUmUfUmCfCmUfGmCfUfGfAmC(ps)fG(ps)mG |
| 60 | ALD29-b | fC(ps)mC(ps)fGmUfCmAfGmCfAmGfGmAfAmAfAmCfA(ps)mU(ps)fU |
| 61 | ALD30-a | mA(ps)fA(ps)mUfGmUfUmUfUmCfCmUfGmCfUmGfAfC(ps)fG(ps)mG |
| 62 | ALD30-b | fC(ps)mC(ps)fGmUfCmAfGmCfAmGfGmAfAmAfAmCfA(ps)mU(ps)fU |
| 63 | ALD31-a | mA(ps)fA(ps)mUfGmUfUmUfUmCfCmUfGmCfUmGfAmC(ps)fG(ps)fG |
| 64 | ALD31-b | fC(ps)mC(ps)fGmUfCmAfGmCfAmGfGmAfAmAfAmCfA(ps)mU(ps)fU |
| 65 | ALD32-a | mA(ps)fA(ps)mUfGmUfUmUfUmCfCmUfGmCfUmGfAmC(ps)fG(ps)mG |
| 66 | ALD32-b | mC(ps)mC(ps)fGmUfCmAfGmCfAmGfGmAfAmAfAmCfA(ps)mU(ps)fU |
| 67 | ALD33-a | mA(ps)fA(ps)mUfGmUfUmUfUmCfCmUfGmCfUmGfAmC(ps)fG(ps)mG |
| 68 | ALD33-b | fC(ps)mC(ps)mGmUfCmAfGmCfAmGfGmAfAmAfAmCfA(ps)mU(ps)fU |
| 69 | ALD34-a | mA(ps)fA(ps)mUfGmUfUmUfUmCfCmUfGmCfUmGfAmC(ps)fG(ps)mG |
| 70 | ALD34-b | fC(ps)mC(ps)fGmUmCmAfGmCfAmGfGmAfAmAfAmCfA(ps)mU(ps)fU |
| 71 | ALD35-a | mA(ps)fA(ps)mUfGmUfUmUfUmCfCmUfGmCfUmGfAmC(ps)fG(ps)mG |
| 72 | ALD35-b | fC(ps)mC(ps)fGmUfCmAmGmCfAmGfGmAfAmAfAmCfA(ps)mU(ps)fU |
| 73 | ALD36-a | mA(ps)fA(ps)mUfGmUfUmUfUmCfCmUfGmCfUmGfAmC(ps)fG(ps)mG |
| 74 | ALD36-b | fC(ps)mC(ps)fGmUfCmAfGmCmAmGfGmAfAmAfAmCfA(ps)mU(ps)fU |
| 75 | ALD37-a | mA(ps)fA(ps)mUfGmUfUmUfUmCfCmUfGmCfUmGfAmC(ps)fG(ps)mG |
| 76 | ALD37-b | fC(ps)mC(ps)fGmUfCmAfGmCfAmGmGmAfAmAfAmCfA(ps)mU(ps)fU |
| 77 | ALD38-a | mA(ps)fA(ps)mUfGmUfUmUfUmCfCmUfGmCfUmGfAmC(ps)fG(ps)mG |
| 78 | ALD38-b | fC(ps)mC(ps)fGmUfCmAfGmCfAmGfGmAmAmAfAmCfA(ps)mU(ps)fU |
| 79 | ALD39-a | mA(ps)fA(ps)mUfGmUfUmUfUmCfCmUfGmCfUmGfAmC(ps)fG(ps)mG |
| 80 | ALD39-b | fC(ps)mC(ps)fGmUfCmAfGmCfAmGfGmAfAmAmAmCfA(ps)mU(ps)fU |

-continued

| SEQ ID | Name | Sequence (5'-3') |
|---|---|---|
| 81 | ALD40-a | mA(ps)fA(ps)mUfGmUfUmUfUmCfCmUfGmCfUmGfAmC(ps)fG(ps)mG |
| 82 | ALD40-b | fC(ps)mC(ps)fGmUfCmAfGmCfAmGfGmAfAmAfAmCmA(ps)mU(ps)fU |
| 83 | ALD41-a | mA(ps)fA(ps)mUfGmUfUmUfUmCfCmUfGmCfUmGfAmC(ps)fG(ps)mG |
| 84 | ALD41-b | fC(ps)mC(ps)fGmUfCmAfGmCfAmGfGmAfAmAfAmCfA(ps)mU(ps)mU |
| 85 | ALD42-a | mA(ps)fA(ps)mUfGmUfUmUfUmCfCmUfGmCfUmGfAmC(ps)fG(ps)mG |
| 86 | ALD42-b | fC(ps)fC(ps)fGmUfCmAfGmCfAmGfGmAfAmAfAmCfA(ps)mU(ps)fU |
| 87 | ALD43-a | mA(ps)fA(ps)mUfGmUfUmUfUmCfCmUfGmCfUmGfAmC(ps)fG(ps)mG |
| 88 | ALD43-b | fC(ps)mC(ps)fGfUfCmAfGmCfAmGfGmAfAmAfAmCfA(ps)mU(ps)fU |
| 89 | ALD44-a | mA(ps)fA(ps)mUfGmUfUmUfUmCfCmUfGmCfUmGfAmC(ps)fG(ps)mG |
| 90 | ALD44-b | fC(ps)mC(ps)fGmUfCfAfGmCfAmGfGmAfAmAfAmCfA(ps)mU(ps)fU |
| 91 | ALD45-a | mA(ps)fA(ps)mUfGmUfUmUfUmCfCmUfGmCfUmGfAmC(ps)fG(ps)mG |
| 92 | ALD45-b | mA(ps)fA(ps)mUfGmUfUmUfUmCfCmUfGmCfUmGfAmC(ps)fG(ps)mG |
| 93 | ALD46-a | mA(ps)fA(ps)mUfGmUfUmUfUmCfCmUfGmCfUmGfAmC(ps)fG(ps)mG |
| 94 | ALD46-b | fC(ps)mC(ps)fGmUfCmAfGmCfAfGfGmAfAmAfAmCfA(ps)mU(ps)fU |
| 95 | ALD47-a | mA(ps)fA(ps)mUfGmUfUmUfUmCfCmUfGmCfUmGfAmC(ps)fG(ps)mG |
| 96 | ALD47-b | fC(ps)mC(ps)fGmUfCmAfGmCfAmGfGfAfAmAfAmCfA(ps)mU(ps)fU |
| 97 | ALD48-a | mA(ps)fA(ps)mUfGmUfUmUfUmCfCmUfGmCfUmGfAmC(ps)fG(ps)mG |
| 98 | ALD48-b | fC(ps)mC(ps)fGmUfCmAfGmCfAmGfGmAfAfAfAmCfA(ps)mU(ps)fU |
| 99 | ALD49-a | mA(ps)fA(ps)mUfGmUfUmUfUmCfCmUfGmCfUmGfAmC(ps)fG(ps)mG |
| 100 | ALD49-b | fC(ps)mC(ps)fGmUfCmAfGmCfAmGfGmAfAmAfAfCfA(ps)mU(ps)fU |
| 101 | ALD50-a | mA(ps)fA(ps)mUfGmUfUmUfUmCfCmUfGmCfUmGfAmC(ps)fG(ps)mG |
| 102 | ALD50-b | fC(ps)mC(ps)fGmUfCmAfGmCfAmGfGmAfAmAfAmCfA(ps)fU(ps)fU |
| 103 | ALD58-a | mAfAmUfGmUfUmUfUmCfCmUfGmCfUmGfAmCfGmG |
| 104 | ALD58-b | fCmCfGmUfCmAfGmCfAmGfGmAfAmAfAmCfAmUfU |
| 105 | ALD59-a | mAfAmUmGmUmUmUmUmCmCmUmGmCmUmGmAmCmGmG |
| 106 | ALD59-b | fCmCfGmUfCmAfGmCfAmGfGmAfAmAfAmCfAmUfU |
| 107 | ALD60-a | mAmAmUmGmUmUmUmUmCmCmUmGmCfUmGmAmCmGmG |
| 108 | ALD60-b | fCmCfGmUfCmAfGmCfAmGfGmAfAmAfAmCfAmUfU |
| 109 | ALD61-a | mAfAmUmGmUmUmUmUmCmCmUmGmCfUmGmAmCmGmG |
| 110 | ALD61-b | fCmCfGmUfCmAfGmCfAmGfGmAfAmAfAmCfAmUfU |
| 111 | ALD62-a | mAfAmUfGmUfUmUfUmCfCmUfGmCfUmGfAmCfGmG |
| 112 | ALD62-b | mCmCmGmUmCmAfGmCmAmGmGmAmAmAmAmCmAmUmU |
| 113 | ALD63-a | mAfAmUfGmUfUmUfUmCfCmUfGmCfUmGfAmCfGmG |
| 114 | ALD63-b | mCmCmGmUmCmAfGmCfAmGmGmAmAmAmAmCmAmUmU |
| 115 | ALD64-a | mAfAmUfGmUfUmUfUmCfCmUfGmCfUmGfAmCfGmG |
| 116 | ALD64-b | mCmCmGmUmCmAfGmCfAmGmGmAmAmAmAmCmAmUmU |
| 117 | ALD72-a | mAfUmGfUmAfGmCfCmGfAmGfGmAfUmCfUmUfCmU |
| 118 | ALD72-b | fAmGfAmAfGmAfUmCfCmUfCmGfGmCfUmAfCmAfU |
| 119 | ALD73-a | mAfUmGmUmAmGmCmCmGmAmGmGmAmUmCmUmUmCmU |

| SEQ ID | Name | Sequence (5'-3') |
|---|---|---|
| 120 | ALD73-b | fAmGfAmAfGmAfUmCfCmUfCmGfGmCfUmAfCmAfU |
| 121 | ALD74-a | mAmUmGmUmAmGmCmCmGmAmGmGmAfUmCmUmUmCmU |
| 122 | ALD74-b | fAmGfAmAfGmAfUmCfCmUfCmGfGmCfUmAfCmAfU |
| 123 | ALD75-a | mAfUmGmUmAmGmCmCmGmAmGmGmAfUmCmUmUmCmU |
| 124 | ALD75-b | fAmGfAmAfGmAfUmCfCmUfCmGfGmCfUmAfCmAfU |
| 125 | ALD76-a | mAfUmGfUmAfGmCfCmGfAmGfGmAfUmCfUmUfCmU |
| 126 | ALD76-b | mAmGmAmAmGmAfUmCmCmUmCmGmGmCmUmAmCmAmU |
| 127 | ALD77-a | mAfUmGfUmAfGmCfCmGfAmGfGmAfUmCfUmUfCmU |
| 128 | ALD77-b | mAmGmAmAmGmAmUmCfCmUmCmGmGmCmUmAmCmAmU |
| 129 | ALD78-a | mAfUmGfUmAfGmCfCmGfAmGfGmAfUmCfUmUfCmU |
| 130 | ALD78-b | mAmGmAmAmGmAfUmCfCmUmCmGmGmCmUmAmCmAmU |
| 131 | DGT01-a | mUfUmAfAmAfUmAfAmCfCmCfAmCfAmGfAmCfAmC |
| 132 | DGT01-b | fGmUfGmUfCmUfGmUfGmGfGmUfUmAfUmUfUmAfA |
| 133 | DGT02-a | mUfUmAmAmAmUmAmAmCmCmCmAmCmAmGmAmCmAmC |
| 134 | DGT02-b | fGmUfGmUfCmUfGmUfGmGfGmUfUmAfUmUfUmAfA |
| 135 | DGT03-a | mUmUmAmAmAmUmAmAmCmCmCmAmCfAmGmAmCmAmC |
| 136 | DGT03-b | fGmUfGmUfCmUfGmUfGmGfGmUfUmAfUmUfUmAfA |
| 137 | DGT04-a | mUfUmAmAmAmUmAmAmCmCmCmAmCfAmGmAmCmAmC |
| 138 | DGT04-b | fGmUfGmUfCmUfGmUfGmGfGmUfUmAfUmUfUmAfA |
| 139 | DGT05-a | mUfUmAfAmAfUmAfAmCfCmCfAmCfAmGfAmCfAmC |
| 140 | DGT05-b | mGmUmGmUmCmUfGmUmGmGmUmUmAmUmUmUmAmA |
| 141 | DGT06-a | mUfUmAfAmAfUmAfAmCfCmCfAmCfAmGfAmCfAmC |
| 142 | DGT06-b | mGmUmGmUmCmUmGmUfGmGmUmUmAmUmUmUmAmA |
| 143 | DGT07-a | mUfUmAfAmAfUmAfAmCfCmCfAmCfAmGfAmCfAmC |
| 144 | DGT07-b | mGmUmGmUmCmUfGmUfGmGmUmUmAmUmUmUmAmA |
| 145 | TMP01-a | mAfAmCfCmAfGmAfAmGfAmAfGmCfAmGfGmUfGmA |
| 146 | TMP01-b | fUmCfAmCfCmUfGmCfUmUfCmUfUmCfUmGfGmUfU |
| 147 | TMP93-a | mAfAmCmCmAmGmAmAmAmGmAmAmGmCmAmGmGmUmGmA |
| 148 | TMP93-b | fUmCfAmCfCmUfGmCfUmUfCmUfUmCfUmGfGmUfU |
| 149 | TMP94-a | mAmAmCmCmAmGmAmAmAmGmAmAmGmCfAmGmGmUmGmA |
| 150 | TMP94-b | fUmCfAmCfCmUfGmCfUmUfCmUfUmCfUmGfGmUfU |
| 151 | TMP97-a | mAfAmCfCmAfGmAfAmGfAmAfGmCfAmGfGmUfGmA |
| 152 | TMP97-b | mUmCmAmCmCmUfGmCmUmUmCmUmUmCmUmGmGmUmU |
| 153 | TMP98-a | mAfAmCfCmAfGmAfAmGfAmAfGmCfAmGfGmUfGmA |
| 154 | TMP98-b | mUmCmAmCmCmUmGmCfUmUmCmUmUmCmUmGmGmUmU |
| 155 | TMP112-a | mA[A]mCmCmAmGmAmAmAmGmAmAmGmCfAmGmGmUmGmA |
| 156 | TMP112-b | fUmCfAmCfCmUfGmCfUmUfCmUfUmCfUmGfGmUfU |
| 157 | TMP113-a | mAfAmCmCmAmGmAmAmAmGmAmAmGmC[A]mGmGmUmGmA |

-continued

| SEQ ID | Name | Sequence (5'-3') |
|---|---|---|
| 158 | TMP113-b | fUmCfAmCfCmUfGmCfUmUfCmUfUmCfUmGfGmUfU |
| 159 | TMP116-a | mAfAmCfCmAfGmAfAmGfAmAfGmCfAmGfGmUfGmA |
| 160 | TMP116-b | mUmCmAmCmCmU[G]mCfUmUmCmUmUmCmUmGmGmUmU |
| 161 | TMP117-a | mAfAmCfCmAfGmAfAmGfAmAfGmCfAmGfGmUfGmA |
| 162 | TMP117-b | mUmCmAmCmCmUfGmC[U]mUmCmUmUmCmUmGmGmUmU |
| 163 | TMP110-a | mA{A}mCmCmAmGmAmAmGmAmAmGmCfAmGmGmUmGmA |
| 164 | TMP110-b | fUmCfAmCfCmUfGmCfUmUfCmUfUmCfUmGfGmUfU |
| 165 | TMP111-a | mAfAmCmCmAmGmAmAmGmAmAmGmC{A}mGmGmUmGmA |
| 166 | TMP111-b | fUmCfAmCfCmUfGmCfUmUfCmUfUmCfUmGfGmUfU |
| 167 | TMP114-a | mAfAmCfCmAfGmAfAmGfAmAfGmCfAmGfGmUfGmA |
| 168 | TMP114-b | mUmCmAmCmCmU{G}mCfUmUmCmUmUmCmUmGmGmUmU |
| 169 | TMP115-a | mAfAmCfCmAfGmAfAmGfAmAfGmCfAmGfGmUfGmA |
| 170 | TMP115-a | mUmCmAmCmCmUfGmC{U}mUmCmUmUmCmUmGmGmUmU |
| 171 | STS12009V23L4-a | mA(ps)fA(ps)mCmCmAmGmAmAmGmAmAfGmCfAmGmGmU(ps)mG(ps)mA |
| 172 | STS12009V23L4-b | GalNAc-mUmCmAmCmCmUmGmCmUmUmCmUmUmCmUmGmG(ps)mU(ps)mU |
| 173 | STS12009V25L4-a | mA(ps)fA(ps)mCmCmAmGmAmAmGmAmAfGmCfAmGmGmU(ps)mG(ps)mA |
| 174 | STS12009V25L4-b | GalNAc-mUmCmAmCmCmUmGmCfUmUmCmUmUmCmUmGmG(ps)mU(ps)mU |
| 175 | STS12009V26L4-a | mA(ps)fA(ps)mCmCmAmGmAmAmGmAmAfGmCfAmGmGmU(ps)mG(ps)mA |
| 176 | STS12009V26L4-b | GalNAc-mUmCmAmCmCmUfGmCmUmUmCmUmUmCmUmGmG(ps)mU(ps)mU |
| 177 | STS12009V27L4-a | mA(ps)fA(ps)mCmCmAmGmAmAmGmAmAfGmCfAmGmGmU(ps)mG(ps)mA |
| 178 | STS12009V27L4-b | GalNAc-mUmCmAmCmCmUfGfCfUmUmCmUmUmCmUmGmG(ps)mU(ps)mU |
| 179 | STS12009V41L4-a | mA(ps)fA(ps)mCmCmAmGmAmAmGmAmAfGmCfAmGmGmU(ps)mG(ps)mA |
| 180 | STS12009V41L4-b | GalNAc-fUmCfAmCfCmUfGmCfUmUfCmUfUmCfUmGfG(ps)mU(ps)fU |
| 181 | TMP70-a | mA(ps)fA(ps)mCfCmAfGmAfAmGfAmAfGmCfAmGfGmU(ps)fG(ps)mA |
| 182 | TMP70-b | fU(ps)mC(ps)fAmCfCmUfGmCfUmUfCmUfUmCfUmGfG(ps)mU(ps)fU |
| 183 | TMP119-A | mA(ps)fA(ps)mCfCmAfGmAfAmGfAmAfGmCfAmGfGmU(ps)fG(ps)mA |
| 184 | TMP119-B | mU(ps)mC(ps)mAmCmCmUfGfCfUmUmCmUmUmCmUmGmG(ps)mU(ps)mU |
| 185 | TMP120-A | mA(ps)fA(ps)mCmCmAmGmAmAmGmAmAmGmCfAmGmGmU(ps)mG(ps)mA |
| 186 | TMP120-B | mU(ps)mC(ps)mAmCmCmUfGfCfUmUmCmUmUmCmUmGmG(ps)mU(ps)mU |
| 187 | TMP121-A | mA(ps)fA(ps)mCfCmAfGmAfAmGfAmAfGmCfAmGfGmU(ps)fG(ps)mA |
| 188 | TMP121-B | mU(ps)mC(ps)mAmCmCmU[G][C][T]mUmCmUmUmCmUmGmG(ps)mU(ps)mU |
| 189 | TMP122-A | mA(ps)fA(ps)mCfCmAfGmAfAmGfAmAfGmCfAmGfGmU(ps)fG(ps)mA |
| 190 | TMP122-B | mU(ps)mC(ps)mAmCmCmU[G]mC[T]mUmCmUmUmCmUmGmG(ps)mU(ps)mU |
| 191 | TMP123-A | mA(ps)fA(ps)mCmCmAmGmAmAmGmAmAmGmCfAmGmGmU(ps)mG(ps)mA |
| 192 | TMP123-B | mU(ps)mC(ps)mAmCmCmU[G][C][T]mUmCmUmUmCmUmGmG(ps)mU(ps)mU |
| 193 | TMP124-A | mA(ps)[A](ps)mCmCmAmGmAmAmGmAmAmGmC[A]mGmGmU(ps)mG(ps)mA |
| 194 | TMP124-B | mU(ps)mC(ps)mAmCmCmU[G][C][T]mUmCmUmUmCmUmGmG(ps)mU(ps)mU |
| 195 | TMP125-A | mA(ps)[A](ps)mCmCmAmGmAmAmGmAmAmGmCfAmGmGmU(ps)mG(ps)mA |
| 196 | TMP125-B | mU(ps)mC(ps)mAmCmCmU[G][C][T]mUmCmUmUmCmUmGmG(ps)mU(ps)mU |

-continued

| SEQ ID | Name | Sequence (5'-3') |
|---|---|---|
| 197 | TMP126-A | mA(ps)[A](ps)mCmCmAmGmAmAmGmAmAmGmCAmGmGmU(ps)mG(ps)mA |
| 198 | TMP126-B | mU(ps)mC(ps)mAmCmCmU[G][C][T]mUmCmUmUmCmUmGmG(ps)mU(ps)mU |
| 199 | ALD91-A | mAfAmUmGmUmUmUmUmCmCmUmGmC[T]mGmAmCmGmG |
| 200 | ALD91-B | fCmCfGmUfCmAfGmCfAmGfGmAfAmAfAmCfAmUfU |
| 201 | ALD92-A | mA[A]mUmGmUmUmUmUmCmCmUmGmC[T]mGmAmCmGmG |
| 202 | ALD92-B | fCmCfGmUfCmAfGmCfAmGfGmAfAmAfAmCfAmUfU |
| 203 | ALD93-A | mAfAmUfGmUfUmUfUmCfCmUfGmCfUmGfAmCfGmG |
| 204 | ALD93-B | mCmCmGmUmCmAfGmCfAmGmGmAmAmAmAmCmAmUmU |
| 205 | ALD94-A | mAfAmUfGmUfUmUfUmCfCmUfGmCfUmGfAmCfGmG |
| 206 | ALD94-B | mCmCmGmUmCmA[G]mCfAmGmGmAmAmAmAmCmAmUmU |
| 207 | ALD95-A | mAfAmUfGmUfUmUfUmCfCmUfGmCfUmGfAmCfGmG |
| 208 | ALD95-B | mCmCmGmUmCmAfGmC[A]mGmGmAmAmAmAmCmAmUmU |
| 209 | ALD96-A | mAfAmUfGmUfUmUfUmCfCmUfGmCfUmGfAmCfGmG |
| 210 | ALD96-B | mCmCmGmUmCmA[G]mC[A]mGmGmAmAmAmAmCmAmUmU |
| 211 | ALD97-A | mAfAmUfGmUfUmUfUmCfCmUfGmCfUmGfAmCfGmG |
| 212 | ALD97-B | mCmCmGmUmCmAfGfCfAmmGmAmAmAmAmCmAmUmU |
| 213 | ALD98-A | mAfAmUfGmUfUmUfUmCfCmUfGmCfUmGfAmCfGmG |
| 214 | ALD98-B | mCmCmGmUmCmA[G][C][A]mGmGmAmAmAmAmCmAmUmU |
| 215 | ALD99-A | mAfUmGfUmAfGmCfCmGfAmGfGmAfUmCfUmUfCmU |
| 216 | ALD99-B | fAmGfAmAfGmAfUmCfCmUfCmGfGmCfUmAfCmAfU |
| 217 | ALD100-A | mAfUmGmUmAmGmCmCmGmAmGmA[T]mCmUmUmCmU |
| 218 | ALD100-B | fAmGfAmAfGmAfUmCfCmUfCmGfGmCfUmAfCmAfU |
| 219 | ALD101-A | mA[T]mGmUmAmGmCmCmGmAmGmA[T]mCmUmUmCmU |
| 220 | ALD101-B | fAmGfAmAfGmAfUmCfCmUfCmGfGmCfUmAfCmAfU |
| 221 | ALD102-A | mAfUmGfUmAfGmCfCmGfAmGfGmAfUmCfUmUfCmU |
| 222 | ALD102-B | mAmGmAmAmGmAfUmCfCmUmCmGmGmCmUmAmCmAmU |
| 223 | ALD103-A | mAfUmGfUmAfGmCfCmGfAmGfGmAfUmCfUmUfCmU |
| 224 | ALD103-B | mAmGmAmAmGmA[T]mCfCmUmCmGmGmCmUmAmCmAmU |
| 225 | ALD104-A | mAfUmGfUmAfGmCfCmGfAmGfGmAfUmCfUmUfCmU |
| 226 | ALD104-B | mAmGmAmAmGmAmUmC[C]mUmCmGmGmCmUmAmCmAmU |
| 227 | ALD105-A | mAfUmGfUmAfGmCfCmGfAmGfGmAfUmCfUmUfCmU |
| 228 | ALD105-B | mAmGmAmAmGmA[U]mC[C]mUmCmGmGmCmUmAmCmAmU |
| 229 | ALD106-A | mAfUmGfUmAfGmCfCmGfAmGfGmAfUmCfUmUfCmU |
| 230 | ALD106-B | mAmGmAmAmGmAfUfCfCmUmCmGmGmCmUmAmCmAmU |
| 231 | ALD107-A | mAfUmGfUmAfGmCfCmGfAmGfGmAfUmCfUmUfCmU |
| 232 | ALD107-B | mAmGmAmAmGmA[T][C][C]mUmCmGmGmCmUmmAmCmAmU |
| 233 | DGT11-A | mU[T]mAmAmAmUmAmAmmCmCmCmAmCfAmGmAmCmAmC |
| 234 | DGT11-B | fGmUfGmUfCmUfGmUfGmGfGmUfUmAfUmUfUmAfA |

-continued

| SEQ ID | Name | Sequence (5'-3') |
|---|---|---|
| 235 | DGT12-A | mUfUmAmAmAmUmAmAmCmCmAmC[A]mGmAmCmAmC |
| 236 | DGT12-B | fGmUfGmUfCmUfGmUfGmGfGmUfUmAfUmUfUmAfA |
| 237 | DGT13-A | mUfUmAmAmAmUmAmAmCmCmAmC[A]mGmAmCmAmC |
| 238 | DGT13-B | fGmUfGmUfCmUfGmUfGmGfGmUfUmAfUmUfUmAfA |
| 239 | DGT14-A | mU[T]mAmAmAmUmAmAmCmCmAmC[A]mGmAmCmAmC |
| 240 | DGT14-B | fGmUfGmUfCmUfGmUfGmGfGmUfUmAfUmUfUmAfA |
| 241 | DGT15-A | mUfUmAfAmAfUmAfAmCfCmCfAmCfAmGfAmCfAmC |
| 242 | DGT15-B | mGmUmGmUmCmUfGmUfGmGmUmAmUmUmUmAmA |
| 243 | DGT16-A | mUfUmAfAmAfUmAfAmCfCmCfAmCfAmGfAmCfAmC |
| 244 | DGT16-B | mGmUmGmUmCmUfGmU[G]mGmGmUmAmUmUmUmAmA |
| 245 | DGT17-A | mUfUmAfAmAfUmAfAmCfCmCfAmCfAmGfAmCfAmC |
| 246 | DGT17-B | mGmUmGmUmCmU[G]mU[G]mGmGmUmAmUmUmUmAmA |
| 247 | DGT18-A | mUfUmAfAmAfUmAfAmCfCmCfAmCfAmGfAmCfAmC |
| 248 | DGT18-B | mGmUmGmUmCmUfGfUfGmGmUmAmUmUmUmAmA |
| 249 | DGT19-A | mUfUmAfAmAfUmAfAmCfCmCfAmCfAmGfAmCfAmC |
| 250 | DGT19-B | mGmUmGmUmCmU[G][T][G]mGmGmUmAmUmUmUmAmA |
| 251 | ALD108-A | mA(ps)fU(ps)mGmUmAmGmCmCmGmAmGmGmAfUmCmUmU(ps)mC(ps)mU |
| 252 | ALD108-B | mA(ps)mG(ps)mAmAmGmAfUmCfCmUmCmGmGmCmUmAmC(ps)mA(ps)mU |
| 253 | ALD115-A | mA(ps)(MOE-U)(ps)mGmUmAmGmCmCmGmAmGmGmAfUmCmUmU(ps)mC(ps)mU |
| 254 | ALD115-B | mA(ps)mG(ps)mAmAmGmAfUmCfCmUmCmGmGmCmUmAmC(ps)mA(ps)mU |
| 255 | ALD116-A | mA(ps)fU(ps)mGmUmAmGmCmCmGmAmGmGmA(MOE-U)mCmUmU(ps)mC(ps)mU |
| 256 | ALD116-B | mA(ps)mG(ps)mAmAmGmAfUmCfCmUmCmGmGmCmUmAmC(ps)mA(ps)mU |
| 257 | ALD117-A | mA(ps)(MOE-U)(ps)mGmUmAmGmCmCmGmAmGmGmA(MOE-U)mCmUmU(ps)mC(ps)mU |
| 258 | ALD117-B | mA(ps)mG(ps)mAmAmGmAfUmCfCmUmCmGmGmCmUmAmC(ps)mA(ps)mU |
| 259 | ALD118-A | mA(ps)fU(ps)mGmUmAmGmCmCmGmAmGmGmAfUmCmUmU(ps)mC(ps)mU |
| 260 | ALD118-B | mA(ps)mG(ps)mAmAmGmA(MOE-U)mCfCmUmCmGmGmCmUmAmC(ps)mA(ps)mU |
| 261 | ALD119-A | mA(ps)fU(ps)mGmUmAmGmCmCmGmAmGmGmAfUmCmUmU(ps)mC(ps)mU |
| 262 | ALD119-B | mA(ps)mG(ps)mAmAmGmAfUmC(MOE-C)mUmCmGmGmCmUmAmC(ps)mA(ps)mU |
| 263 | ALD120-A | mA(ps)fU(ps)mGmUmAmGmCmCmGmAmGmGmAfUmCmUmU(ps)mC(ps)mU |
| 264 | ALD120-B | mA(ps)mG(ps)mAmAmGmA(MOE-U)mC(MOE-C)mUmCmGmGmCmUmAmC(ps)mA(ps)mU |
| 265 | CLC28-a | AUGCAAAAUACACUUCUAC |
| 266 | CLC28-b | GUAGAAGUGUAUUUUGCAU |
| 267 | HFE04-a | AUUGAUAGAACCAUCUUCA |
| 268 | HFE04-b | UGAAGAUGGUUCUAUCAAU |
| 269 | ALD01-a | AAUGUUUUCCUGCUGACGG |
| 270 | ALD01-b | CCGUCAGCAGGAAAACAUU |
| 271 | ALD72-a | AUGUAGCCGAGGAUCUUCU |
| 272 | ALD72-b | AGAAGAUCCUCGGCUACAU |

-continued

| SEQ ID | Name | Sequence (5'-3') |
|---|---|---|
| 273 | DGT01-a | UUAAAUAACCCACAGACAC |
| 274 | DGT01-b | GUGUCUGUGGGUUAUUUAA |
| 275 | TMP01-a | AACCAGAAGAAGCAGGUGA |
| 276 | TMP01-b | UCACCUGCUUCUUCUGGUU |
| 277 | STS12009V23L4-a | AACCAGAAGAAGCAGGUGA |
| 278 | STS12009V23L4-b | UCACCUGCUUCUUCUGGUU |

Key
A, U, C, G-RNA
mA, mU, mC, mG-2'-OMe RNA
fA, fU, fC, fG-2'-F RNA
(ps)-phosphorothioate
[A], [U], [C], [G]-2'-H (DNA)
{A}, {U}, {C}, {G}-LNA
GalNAc-[ST23 (ps)]3 ST41 (ps)
(MOE-U), (MOE-C)-2'methoxyethyl RNA The sequences listed above may be disclosed with a linker or ligand, such as GalNAC or (ps) or (ps2) linkages for example. These form an optional, but preferred, part of the sequence of the sequence listing.

The following abbreviations may be used:

| | |
|---|---|
| ivN | Inverted nucleotide, either 3'-3' or 5'-5' |
| (ps2) | Phosphorodithioate |
| vinylphosphonate | Vinyl-(E)-phosphonate |
| FAM | 6-Carboxyfluorescein |
| TAMRA | 5-Carboxytetramethylrhodamine |
| BHQ1 | Black Hole Quencher 1 |
| (ps) | Phosphorothioate |
| GN | |

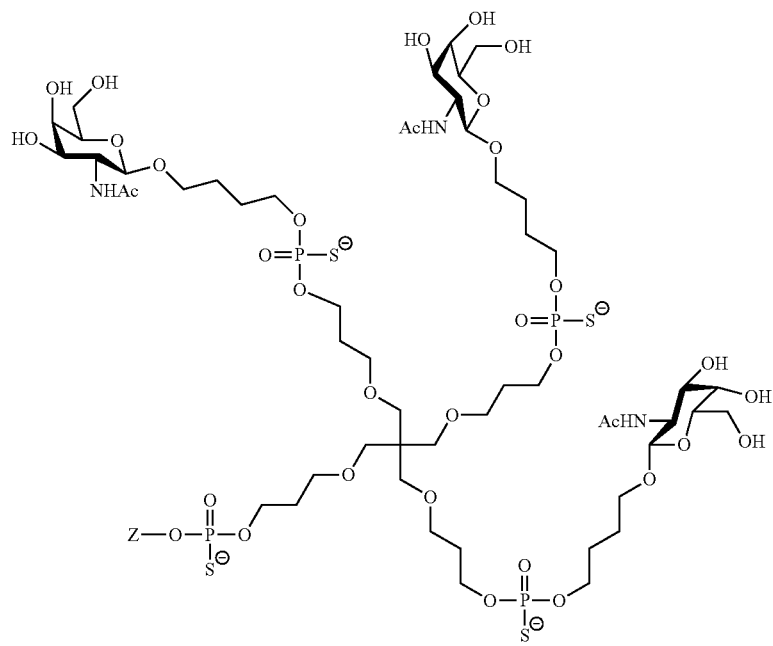

GN2
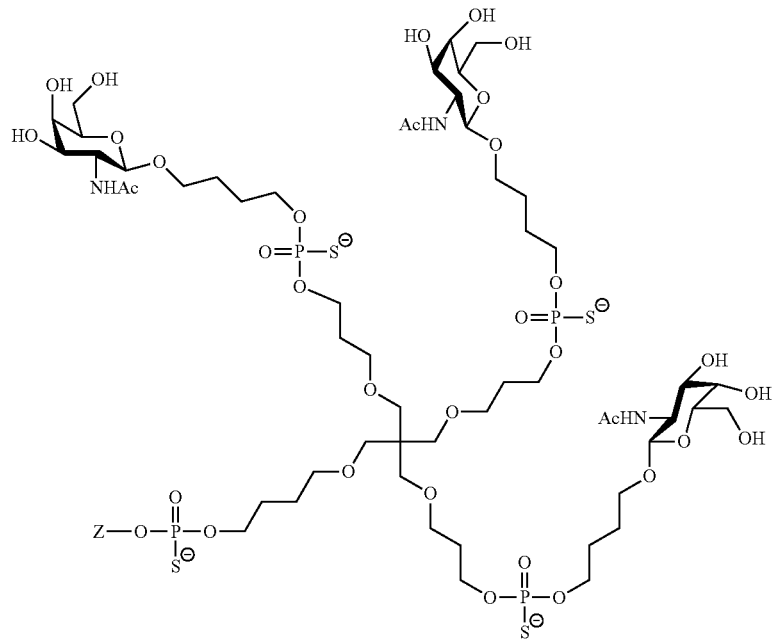
GN3
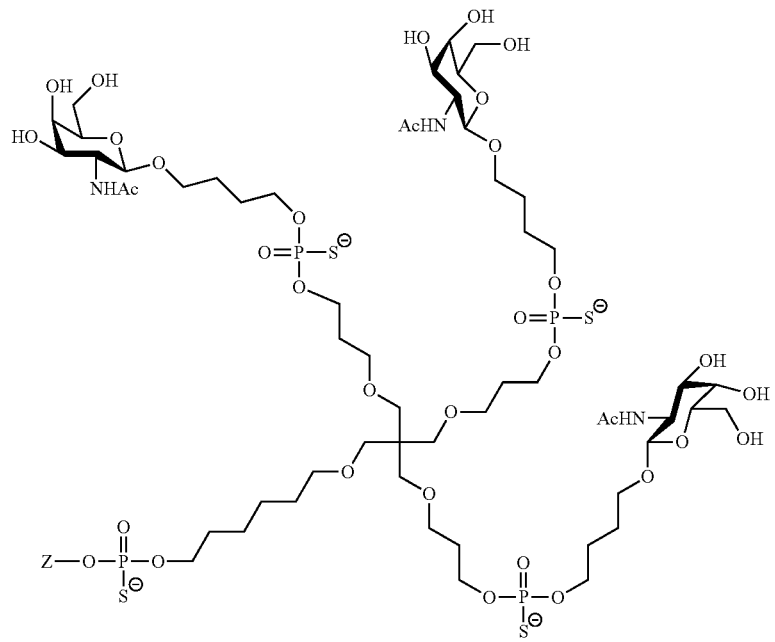
GNo    Same as GN2 but with phosphodiesters instead of phosphorothioates
ST23
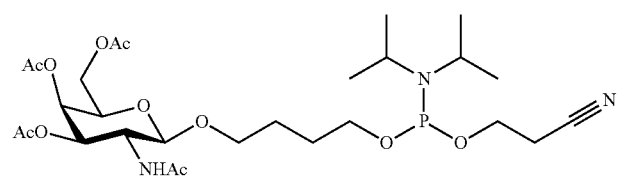

-continued
| | |
|---|---|
| ST41/C4XLT | 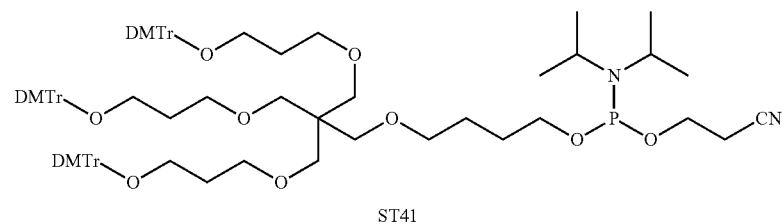 ST41 |
| ST43/C6XLT | 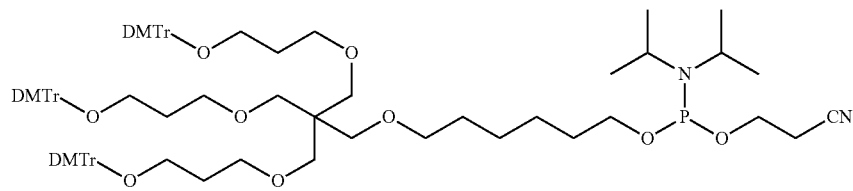 |
| Long trebler/ltrb/STKS | 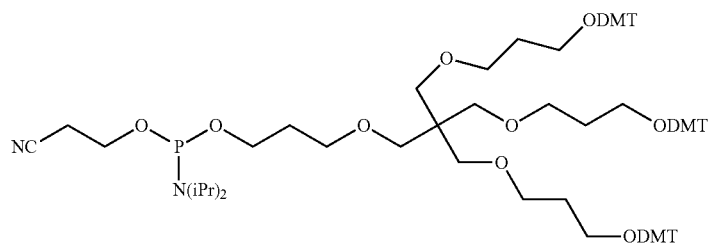 |
| Ser(GN) | 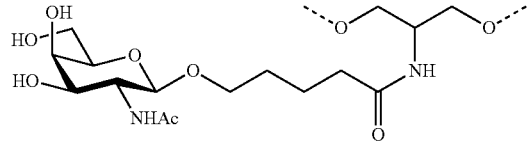 |
| GlyC3Am(GalNAc) | 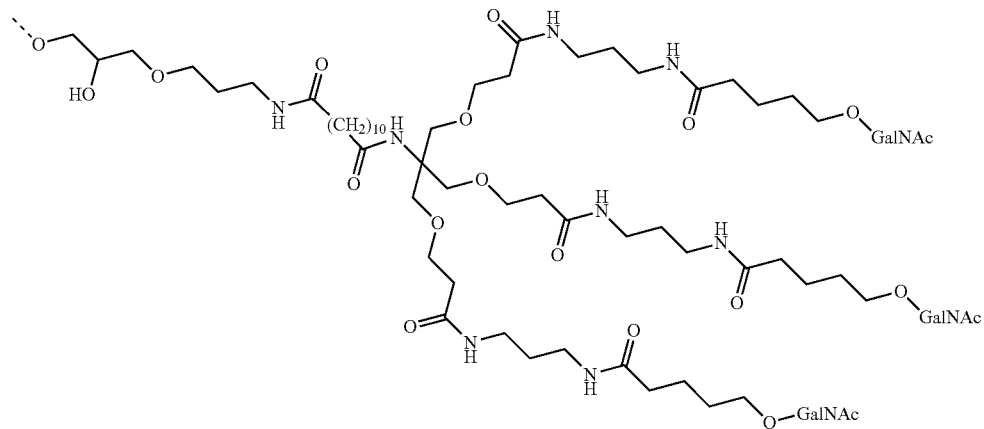 |
| GalNAc (only in when used in sequences) | GN2 (see above) |
| (MOE-U), (MOE-C) | 2'methoxyethyl RNA |
| {A}, {U}, {C}, {G} | LNA |
| [ST23 (ps)]3 ST41 (ps) | GN2 (see above) |
| [ST23 (ps)]3 ST43 (ps) | GN3 (see above) |
| ST23(ps) long trebler(ps) | GN (see above) |

STATEMENTS OF INVENTION

1. Nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene, wherein said first strand includes modified nucleotides or unmodified nucleotides at a plurality of positions in order to facilitate processing of the nucleic acid by RISC.

2. Nucleic acid of statement 1, wherein the nucleotides at positions 2 and 14 from the 5' end of the first strand are modified.

3. Nucleic acid of statement 1 or statement 2, wherein the nucleotides at positions 2 and 14 from the 5' end of the first strand are not modified with a 2' O-methyl modification.

4. Nucleic acid of any one of statements 1 to 3, wherein the nucleotides at positions 2 and 14 from the 5' end of the first strand are not modified with a modification selected from the group consisting of 2'-O-(2-Methoxyethyl), 2'-O-allyl, 2'-O-DNP, 2'-CE, 2'-EA, 2'-AEM, 2'-APM and 2'-GE.

5. Nucleic acid of any one of statements 1 to 3, wherein the nucleotides at positions 2 and 14 from the 5' end of the first strand are modified with a modification selected from the group consisting of 2'F, 4'-S, 2'-FANA and UNA.

6. Nucleic acid of statement 1, wherein the nucleotides at positions 2 and 14 from the 5' end of the first strand are unmodified.

7. Nucleic acid of any one of statements 1 to 6, wherein in the second strand, nucleotides at position 2 and 14 from the 5' end of the second strand are modified with a 2' O-methyl modification or with a '-O-(2-Methoxyethyl) modification.

8. Nucleic acid of any one of statements 1 to 7, wherein the first strand and the second strand are separate strands 9. Nucleic acid of any one of statements 1 to 7, comprising a single strand that comprises the first strand and the second strand.

10. Nucleic acid according to any one of statements 1 to 9, wherein said first strand and/or said second strand are each from 17-35 nucleotides in length 11. Nucleic acid of any one of statements 1 to 10, wherein the at least one duplex region consists of 19-25 nucleotide base pairs.

12. Nucleic acid of any preceding statement, which
a) is blunt ended at both ends; or
b) has an overhang at one end and a blunt end at the other; or
c) has an overhang at both ends.

13. Nucleic acid according to any preceding statement, wherein one or more nucleotides on the first and/or second strand are modified, to form modified nucleotides.

14. Nucleic acid of statement 13, wherein one or more of the odd numbered nucleotides of the first strand are modified.

15. Nucleic acid according to statement 14, wherein one or more of the even numbered nucleotides of the first strand are modified by at least a second modification, wherein the at least second modification is different from the modification of statement 14.

16. Nucleic acid of statement 15, wherein at least one of the one or more modified even numbered nucleotides is adjacent to at least one of the one or more modified odd numbered nucleotides.

17. Nucleic acid of any of statements 14 to 16, wherein a plurality of odd numbered nucleotides are modified.

18. Nucleic acid of statement 15 or 17, wherein a plurality of even numbered nucleotides are modified by a second modification.

19. Nucleic acid of any of statements 13 to 18, wherein the first strand comprises adjacent nucleotides that are modified by a common modification.

20. Nucleic acid of any of statements 14 to 19, wherein the first strand comprises adjacent nucleotides that are modified by a second modification that is different to the modification of statement 14.

21. Nucleic acid of any of statements 14 to 20, wherein one or more of the odd numbered nucleotides of the second strand are modified by a modification that is different to the modification of statement 14.

22. Nucleic acid according to any of statements 14 to 21, wherein one or more of the even numbered nucleotides of the second strand are modified by the modification of statement 14.

23. Nucleic acid of statement 21 or 22, wherein at least one of the one or more modified even numbered nucleotides of the second strand is adjacent to the one or more modified odd numbered nucleotides.

24. Nucleic acid of any of statements 21 to 23, wherein a plurality of odd numbered nucleotides of the second strand are modified by a common modification.

25. Nucleic acid of any of statements 21 to 24, wherein a plurality of even numbered nucleotides are modified by a modification according to statement 14.

26. Nucleic acid of any of statements 21 to 25, wherein a plurality of odd numbered nucleotides are modified by a second modification, wherein the second modification is different from the modification of statement 14.

27. Nucleic acid of any of statements 21 to 26, wherein the second strand comprises adjacent nucleotides that are modified by a common modification.

28. Nucleic acid of any of statements 21 to 27, wherein the second strand comprises adjacent nucleotides that are modified by a second modification that is different from the modification of statement 14.

29. Nucleic acid of statements 13 to 28, wherein each of the odd numbered nucleotides in the first strand and each of the even numbered nucleotides in the second strand are modified with a common modification.

30. Nucleic acid of statement 29, wherein each of the even numbered nucleotides are modified in the first strand with a second modification and each of the odd numbered nucleotides are modified in the second strand with a second modification, provided that positions 2 and 14 are not modified with a 2'OMe.

31. Nucleic acid according to any of statements 13 to 30, wherein the modified nucleotides of the first strand are shifted by at least one nucleotide relative to the unmodified or differently modified nucleotides of the second strand.

32. Nucleic acid according to any one of statements 13 to 31, wherein the first modification and the second modification are each and individually selected from the group consisting of 3'-terminal deoxy-thymine, 2'-O-methyl, 2'-deoxy-modification, a locked nucleotide, an abasic nucleotide, a 2'-amino-modification, a 2'-alkyl-modification, a morpholino modification, a phosphoramidate modification, a non-natural base comprising nucleotide, 5'-phosphorothioate group modification, a 5' phosphate or 5' phosphate mimic modification and a cholesteryl derivative or a dodecanoic acid bisdecylamide group modification.

33. Nucleic acid of any preceding statement wherein the modification nucleotide is any one of a locked nucleotide, an abasic nucleotide or a non-natural base comprising nucleotide.

34. Nucleic acid according to any one of statements 13 to 33, wherein the first modification is 2'-O-methyl.

35. Nucleic acid of any one of statements 13 to 34, wherein the second modification is 2'-F.

36. Nucleic acid according to any one of statements 1 to 35, conjugated with a ligand.

37. Nucleic acid according to any one of statements 1 to 36, wherein the linkage between the terminal one, two or three 3' and/or 5' nucleotides on the first and/or the second strand of the Nucleic acid comprises a phosphorothioate linkage.

38. Nucleic acid according to any one of statements 1 to 37, wherein both the 5' and 3' terminal ends of the first strand and the 3' end of the second strand comprise two phosphorothioate linkages.

39. Nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene, wherein said first strand includes modified nucleotides or modified nucleotides at a plurality of positions in order to facilitate processing of the nucleic acid by RISC, and wherein the nucleic acid is conjugated to a ligand.

40. Nucleic acid according to any of statements 36 to 39, wherein the ligand comprises one or more GalNac ligands or derivatives thereof.

41. Nucleic acid according to any of statements 36 to 40, wherein the ligand is conjugated to nucleic acid as defined in any preceding statements by a bivalent or trivalent branched linker.

42. Nucleic acid of statement 39 to 41, wherein the nucleotides are modified as defined in any preceding statements.

43. A nucleic acid of any of statements 36 to 42, wherein the ligand comprises the formula I:

$$[S—X^1—P—X^2]_3\text{-A-}X^3— \qquad (I)$$

wherein:
S represents a saccharide, wherein the saccharide is N-acetyl galactosamine;
$X^1$ represents $C_3$-$C_6$ alkylene or (—$CH_2$—$CH_2$—O)m(—$CH_2$)$_2$— wherein m is 1, 2, or 3;
P is a phosphate or modified phosphate (preferably a thiophosphate);
$X^2$ is alkylene or an alkylene ether of the formula (—$CH_2$)$_n$—O—$CH_2$— where n=1-6;
A is a branching unit;
$X^3$ represents a bridging unit;
wherein a nucleic acid according to the present invention is conjugated to $X^3$ via a phosphate or modified phosphate (preferably a thiophosphate).

44. A conjugated nucleic acid having one of the following structures

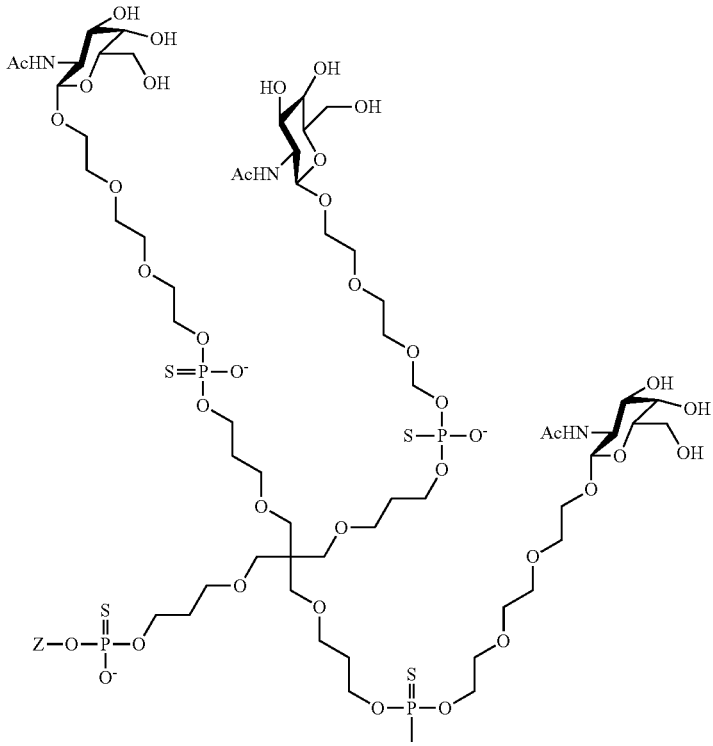

-continued
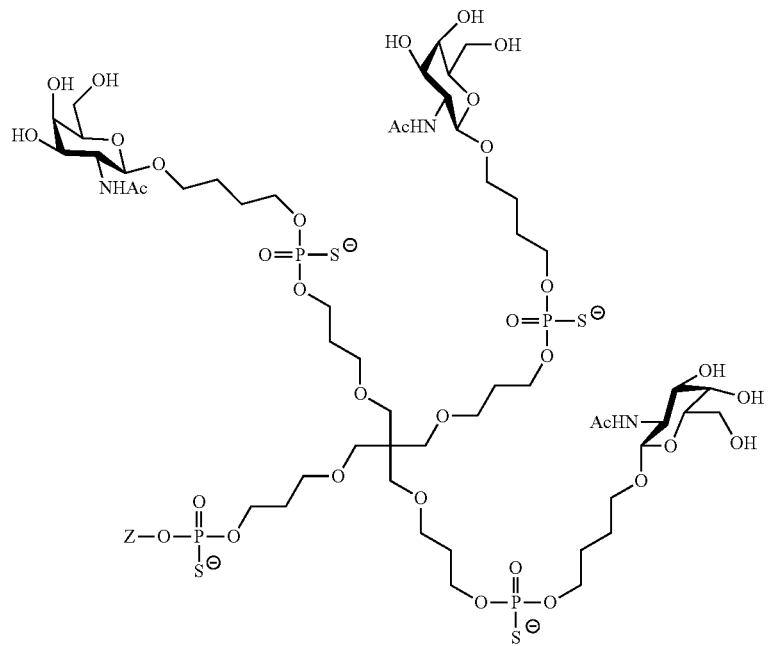
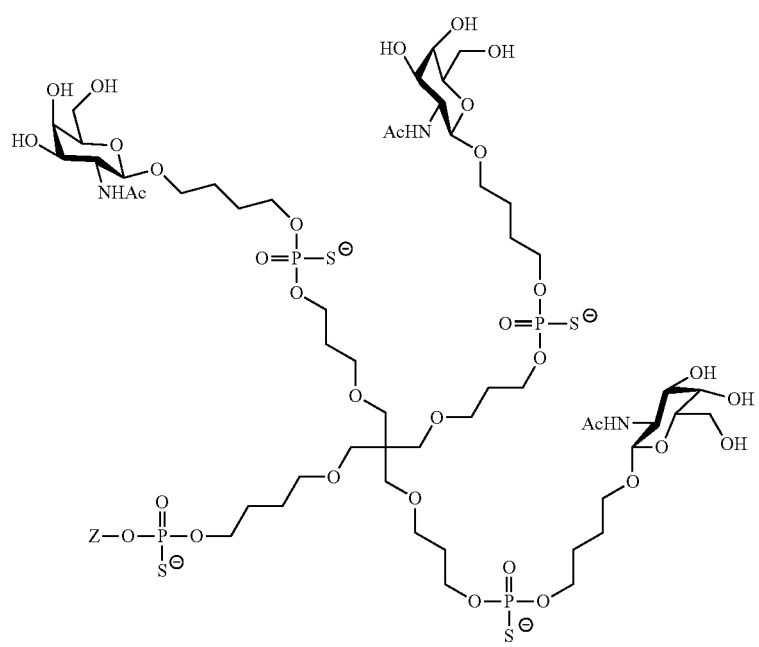

-continued
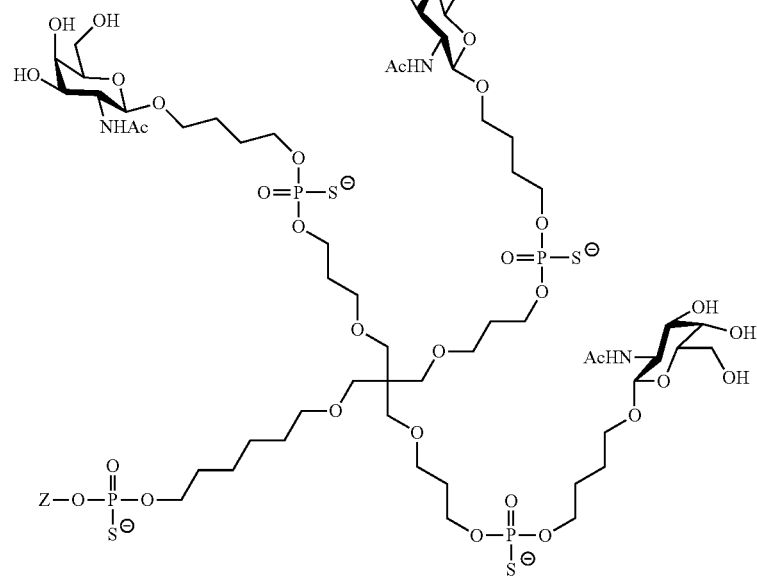
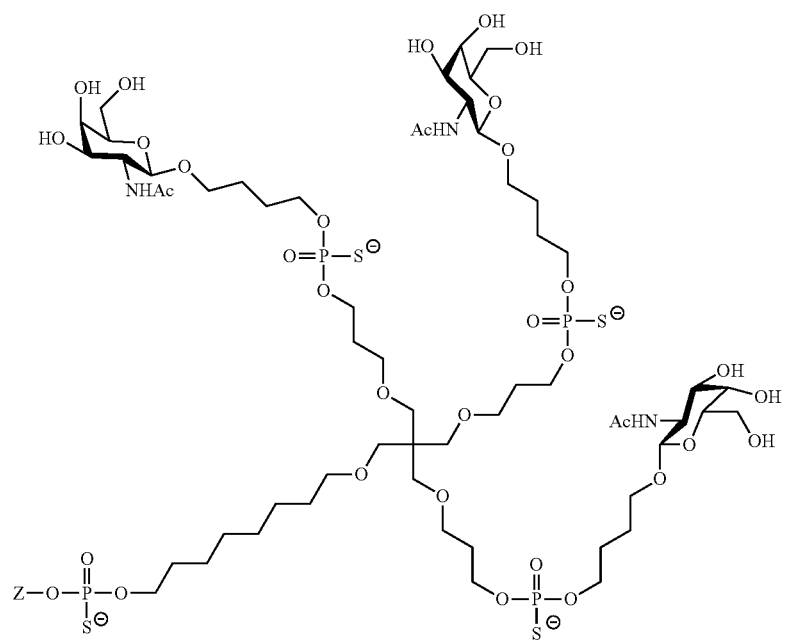

-continued
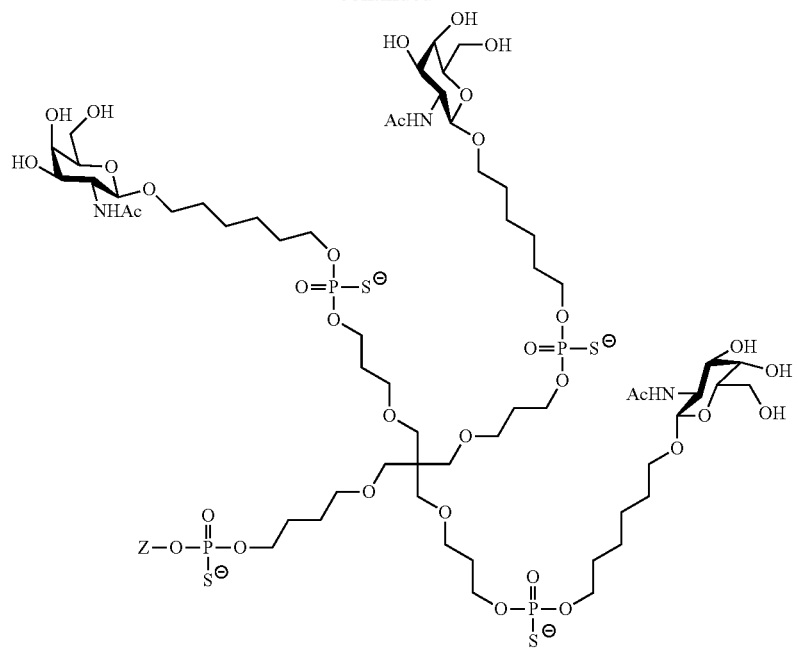
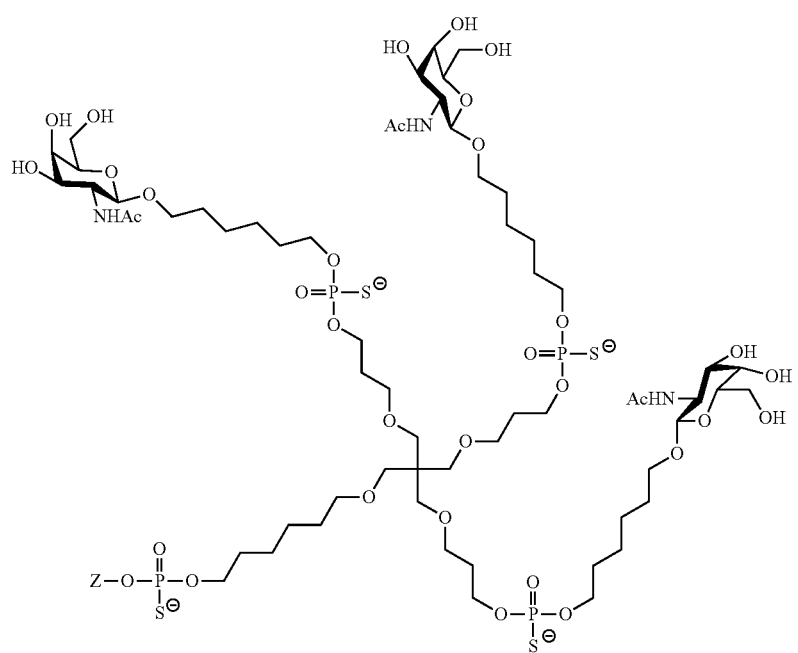

-continued

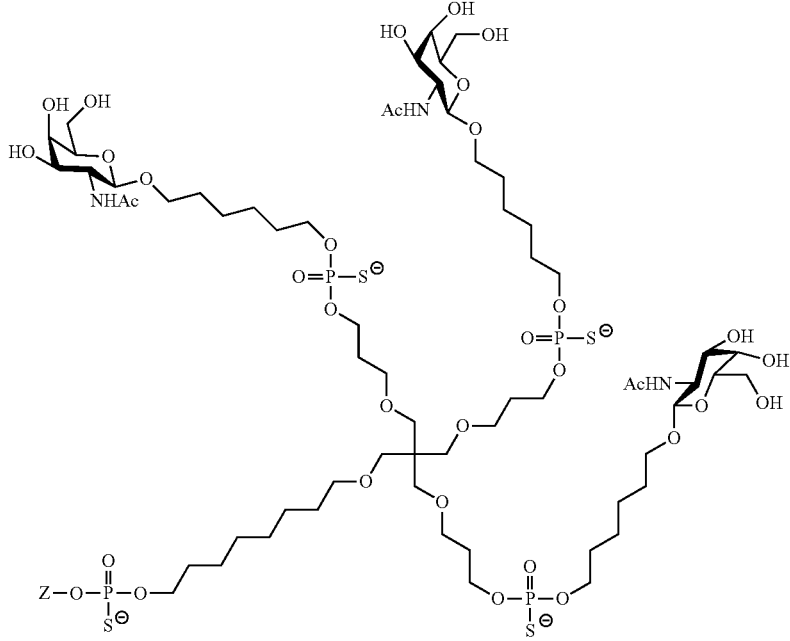

wherein Z is a nucleic acid of any one of statements 1 to 35.

45. A nucleic acid of any one of statements 39 to 44, wherein the ligand comprises

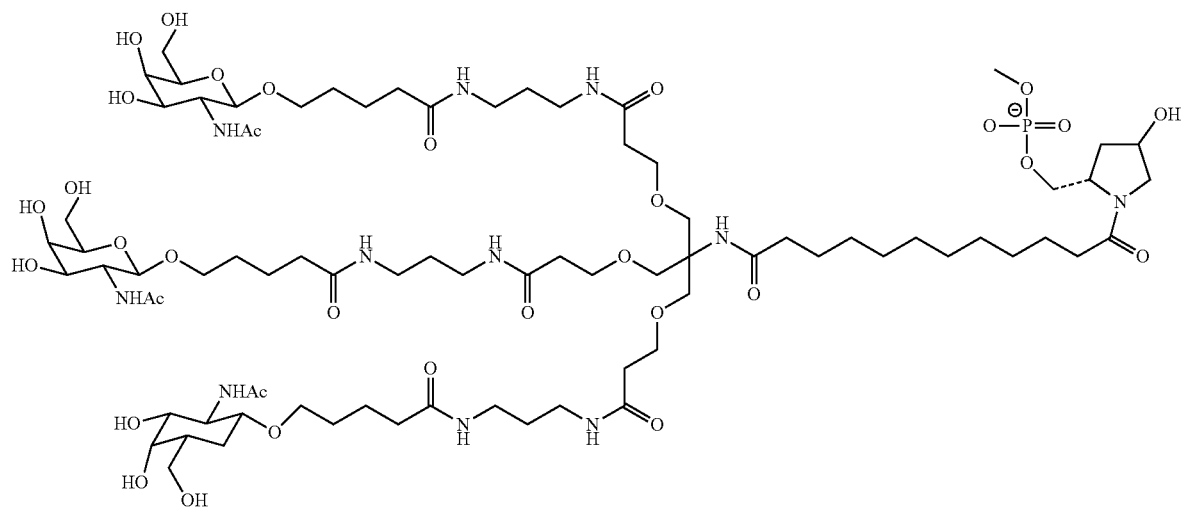

46. A nucleic acid or conjugated nucleic acid of any preceding statement, wherein the duplex comprises separate strands.

47. A nucleic acid or conjugated nucleic acid of any preceding statement, wherein the duplex comprises a single strand comprising a first strand and a second strand.

48. A composition comprising a nucleic acid or conjugated nucleic acid as defined in any of statements 1 to 47 and a formulation comprising:
 i) a cationic lipid, or a pharmaceutically acceptable salt thereof;
 ii) a steroid;
 iii) a phosphatidylethanolamine phospholipid;
 iv) a PEGylated lipid.

49. A composition according to statement 48 wherein in the formulation, the content of the cationic lipid component is from about 55 mol % to about 65 mol % of the overall lipid content of the lipid formulation, preferably about 59 mol % of the overall lipid content of the lipid formulation.

50. A composition
in statement 48 or 49, wherein the formulation comprises;
A cationic lipid having the structure;

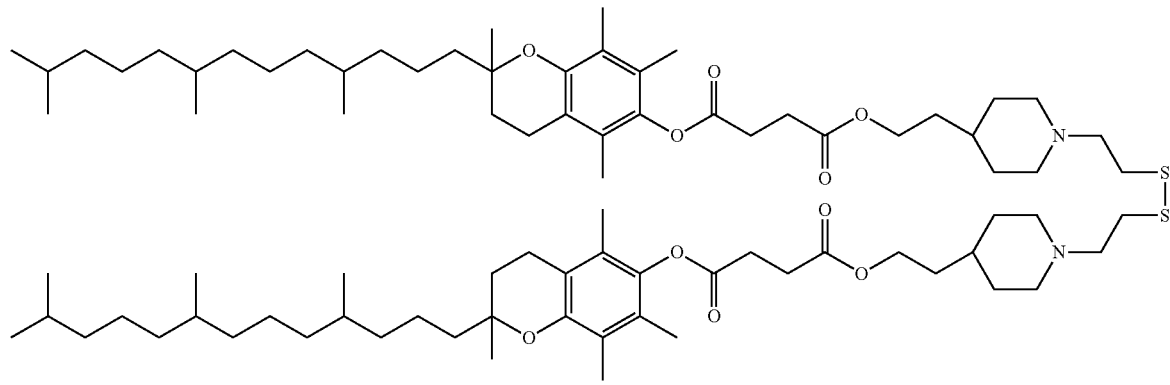 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

the steroid has the structure;

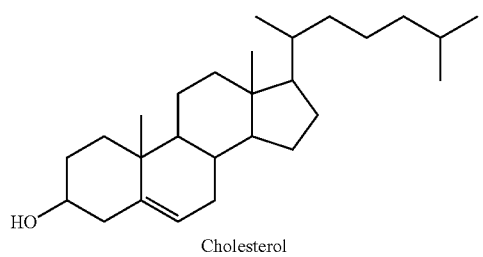 [SMILES: CC(C)CCCC(C)C1CCC2C3CC=C4CC(O)CCC4(C)C3CCC12C]

the a phosphatidylethanolamine phospholipid has the structure;

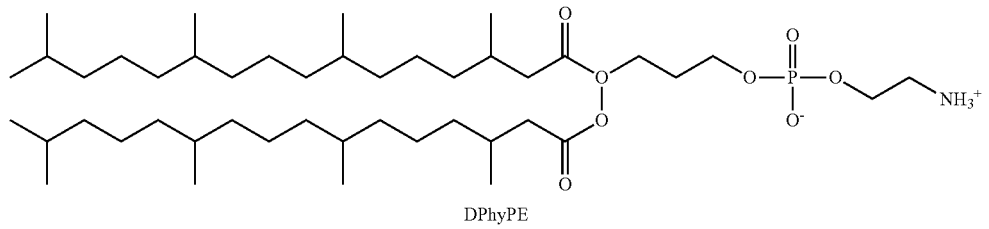

DPhyPE

And the PEGylated lipid has the structure;

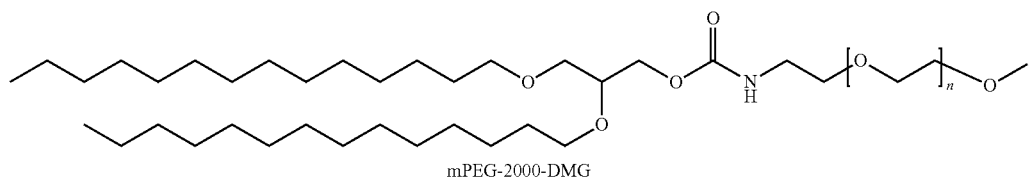

mPEG-2000-DMG

51. A composition comprising a nucleic acid or conjugated nucleic acid of any of statements 1 to 47 and a physiologically acceptable excipient.

52. A nucleic acid or conjugated nucleic acid according to any of statements 1 to 47 for use in the treatment of a disease or disorder.

53. Use of a nucleic acid or conjugated nucleic acid according to any of statements 1 to 47 in the manufacture of a medicament for treating a disease or disorder.

54. A method of treating a disease or disorder comprising administration of a composition comprising a nucleic acid or conjugated nucleic acid according to any of statements 1 to 47 to an individual in need of treatment.

55. The method of statement 54, wherein the nucleic acid or conjugated nucleic acid is administered to the subject subcutaneously or intravenously.

56. A process for making a nucleic acid or conjugated nucleic acid of any one of statements 1 to 47.

The invention claimed is:

1. A nucleic acid for inhibiting expression of a target gene in a cell, all nucleotides of the nucleic acid comprising a sugar modified at the 2' position, and the nucleic acid comprising at least one duplex region that comprises at least a portion of a first strand and at least a portion of a second strand that is at least partially complementary to the first strand, wherein said first strand is at least partially complementary to at least a portion of RNA transcribed from said target gene, wherein (i) the nucleotides of the first strand are modified with alternating 2' O-methyl modifications and 2' fluoro modifications, wherein positions 2 and 14 on the first strand starting from the 5' end are modified with 2' fluoro, and (ii) the nucleotides of the second strand are modified with 2' fluoro modifications at positions 11-13 counting from the 3' end starting at the first position of the double strand region, and the remaining modifications are 2' O-methyl modifications.

2. The nucleic acid according to claim 1, wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, or wherein the nucleic acid comprises a phosphorodithioate linkage.

3. The nucleic acid according to claim 1, conjugated with a ligand.

4. A composition comprising a nucleic acid of claim 1 and a physiologically acceptable excipient.

5. A method of treating a disease or disorder comprising administration of a composition comprising a nucleic acid of claim 1 to an individual in need of treatment.

6. A composition comprising a conjugated nucleic acid of claim 3 and a physiologically acceptable excipient.

7. A method of treating a disease or disorder comprising administration of a composition comprising a conjugated nucleic acid of claim 3 to an individual in need of treatment.

* * * * *